US007678803B2

(12) United States Patent
Huang et al.

(10) Patent No.: US 7,678,803 B2
(45) Date of Patent: Mar. 16, 2010

(54) QUINAZOLINE DERIVATIVES FOR THE TREATMENT OF CANCER

(75) Inventors: Kenneth He Huang, Chapel Hill, NC (US); James Veal, Apex, NC (US); Thomas Barta, Carrboro, NC (US); Emilie D. Smith, Apex, NC (US); Wei Ma, Cary, NC (US); Andy Ommen, Durham, NC (US)

(73) Assignee: Serenex, Inc., Durham, NC (US)

( * ) Notice: Subject to any disclaimer, the term of this patent is extended or adjusted under 35 U.S.C. 154(b) by 75 days.

(21) Appl. No.: 11/844,584

(22) Filed: Aug. 24, 2007

(65) Prior Publication Data

US 2008/0070935 A1 Mar. 20, 2008

Related U.S. Application Data

(60) Provisional application No. 60/823,441, filed on Aug. 24, 2006.

(51) Int. Cl.
*A61K 31/517* (2006.01)

(52) U.S. Cl. ................ 514/266.2; 544/292; 548/362.5; 548/510

(58) Field of Classification Search ............. 514/266.2; 544/292; 548/362.5, 510
See application file for complete search history.

(56) References Cited

U.S. PATENT DOCUMENTS

| | | | |
|---|---|---|---|
| 2004/0180889 | A1 | 9/2004 | Suto et al. |
| 2008/0269193 | A1 | 10/2008 | Huang et al. |

FOREIGN PATENT DOCUMENTS

| | | |
|---|---|---|
| WO | WO2004/111048 | 12/2004 |
| WO | WO2006/091963 | 8/2006 |
| WO | WO2008/009076 | 1/2008 |

OTHER PUBLICATIONS

Jordan, V. C. Nature Reviews: Drug Discovery, 2, 2003, p. 205.*

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Maloney A. et al., "HSP90 as a New Therapeutic Target for Cancer Therapy: The Story Unfolds", Expert Opinion on Biological Therapy, vol. 2, No. 1, Jan. 2002, pp. 3-24.

International Search Report for PCT/US2007/076769 dated Mar. 11, 2008.

* cited by examiner

*Primary Examiner*—James O Wilson
*Assistant Examiner*—Douglas M Willis
(74) *Attorney, Agent, or Firm*—Ye Hua; Jeffrey H. Tidwell; Stephen D. Prodnuk

(57) ABSTRACT

The current invention is directed toward compounds and pharmaceutically acceptable salts of Formula I

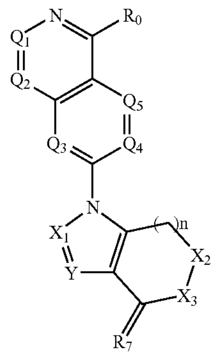

wherein $Q_1$ is $CR_1$, $Q_2$ is N, $Q_4$ and $Q_5$ are each $CR_1$, $Q_3$ is $CR_2$, $X_1$ is N or CRc, Y is $CR_c$, $X_2$ and $X_3$ are each $C(R_5)(R_6)$, $R_7$ is O. Compounds of Formula I are useful in the treatment of diseases and/or conditions related to cell proliferation, such as cancer The current invention is also directed toward pharmaceutical compositions comprising compounds of the invention.

46 Claims, No Drawings

QUINAZOLINE DERIVATIVES FOR THE TREATMENT OF CANCER

This application claims the benefit of U.S. Provisional Patent Application No. 60/823,441, filed Aug. 24, 2006, the disclosure of which is incorporated herein in its entirety.

BACKGROUND OF THE INVENTION

1. Field of the Invention

The invention relates to isoquinoline, quinazoline and phthalazine derivatives and more specifically to such compounds that are useful in the treatment and/or prevention of diseases and/or conditions related to cell proliferation, such as cancer, inflammation and inflammation-associated disorders, and conditions associated with angiogenesis. Compounds of the invention are also useful in the treatment and/or prevention of infectious diseases, in particular, fungal and viral infections.

2. Description of the Related Art

Cancer is characterized by abnormal cellular proliferation. Cancer cells exhibit a number of properties that make them dangerous to the host, typically including an ability to invade other tissues and to induce capillary ingrowth, which assures that the proliferating cancer cells have an adequate supply of blood. A hallmark of cancerous cells is their abnormal response to control mechanisms that regulate cell division in normal cells; thus, the cells continue to divide until they ultimately kill the host.

Angiogenesis is a highly regulated process under normal conditions, however many diseases are driven by persistent unregulated angiogenesis. Unregulated angiogenesis may either cause a particular disease directly or exacerbate an existing pathological condition. For example, ocular neovascularization has not only been implicated as the most common cause of blindness, but also is believed the dominant cause of many eye diseases. Further, in certain existing conditions, for example arthritis, newly formed capillary blood vessels invade the joints and destroy cartilage, or in the case of diabetes, new capillaries formed in the retina invade the vitreous, bleed, and cause blindness. Growth and metastasis of solid tumors are also dependent on angiogenesis (Folkman, J., Cancer Research, 46, 467-473 (1986), Folkman, J., Journal of the National Cancer Institute, 82, 4-6 (1989). It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone (Weidner, N., et al., The New England Journal of Medicine, 324(1), 1-8 (1991). Under conditions of unregulated angiogenesis, therapeutic methods designed to control, repress, and/or inhibit angiogenesis could lead to the abrogation or mitigation of these conditions and diseases.

Inflammation is related to a variety of disorders such as pain, headaches, fever, arthritis, asthma, bronchitis, menstrual cramps, tendonitis, bursitis, psoriasis, eczema, burns, dermatitis, inflammatory bowel syndrome, Crohn's disease, gastritis, irritable bowel syndrome, ulcerative colitis, vascular diseases, Hodgkin's disease, scleredoma, rheumatic fever, type I diabetes, myasthenia gravis, sarcoidosis, nephrotic syndrome, Behcet's syndrome, polymyositis, hypersensitivity, conjunctivitis, gingivitis, post-injury swelling, myocardial ischemia, cerebral ischemia (stroke), sepsis, and the like.

Heat-shock protein 90 (HSP-90) is a cellular chaperone protein required for the activation of several eukaryotic protein kinases, including the cyclin-dependent kinase CDK4. Geldanamycin, an inhibitor of the protein-refolding activity of HSP-90, has been shown to have antiproliferative and antitumor activities.

HSP-90 is a molecular chaperone that guides the normal folding, intracellular disposition and proteolytic turnover of many key regulators of cell growth and survival. Its function is subverted during oncogenesis to make malignant transformation possible and to facilitate rapid somatic evolution, and to allow mutant proteins to retain or even gain function. Inhibition of HSP-90 will slow those process and thus has therapeutic use (Whitesell L, Lindquist, S L, Nature Rev. Cancer, 2005, 10, 761-72).

Ansamycin antibiotics, e.g., herbimycin A (HA), geldanamycin (GM), and 17-allylaminogeldanamycin (17-AAG) are thought to exert their anticancerous effects by tight binding of the N-terminus pocket of HSP-90, thereby destabilizing substrates that normally interact with HSP-90 (Stebbins, C. et al. Cell 1997, 89, 239-250). This pocket is highly conserved and has weak homology to the ATP-binding site of DNA gyrase (Stebbins, C. et al., supra; Grenert, J. P. et al. J. Biol. Chem. 1997, 272, 23843-50).

In vitro and in vivo studies have demonstrated that occupancy of this N-terminal pocket by ansamycins and other HSP-90 inhibitors alters HSP-90 function and inhibits protein folding. At high concentrations, ansamycins and other HSP-90 inhibitors have been shown to prevent binding of protein substrates to HSP-90 (Scheibel, T. H. et al. Proc. Natl. Acad. Sci. USA 1999, 96, 1297-302; Schulte, T. W. et al. J. Biol. Chem. 1995, 270, 24585-8 Whitesell, L., et al. Proc. Natl. Acad. Sci. USA 1994, 91, 8324-8328). Ansamycins have also been demonstrated to inhibit the ATP-dependent release of chaperone-associated protein substrates (Schneider, C. L. et al. Proc. Natl. Acad. Sci., USA 1996, 93, 14536-41; Sepp-Lorenzino et al. J. Biol Chem. 1995, 270, 16580-16587). In either event, the substrates are degraded by a ubiquitin-dependent process in the proteasome (Schneider, C. L., supra; Sepp-Lorenzino, L., et al. J. Biol. Claim. 1995, 270, 16580-16587; Whitesell, L. et al. Proc. Natl. Acad. Sci. USA 1994, 91, 8324-8328). HSP-90 substrate destabilization occurs in tumor and non-transformed cells alike and has been shown to be especially effective on a subset of signaling regulators, e.g., Raf (Schulte, T. W. et al., Biochem. Biophys. Res. Commun. 1997, 239, 655-9 Schulte, T. W., et al., J. Biol. Chem. 1995, 270, 24585-8), nuclear steroid receptors (Segnitz, B.; U. Gehring J. Biol. Chem. 1997, 272, 18694-18701; Smith, D. F. et al. Mol. Cell. Biol. 1995, 15, 6804-12), v-Src (Whitesell, L., et al. Proc. Natl. Acad. Sci. USA 1994, 91, 8324-8328) and certain transmembrane tyrosine kinases (Sepp-Lorenzino, L. et al. J. Biol. Chez. 1995, 270, 16580-16587) such as EGF receptor (EGFR) and HER2/Neu (Hartmann, F., et al. Int. J. Cancer 1997, 70, 221-9; Miller, P. et al. Cancer Res. 1994, 54, 2724-2730; Mimnaugh, E. G., et al. J. Biol. Clzem. 1996, 271, 22796-801; Schnur, R. et al. J. Med. Chenu. 1995, 38, 3806-3812), CDK4, and mutant p 53. Erlichman et al. Proc. AACR 2001, 42, abstract 4474. The ansamycin-induced loss of these proteins leads to the selective disruption of certain regulatory pathways and results in growth arrest at specific phases of the cell cycle (Muise-Heimericks, R. C. et al. J. Biol. Chez. 1998, 273, 29864-72), and apoptosis, and/or differentiation of cells so treated (Vasilevskaya, A. et al. Cancer Res., 1999, 59, 3935-40). Inhibitors of HSP-90 thus will be useful for the treatment and/or prevention of many types of cancers and proliferative disorders, and may also be useful as traditional antibiotics.

Inhibition of HSP-90 is also known to result in up regulation of the expression of the chaperone HSP70. HSP70 up regulation is considered to be of therapeutic benefit for treatment of a wide range of neurodegenerative diseases including, but not limited to: Alzheimer's disease; Parkinson's disease; Dementia with Lewy bodies; Amyotropic lateral sclerosis (ALS); Polyglutamine disease; Huntington's disease; Spinal and bulbar muscular atrophy (SBMA); and Spinocerebellar ataxias (SCA1-3, 7). Therefore, the compounds described in the invention are of potential therapeutic use for treatment of such neurodegenerative diseases (Muchowski, P. J., Wacker J. L., Nat. Rev. Neurosci. 2005, 6, 11-22.; Shen H. Y., et al. J. Biol. Chem. 2005, 280, 39962-9).

Inhibition of HSP-90 also has anti-fungal activity, both as a stand alone therapy and in combination with standard anti-fungal therapies such as the azole class of drugs. Therefore, the compounds described in the invention are of potential therapeutic use for treatment of fungal infections including, but not limited to, life threatening systemic fungal infections (Cowen, L. E., Lindquist, S., Science 2005, 309, 2185-9).

HSP-90 has also been shown to be important to viral transcription and replication, in particular for such processes in HIV-1 and Hepatitis C virus. See J Biol Chem. 2000 Jan. 7; 275(1):279-87; J Virol. 2004 December; 78(23):13122-31; and Biochem Biophys Res Commun. 2007 Feb. 23; 353(4): 882-8. Epub 2006 Dec. 22. Inhibitors of HSP-90 have been shown to attenuate infection in animal models of polio infection. See Genes Dev. 2007 (21) 195-205.

Inhibitors of HSP-90 have been shown to attenuate inflammation via lowering the level of a number of client proteins associated inflammation process. See FASEB J. 2007 July; 21(9):2113-23.

Inhibition of HSP-90 is also expected to result in antimalarial activity; thus, inhibitors of this protein are useful as antimalarial drugs.

There is a continuing need for new methods of treating cancer, inflammation and inflammation-associated disorders, and conditions or diseases related to uncontrolled angiogenesis.

SUMMARY OF THE INVENTION

In a broad aspect, the invention encompasses compounds of formula I shown below, pharmaceutical compositions containing those compounds and methods employing such compounds or compositions in the treatment of diseases and/or conditions related to cell proliferation, such as cancer, inflammation, arthritis, angiogenesis, or the like.

In a first aspect, the invention provides compounds of formula I,

I

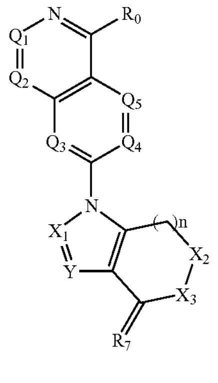

and pharmaceutically acceptable salts thereof, wherein $R_0$, $R_7$, $Q_1$-$Q_5$, $X_1$-$X_3$, and Y are defined herein.

The invention also includes intermediates that are useful in making the compounds of formula I.

The invention also provides pharmaceutical compositions comprising a compound or pharmaceutically acceptable salt of Formula I and at least one pharmaceutically acceptable carrier, solvent, adjuvant or diluent.

The invention further provides methods of treating disease such as cancer, inflammation, arthritis, angiogenesis, and infection in a patient in need of such treatment, comprising administering to the patient a compound or pharmaceutically acceptable salt of Formula I, or a pharmaceutical composition comprising a compound or salt of Formula I.

The invention also provides the use of a compound or salt according to Formula I for the manufacture of a medicament for use in treating cancer, inflammation, arthritis, angiogenesis, or infection.

The invention also provides methods of preparing the compounds of formula I and intermediates used in those methods.

The invention also provides methods of treating a disease or condition related to cell proliferation comprising administering a therapeutically effective amount of a compound or salt of Formula I to a patient in need of such treatment.

The invention also provides methods of treating a disease or condition related to cell proliferation comprising administering a therapeutically effective amount of a compound or salt of Formula I to a patient in need of such treatment, where the disease of condition is cancer, inflammation, or arthritis.

The invention further provides methods of treating a subject suffering from a disease or disorder of proteins that are either client proteins for HSP-90 or indirectly affect its client proteins, comprising administering to a subject in need of such treatment a therapeutically effective amount of a compound or salt of Formula I.

The invention further provides methods of treating a subject suffering from a disease or disorder of proteins that are either client proteins for HSP-90 or indirectly affect its client proteins, comprising administering to a subject in need of such treatment a therapeutically effective amount of a compound or salt of Formula I, wherein the HSP-90 mediated disorder is selected from the group of inflammatory diseases, infections, autoimmune disorders, stroke, ischemia, cardiac disorders, neurological disorders, fibrogenetic disorders, proliferative disorders, tumors, leukemias, neoplasms, cancers, carcinomas, metabolic diseases and malignant disease.

The invention further provides methods of treating a subject suffering from a fibrogenetic disorder of proteins that are either client proteins for HSP-90 or indirectly affect its client proteins, comprising administering to a subject in need of such treatment a therapeutically effective amount of a compound or salt of Formula I, wherein the fibrogenetic disorder is selected from the group of scleroderma, polymyositis, systemic lupus, rheumatoid arthritis, liver cirrhosis, keloid formation, interstitial nephritis and pulmonary fibrosis.

The invention provides methods of protecting a subject from infection caused by an organism selected from *Plasmodium* species, preferably *Plasmodium falciparum*. These methods comprise administering a compound or salt of Formula I, preferably in an effective amount, to a subject at risk of infection due to exposure to such organism.

The invention additionally provides methods of reducing the level of infection in a subject where the infection is caused by an organism selected from *Plasmodium* species, again preferably *Plasmodium falciparum*. These methods comprise administering to an infected subject an effective amount of a compound or salt of Formula I.

The invention further provides methods for treating a patient infected with a metazoan parasite. These methods involve administering an amount of a compound of formula I effective to kill the parasite.

The invention further provides methods for treating a patient infected with a metazoan parasite wherein the parasite is *Plasmodium falciparum*. These methods involve administering an amount of a compound or salt of formula I effective to kill the parasite.

The invention also provides methods of treating and/or preventing viral infections in patients in need of such treatment comprising administration of a compound or salt of formula I.

The invention further encompasses kits comprising compounds of the invention or pharmaceutical compositions thereof in a package with instructions for using the compound or composition.

In another aspect, the invention provides combination therapy, i.e., treatment of a patient in need thereof with a combination of a compound of formula I with other drugs or therapies known to be effective to treat the disease to enhance overall effectiveness of therapy. The combination may be in a single dosage form, e.g., a single tablet, or may involve simultaneous or sequential administration of two or more different dosage forms, e.g., an HSP-90 inhibitor of the invention, intravenous chemotherapy administration, and radiation therapy.

The invention further provides methods for treating a fungal infection in a patient in need of such treatment, comprising administering an effective amount of a compound or salt of Formula I and an optional anti-fungal agent or drug.

DETAILED DESCRIPTION OF THE INVENTION

In a first aspect, the invention provides compounds of formula I,

I

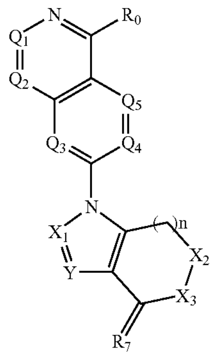

and pharmaceutically acceptable salts thereof, wherein $R_0$ is hydrogen, halogen, cyano, nitro, or -A-$R_{0'}$, wherein A is a bond, —O—, —S—, —N($R_{0'}$)—, —N($R_{0'}$)CO—, —N[C(O)$R_{0'}$]C(O)—, —N($R_{0'}$)$SO_2$—, —$SO_2$N($R_{0'}$)—, —$SO_2$—, —CO—, —$CO_2$—, or —C(O)N($R_{0'}$)—; and each $R_{0'}$ is independently hydrogen, $C_1$-$C_{10}$ haloalkyl, $C_1$-$C_{10}$ alkyl, $C_2$-$C_{10}$ alkenyl, $C_2$-$C_{10}$ alkynyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide;

$Q_1$, $Q_4$, and $Q_5$ are each independently N or $CR_1$, wherein each $R_1$ is hydrogen, halogen, cyano, nitro, or —B—$R_{1'}$, wherein B is a bond, —O—, —S—, —N($R_{1'}$)—, —N($R_{1'}$)CO—, —N[C(O)$R_{1'}$]C(O)—, —N($R_{1'}$)$SO_2$, —$SO_2$N($R_{1'}$)—, —$SO_2$—, —CO—, —$CO_2$—, or —C(O)N($R_{1'}$)—; and each $R_{1'}$ is independently hydrogen, $C_1$-$C_{10}$ haloalkyl, $C_1$-$C_{10}$ alkyl, $C_2$-$C_{10}$ alkenyl, $C_2$-$C_{10}$ alkynyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide;

$Q_2$ and $Q_3$ are each independently N or $CR_2$, wherein each $R_2$ is independently (a) H, (b) halogen, or (c) a $C_1$-$C_{15}$ alkyl group where up to five of the carbon atoms in said alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{22}$ is (i) heteroaryl, (ii) aryl, (iii) saturated or unsaturated $C_3$-$C_{10}$ cycloalkyl, or (iv) saturated or unsaturated $C_2$-$C_{10}$ heterocycloalkyl, wherein each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$)alkyl, —$SO_2$—($C_1$-$C_6$)alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, ($C_1$-$C_6$)alkoxy, or mono- or di-($C_1$-$C_{10}$)alkylamino; and each $R_{22}$ is optionally fused to a $C_6$-$C_{10}$ aryl group, $C_5$-$C_8$ saturated cyclic group, or a $C_5$-$C_{10}$ heterocycloalkyl group;

wherein each (c) is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, $—SO_2—(C_1-C_6)$alkyl, $—SO_2NH_2$, $—SO_2NH—(C_1-C_6)$alkyl, $—SO_2NH$-aryl, $—SO_2$-aryl, $—SO—(C_1-C_6)$alkyl, $—SO_2$-aryl, $C_1-C_6$ alkoxy, $C_2-C_{10}$ alkenyloxy, $C_2-C_{10}$ alkynyloxy, mono- or di-$(C_1-C_{10})$alkylamino, or $R_{23}$, wherein $R_{23}$ is (1) heteroaryl, (2) aryl, (3) saturated or unsaturated $C_5-C_{10}$ cycloalkyl, or (4) saturated or unsaturated $C_5-C_{10}$ heterocycloalkyl, and the $R_{23}$ groups are optionally substituted at least one group which is independently hydroxy, oxo, halo, amino, cyano, nitro, —SH, $—S—(C_1-C_6)$alkyl, $—SO_2—(C_1-C_6)$alkyl, $—SO_2$-aryl, $—SO—(C_1-C_6)$alkyl, —SO-aryl, $—SO_2NH_2$, $—SO_2NH—(C_1-C_6)$alkyl, $—SO_2NH$-aryl, $(C_1-C_6)$alkoxy, or mono- or di-$(C_1-C_{10})$alkylamino;

$R_7$ is O, S, or $NR_{7'}$, wherein $R_{7'}$ is H, —OH, $—NH_2$, $—NHR_{22}$, $—NH—(C_1-C_6$ alkyl), $—O—(C_0-C_6)$alkyl-$R_{22}$, or $—(C_1-C_6$ alkoxy optionally substituted with carboxy);

$X_1$ and Y are each independently N or $CR_C$, wherein each $R_C$ independently is hydrogen, halogen, cyano, nitro, $C_1-C_{10}$alkyl, $C_2-C_{10}$alkenyl, $C_2-C_{10}$ alkynyl, $C_1-C_{10}$ haloalkyl, $C_3-C_7$ cycloalkyl, $C_3-C_7$ cycloalkyl $(C_1-C_{10})$ alkyl, heterocycloalkyl, aryl, or heteroaryl, wherein each alkyl, aryl, cycloalkyl, heterocycloalkyl, and heteroaryl group is optionally substituted with from 1-4 groups that are independently $C_1-C_6$ alkyl, $C_1-C_6$ alkoxy, halogen, hydroxy, amino, mono- or di-$(C_1-C_6)$ alkylamino, cyano, nitro, halo$(C_1-C_6)$alkyl, halo$(C_1-C_6)$alkoxy, carboxamide, heterocycloalkyl, aryl, or heteroaryl, wherein the aryl and heteroaryl groups are optionally substituted with from 1-4 groups that are independently $C_1-C_6$ alkyl, $C_1-C_6$ alkoxy, halogen, hydroxy, amino, mono- or di-$(C_1-C_6)$alkylamino, halo$(C_1-C_6)$alkyl, or carboxamide;

$X_2$ and $X_3$ are independently $C(R_5)(R_6)$, O, $N(R_5)$, or $S(O)_p$ wherein p is 0, 1, or 2; and each $R_5$ and $R_6$ is independently hydrogen, $C_1-C_6$ alkyl, or mono- or di-$(C_1-C_6)$alkylamino$(C_1-C_6)$alkyl, or $R_5$ and $R_6$ together with the carbon to which they are attached form a 3-8 membered cycloalkyl or heterocycloalkyl ring; and n is 0, 1, 2, 3, or 4, provided that (i) one and only one of $Q_1$ and $Q_2$ may be N; and (ii) one and only one of $Q_3$, $Q_4$ and $Q_5$ may be N.

Preferred compounds of formula I include those where $R_7$ is O or N—OH. More preferred compounds of formula I are those wherein $R_7$ is O.

Other preferred compounds of formula I are those where n is 0, 1, or 2. More preferred compounds of formula I are those wherein n is 1.

Other preferred compounds of formula I are those where $R_0$ is hydrogen, halogen, $C_1-C_3$ alkyl or -A-$R_{0'}$, wherein A is —O—, $—N(R_{0'})—$, $—N(R_{0'})CO—$, $—N[C(O)R_{0'}]C(O)—$, or $—N(R_{0'})SO_2—$; and each $R_{0'}$ is independently hydrogen, $C_1-C_{10}$ haloalkyl, $C_1-C_{10}$ alkyl, or $C_3-C_{10}$ cycloalkyl, $C_2-C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1-C_6$ alkyl, $C_1-C_6$ alkoxy, halogen, hydroxy, carboxy, oxo, amino, mono- or di-$(C_1-C_6)$alkylamino, cyano, nitro, halo$(C_1-C_6)$alkyl, halo$(C_1-C_6)$alkoxy, carboxamide, heterocycloalkyl, aryl, or heteroaryl.

More preferred compounds of formula I are those wherein $R_0$ is hydrogen, halogen, hydroxyl, $C_1-C_3$ alkyl or -A-$R_{0'}$, wherein A is $—N(R_{0'})—$, $—N(R_{0'})CO—$, $—N[C(O)R_{0'}]C(O)—$, or $—N(R_0)SO_2—$; and each $R_{0'}$ is independently hydrogen, $C_1-C_{10}$ haloalkyl, $C_1-C_{10}$ alkyl, or $C_3-C_{10}$ cycloalkyl, $C_2-C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1-C_6$ alkyl, $C_1-C_6$ alkoxy, halogen, hydroxy, carboxy, oxo, amino, mono- or di-$(C_1-C_6)$alkylamino, cyano, nitro, halo$(C_1-C_6)$alkyl, halo$(C_1-C_6)$alkoxy, carboxamide, heterocycloalkyl, aryl, or heteroaryl.

Even more preferred compounds of formula I are those where $R_0$ is hydroxyl. Other even more preferred compounds of formula I are those where $R_0$ is $—N(R_{0'})_2$, $—N(R_{0'})COR_{0'}$, $—N [C(O) R_{0'}]C(O)$ or $—N(R_{0'})SO_2R_{0'}$; and each $R_0$ is independently hydrogen, $C_1-C_{10}$ haloalkyl, $C_1-C_{10}$ alkyl, or $C_3-C_{10}$ cycloalkyl, $C_2-C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1-C_6$ alkyl, $C_1-C_6$ alkoxy, halogen, hydroxy, carboxy, oxo, amino, mono- or di-$(C_1-C_6)$alkylamino, cyano, nitro, halo$(C_1-C_6)$alkyl, halo$(C_1-C_6)$alkoxy, carboxamide, heterocycloalkyl, aryl, or heteroaryl.

Other even more preferred compounds of formula I are those where $R_0$ is $—N(R_{0'})_2$, and each $R_{0'}$ is independently hydrogen, $C_1-C_{10}$ haloalkyl, $C_1-C_{10}$ alkyl, or $C_3-C_{10}$ cycloalkyl, $C_2-C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1-C_6$ alkyl, $C_1-C_6$ alkoxy, halogen, hydroxy, carboxy, oxo, amino, mono- or di-$(C_1-C_6)$alkylamino, cyano, nitro, halo$(C_1-C_6)$alkyl, halo$(C_1-C_6)$alkoxy, carboxamide, heterocycloalkyl, aryl, or heteroaryl.

Other even more preferred compounds of formula I are those where $R_0$ is $—N(R_{0'})_2$, and each $R_{0'}$ is independently hydrogen, $C_1-C_{10}$ haloalkyl, $C_1-C_{10}$ alkyl.

Other even more preferred compounds of formula I are those where $R_0$ is $—NH_2$.

Other even more preferred compounds of formula I are those where $R_0$ is hydrogen, halogen, hydroxyl or $C_1-C_3$ alkyl.

Other preferred compounds of formula I are those where $Q_1$ is $CR_1$ and $Q_2$ is N.

Other preferred compounds of formula I are those where $Q_1$ is $CR_1$ and $Q_2$ is N, wherein $R_1$ is hydrogen, amino or $—B—R_1$, wherein B is a bond, —O—, $—N(R_{1'})—$, $—N(R_{1'})CO—$, $—N[C(O)R_{1'}]C(O)—$, $—N(R_{1'})SO_2$; and each $R_1$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

More preferred compounds of formula I are those where $Q_1$ is $CR_1$ and $Q_2$ is N, wherein $R_1$ is hydrogen, halogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

More preferred compounds of formula I are those where $Q_1$ is $CR_1$ and $Q_2$ is N, wherein $R_1$ is hydrogen, halogen, —OH, —$C_1$-$C_6$ alkoxy, or —B—$R_{1'}$, wherein B is a bond, or —N($R_{1'}$)—, and each $R_1$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

Other preferred compounds of formula I are those where $Q_3$ is $CR_2$, and $Q_4$ and $Q_5$ are $CR_1$.

More preferred compounds of formula I are those where $Q_3$ is $CR_2$, and $Q_4$ and $Q_5$ are $CR_1$, wherein each $R_1$ is independently H, halogen, or $C_1$-$C_{15}$ alkyl.

More preferred compounds of formula I are those where $Q_3$ is $CR_2$, and $Q_4$ and $Q_5$ are $CR_1$, wherein each $R_1$ is independently H or halogen.

Other preferred compounds of formula I are those where $Q_3$ is N.

More preferred compounds of formula I are those where $Q_3$ is N and $Q_4$ and $Q_5$ are $CR_1$.

More preferred compounds of formula I are those where $Q_3$ is N and $Q_4$ and $Q_5$ are $CR_1$, wherein each $R_1$ is independently H, halogen, or $C_1$-$C_{15}$ alkyl.

More preferred compounds of formula I are those where $Q_3$ is N and $Q_4$ and $Q_5$ are $CR_1$, wherein each $R_1$ is independently H or halogen.

Other preferred compounds of formula I are those where $X_1$ is N.

Other preferred compounds of formula I are those where Y is N.

Other preferred compounds of formula I are those where $X_1$ is $CR_C$.

Other preferred compounds of formula I are those where Y is $CR_C$.

More preferred embodiments of formula I are those compounds where $X_1$ is N and Y is $CR_C$. Even more preferred compounds of formula I are those where, $X_1$ is N and Y is $CR_C$, wherein $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$) alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

Even more preferred compounds of formula I are those where, $X_1$ is N and Y is $CR_C$, wherein $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

Even more preferred compounds of formula I are those where, $X_1$ is N and Y is $CR_C$, wherein $R_C$ is hydrogen, halogen, $C_1$-$C_3$ alkyl, $C_1$-$C_3$ haloalkyl, cyclopropyl, or cyclopropylmethyl.

Even more preferred compounds of formula I are those where, $X_1$ is N and Y is $CR_C$, wherein $R_C$ is independently hydrogen, halogen, methyl, ethyl, fluoromethyl, difluoromethyl, trifluoromethyl, cyclopropyl, or cyclopropylmethyl.

In another embodiment, more preferred compounds formula I are those where $X_1$ and Y are each $CR_C$, wherein each $R_C$ is independently hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$) alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

Even more preferred compounds of formula I are those where, $X_1$ and Y are each $CR_C$, wherein each $R_C$ is independently hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

Even more preferred compounds of formula I are those where, $X_1$ and Y are each $CR_C$, wherein each $R_C$ is independently hydrogen, halogen, $C_1$-$C_3$ alkyl, $C_1$-$C_3$ haloalkyl, cyclopropyl, or cyclopropylmethyl.

Even more preferred compounds of formula I are those where, $X_1$ and Y are each $CR_C$, wherein each $R_C$ is independently hydrogen, halogen, methyl, ethyl, fluoromethyl, difluoromethyl, trifluoromethyl, cyclopropyl, or cyclopropylmethyl.

In another embodiment, preferred compounds of formula I are those where $X_3$ is $CH_2$.

In another embodiment, preferred compounds of formula I are those where $X_2$ is $CR_5R_6$.

In a preferred embodiment, the invention provides compounds of formula I where $X_3$ is $CH_2$ and $X_2$ is $CR_5R_6$.

In another more preferred embodiment, the invention provides compounds of formula I where $X_3$ is $CH_2$ and $X_2$ is $CR_5R_6$, wherein $R_5$ and $R_6$ are each independently hydrogen or $C_1$-$C_6$ alkyl.

In another more preferred embodiment, the invention provides compounds of formula I where $X_3$ is $CH_2$ and $X_2$ is $CR_5R_6$, wherein $R_5$ and $R_6$ are each independently hydrogen or $C_1$-$C_3$ alkyl.

In another embodiment, the invention provides compounds of formula I where $X_3$ is $CH_2$ and $X_2$ is $CR_5R_6$, wherein $R_5$ and $R_6$ together with the carbon to which they are attached form a 3-8 membered cycloalkyl or heterocycloalkyl ring.

In a preferred embodiment, the invention provides compounds of formula I where $X_3$ is $CH_2$ and $X_2$ is $CR_5R_6$, wherein $R_5$ and $R_6$ together with the carbon to which they are attached form a 3- or 4-membered cycloalkyl.

In another embodiment, the invention provides compounds of formula II, (II)

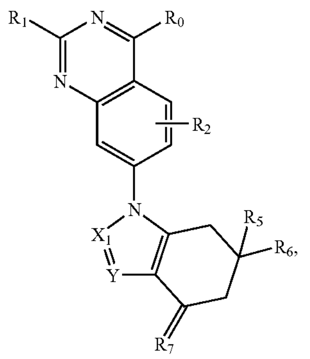

wherein $R_0$, $R_1$, $R_2$, $R_5$, $R_6$, $R_7$, $X_1$, and Y are as defined for formula I.

In another embodiment, the invention provides compounds of formula II where $R_7$ is O or N—OH.

More preferred compounds of formula II are those wherein $R_7$ is O.

In another embodiment, the invention provides compounds of formula II where $R_0$ is hydrogen, halogen, $C_1$-$C_3$ alkyl, or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a preferred embodiment, the invention provides compounds of formula II wherein $R_0$ is hydrogen, halogen, hydroxyl, $C_1$-$C_3$ alkyl, or -A-$R_{0'}$, wherein A is —N($R_{0'}$)—, —N($R_{0'}$)CO—, —N[C(O)$R_{0'}$]C(O)—, or —N($R_0$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula II where $R_0$ is hydroxyl, hydrogen, halogen, $C_1$-$C_3$ alkyl.

In a more preferred embodiment, the invention provides compounds of formula II where $R_0$ is —N($R_{0'}$)$_2$—, —N($R_{0'}$)$COR_0$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula II where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula II where $R_0$ is —N($R_{0'}$)$_2$—, and each $R_{0'}$ is independently hydrogen, $C_1$-$C_{10}$ haloalkyl, $C_1$-$C_{10}$ alkyl.

In a more preferred embodiment, the invention provides compounds of formula II where $R_0$ is —$NH_2$.

In a more preferred embodiment, the invention provides compounds of formula II where $R_0$ is hydroxyl, hydrogen, halogen, $C_1$-$C_3$ alkyl.

In another embodiment, the invention provides compounds of formula II where $R_1$ is hydrogen, halogen, or —B—$R_{1'}$, wherein B is a bond, —O—, —N($R_{1'}$)—, —N($R_{1'}$)CO—, —N[C(O)$R_{1'}$]C(O)—, —N($R_1$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula II where $R_1$ is hydrogen, halogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula II where $R_1$ is hydrogen, —OH, —$C_1$-$C_6$alkoxy, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula II where $R_1$ is hydrogen, halogen, —OH, —$C_1$-$C_6$ alkoxy, —$C_1$-$C_6$ alkyl, or —$NH_2$.

In a preferred embodiment, the invention provides compounds of formula II where $X_1$ is N.

In a preferred embodiment, the invention provides compounds of formula II where Y is N.

In a preferred embodiment, the invention provides compounds of formula II where $X_1$ is $CR_C$.

In a preferred embodiment, the invention provides compounds of formula II where Y is $CR_C$.

In a more preferred embodiment, the invention provides compounds of formula II where $X_1$ is N and Y is $CR_C$. In a another embodiment, the invention provides compounds of formula II where, $X_1$ is N and Y is $CR_C$, wherein $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula II where $X_1$ is N and Y is $CR_C$, wherein $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl.

Even more preferred compounds of formula II are those where, $X_1$ is N and Y is $CR_C$, wherein $R_C$ is hydrogen, halogen, $C_1$-$C_3$ alkyl, $C_1$-$C_3$ haloalkyl, cyclooropyl, or cyclopropylmethyl.

Even more preferred compounds of formula II are those where, $X_1$ is N and Y is $CR_C$, wherein $R_C$ is independently hydrogen, halogen, methyl, ethyl, fluoromethyl, difluoromethyl, trifluoromethyl, cyclopropyl, or cyclopropylmethyl.

In another embodiment, more preferred compounds formula II are those where $X_1$ and Y are each $CR_C$, wherein each $R_C$ is independently hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$) alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

Even more preferred compounds of formula II are those where, $X_1$ and Y are each $CR_C$, wherein each $R_C$ is independently hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

Even more preferred compounds of formula II are those where, $X_1$ and Y are each $CR_C$, wherein each $R_C$ is independently hydrogen, halogen, $C_1$-$C_3$ alkyl, $C_1$-$C_3$ haloalkyl, cyclopropyl, or cyclopropylmethyl.

Even more preferred compounds of formula II are those where, $X_1$ and Y are each $CR_C$, wherein each $R_C$ is independently hydrogen, halogen, methyl, ethyl, fluoromethyl, difluoromethyl, trifluoromethyl, cyclopropyl, or cyclopropylmethyl.

In a more preferred embodiment, the invention provides compounds of formula II where $R_5$ and $R_6$ are each independently hydrogen or $C_1$-$C_6$ alkyl.

In a more preferred embodiment, the invention provides compounds of formula II where $R_5$ and $R_6$ are each independently hydrogen or $C_1$-$C_3$ alkyl.

In another embodiment, the invention provides compounds of formula II wherein $R_5$ and $R_6$ together with the carbon to which they are attached form a 3-8 membered cycloalkyl or heterocycloalkyl ring.

In a preferred embodiment, the invention provides compounds of formula II wherein $R_5$ and $R_6$ together with the carbon to which they are attached form a 3- or 4-membered cycloalkyl.

In another embodiment, the invention provides compounds of formula IIa, (IIa)

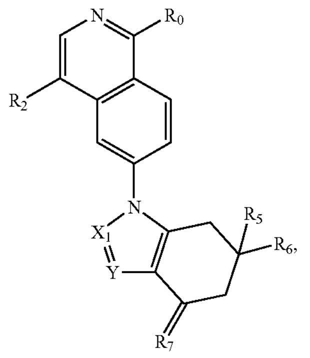

wherein $R_0$, $R_2$, $R_5$, $R_6$, $R_7$, $X_1$, and Y are as defined for formula I.

In another embodiment, the invention provides compounds of formula IIa where $R_7$ is O or N—OH.

More preferred compounds of formula IIa are those wherein $R_7$ is O.

In another embodiment, the invention provides compounds of formula IIa where $R_0$ is hydrogen, halogen, $C_1$-$C_3$ alkyl, or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a preferred embodiment, the invention provides compounds of formula IIa wherein $R_0$ is hydrogen, halogen, hydroxyl, $C_1$-$C_3$ alkyl, or -A-$R_{0'}$, wherein A is —N($R_{0'}$)—, —N($R_{0'}$)CO—, —N[C(O)$R_{0'}$]C(O)—, or —N($R_0$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula IIa where $R_0$ is hydroxyl.

In a more preferred embodiment, the invention provides compounds of formula IIa where $R_0$ is —N($R_{0'}$)$_2$—, —N($R_{0'}$)CO$R_0$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula IIa where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula IIa where $R_0$ is —N($R_{0'}$)$_2$—, and each $R_{0'}$ is independently hydrogen, $C_1$-$C_{10}$ haloalkyl, $C_1$-$C_{10}$ alkyl.

In a more preferred embodiment, the invention provides compounds of formula IIa where $R_0$ is —$NH_2$.

In a preferred embodiment, the invention provides compounds of formula IIa where $X_1$ is N.

In a preferred embodiment, the invention provides compounds of formula IIa where Y is N.

In a preferred embodiment, the invention provides compounds of formula IIa where $X_1$ is $CR_C$.

In a preferred embodiment, the invention provides compounds of formula IIa where Y is $CR_C$.

In a more preferred embodiment, the invention provides compounds of formula IIa where $X_1$ is N and Y is $CR_C$.

In a another embodiment, the invention provides compounds of formula IIa where, $X_1$ is N and Y is $CR_C$, wherein $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula II where $X_1$ is N and Y is $CR_C$, wherein $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl.

Even more preferred compounds of formula IIa are those where, $X_1$ is N and Y is $CR_C$, wherein $R_C$ is hydrogen, halogen, $C_1$-$C_3$ alkyl, $C_1$-$C_3$ haloalkyl, cyclopropyl, or cyclopropylmethyl.

Even more preferred compounds of formula IIa are those where, $X_1$ is N and Y is $CR_C$, wherein $R_C$ is independently hydrogen, halogen, methyl, ethyl, fluoromethyl, difluoromethyl, trifluoromethyl, cyclopropyl, or cyclopropylmethyl.

In another embodiment, more preferred compounds formula IIa are those where $X_1$ and Y are each $CR_C$, wherein each $R_C$ is independently hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

Even more preferred compounds of formula IIa are those where, $X_1$ and Y are each $CR_C$, wherein each $R_C$ is independently hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl.

Even more preferred compounds of formula IIa are those where, $X_1$ and Y are each $CR_C$, wherein each $R_C$ is independently hydrogen, halogen, $C_1$-$C_3$ alkyl, $C_1$-$C_3$ haloalkyl, cyclopropyl, or cyclopropylmethyl.

Even more preferred compounds of formula IIa are those where, $X_1$ and Y are each $CR_C$, wherein each $R_C$ is independently hydrogen, halogen, methyl, ethyl, fluoromethyl, difluoromethyl, trifluoromethyl, cyclopropyl, or cyclopropylmethyl.

In a more preferred embodiment, the invention provides compounds of formula IIa where $R_5$ and $R_6$ are each independently hydrogen or $C_1$-$C_6$ alkyl.

In a more preferred embodiment, the invention provides compounds of formula IIa where $R_5$ and $R_6$ are each independently hydrogen or $C_1$-$C_3$ alkyl.

In another embodiment, the invention provides compounds of formula IIa wherein $R_5$ and $R_6$ together with the carbon to which they are attached form a 3-8 membered cycloalkyl or heterocycloalkyl ring.

In a preferred embodiment, the invention provides compounds of formula IIa wherein $R_5$ and $R_6$ together with the carbon to which they are attached form a 3- or 4-membered cycloalkyl.

In another embodiment, the invention provides compounds of formula III,

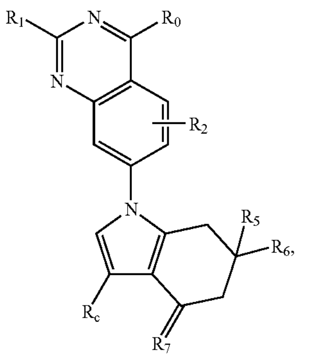

(III)

wherein $R_0$, $R_1$, $R_2$, $R_5$, $R_6$, $R_7$, and $R_C$ are as defined for formula I.

In another embodiment, the invention provides compounds of formula III where $R_7$ is O or N—OH. More preferred compounds of formula I are those wherein $R_7$ is O.

In another embodiment, the invention provides compounds of formula III where $R_0$ is hydrogen, halogen, $C_1$-$C_3$ alkyl, or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a preferred embodiment, the invention provides compounds of formula III wherein $R_0$ is hydrogen, halogen, hydroxyl, $C_1$-$C_3$ alkyl, or -A-$R_{0'}$, wherein A is —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula III where $R_0$ is hydroxyl.

In a more preferred embodiment, the invention provides compounds of formula III where $R_0$ is —N($R_{0'}$)$_2$—, —N($R_{0'}$)CO$R_{0'}$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula III where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula III where $R_0$ is —N($R_{0'}$)$_2$—, and each $R_{0'}$ is independently hydrogen, $C_1$-$C_{10}$ haloalkyl, $C_1$-$C_{10}$ alkyl.

In a more preferred embodiment, the invention provides compounds of formula III where $R_0$ is —$NH_2$.

In another more preferred embodiment, the invention provides compounds of formula III where $R_0$ is hydrogen, halogen, hydroxyl, $C_1$-$C_3$ alkyl.

In another embodiment, the invention provides compounds of formula III where $R_1$ is hydrogen, halogen, or —B—$R_{1'}$, wherein B is a bond, —O—, —N($R_{1'}$)—, —N($R_{1'}$)CO—, —N[C(O)$R_{1'}$]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula III where $R_1$ is hydrogen, halogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula III where $R_1$ is hydrogen, halogen, —OH, —$C_1$-$C_6$ alkoxy, —$C_1$-$C_6$ alkyl, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a another embodiment, the invention provides compounds of formula III where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula III where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula III where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula III where $R_C$ is hydrogen, halogen, methyl, ethyl, fluoromethyl, difluoromethyl, trifluoromethyl, cyclopropyl, or cyclopropylmethyl.

In a more preferred embodiment, the invention provides compounds of formula III where $R_5$ and $R_6$ are each independently hydrogen or $C_1$-$C_6$ alkyl.

In a more preferred embodiment, the invention provides compounds of formula III where $R_5$ and $R_6$ are each independently hydrogen or $C_1$-$C_3$ alkyl.

In another embodiment, the invention provides compounds of formula III wherein $R_5$ and $R_6$ together with the carbon to which they are attached form a 3-8 membered cycloalkyl or heterocycloalkyl ring.

In a preferred embodiment, the invention provides compounds of formula III wherein $R_5$ and $R_6$ together with the carbon to which they are attached form a 3- or 4-membered cycloalkyl.

In another embodiment, the invention provides compounds of formula IIIa, (IIIa)

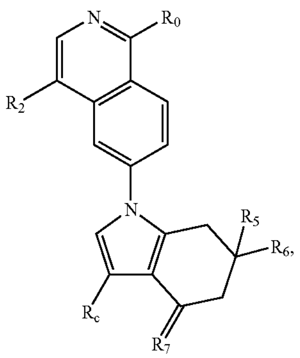

wherein $R_0$, $R_2$, $R_5$, $R_6$, $R_7$, and $R_C$ are as defined for formula I.

In another embodiment, the invention provides compounds of formula IIIa where $R_7$ is O or N—OH. More preferred compounds of formula I are those wherein $R_7$ is O.

In another embodiment, the invention provides compounds of formula IIIa where $R_0$ is hydrogen, halogen, $C_1$-$C_3$ alkyl, or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula IIIa wherein $R_0$ is hydrogen, halogen, hydroxyl, $C_1$-$C_3$ alkyl, or -A-$R_{0'}$, wherein A is —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula IIIa where $R_0$ is hydroxyl.

In a more preferred embodiment, the invention provides compounds of formula IIIa where $R_0$ is —N($R_{0'}$)$_2$—, —N($R_{0'}$)COR$_{0'}$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula IIIa where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula IIIa where $R_0$ is —N($R_{0'}$)$_2$—, and each $R_{0'}$ is independently hydrogen, $C_1$-$C_{10}$ haloalkyl, $C_1$-$C_{10}$ alkyl.

In a more preferred embodiment, the invention provides compounds of formula IIIa where $R_0$ is —$NH_2$.

In a another embodiment, the invention provides compounds of formula IIIa where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula IIIa where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula IIIa where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula IIIa where $R_C$ is hydrogen, halogen, methyl, ethyl, fluoromethyl, difluoromethyl, trifluoromethyl, cyclopropyl, or cyclopropylmethyl.

In a more preferred embodiment, the invention provides compounds of formula IIIa where $R_5$ and $R_6$ are each independently hydrogen or $C_1$-$C_6$ alkyl.

In a more preferred embodiment, the invention provides compounds of formula IIIa where $R_5$ and $R_6$ are each independently hydrogen or $C_1$-$C_3$ alkyl.

In another embodiment, the invention provides compounds of formula IIIa wherein $R_5$ and $R_6$ together with the carbon to which they are attached form a 3-8 membered cycloalkyl or heterocycloalkyl ring.

In a preferred embodiment, the invention provides compounds of formula IIIa wherein $R_5$ and $R_6$ together with the carbon to which they are attached form a 3- or 4-membered cycloalkyl.

In another embodiment, the invention provides compounds of formula IV,

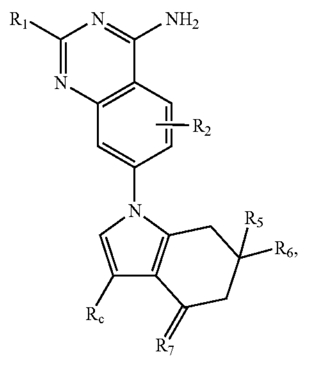

(IV)

wherein $R_1$, $R_2$, $R_5$, $R_6$, $R_7$, and $R_C$ are as defined for formula I.

In another embodiment, the invention provides compounds of formula IV where $R_7$ is O or N—OH. More preferred compounds of formula I are those wherein $R_7$ is O.

In another embodiment, the invention provides compounds of formula IV where $R_1$ is hydrogen, halogen, or —B—$R_{1'}$, wherein B is a bond, —O—, —N($R_{1'}$)—, —N($R_{1'}$)CO—, —N[C(O)$R_{1'}$]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula IV where $R_1$ is hydrogen, halogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula IV where $R_1$ is hydrogen, halogen, —OH, —$C_1$-$C_6$ alkoxy, $C_1$-$C_6$ alkyl, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a another embodiment, the invention provides compounds of formula IV where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula IV where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula IV where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula IV where $R_C$ is hydrogen, halogen, methyl, ethyl, fluoromethyl, difluoromethyl, trifluoromethyl, cyclopropyl, or cyclopropylmethyl.

In a more preferred embodiment, the invention provides compounds of formula IV where $R_5$ and $R_6$ are each independently hydrogen or $C_1$-$C_6$ alkyl.

In a more preferred embodiment, the invention provides compounds of formula IV where $R_5$ and $R_6$ are each independently hydrogen or $C_1$-$C_3$ alkyl.

In another embodiment, the invention provides compounds of formula IV wherein $R_5$ and $R_6$ together with the carbon to which they are attached form a 3-8 membered cycloalkyl or heterocycloalkyl ring.

In a preferred embodiment, the invention provides compounds of formula IV wherein $R_5$ and $R_6$ together with the carbon to which they are attached form a 3- or 4-membered cycloalkyl.

In another embodiment, the invention provides compounds of formula IVa, (IVa)

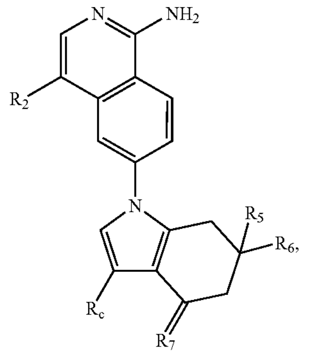

wherein $R_2$, $R_5$, $R_6$, $R_7$, and $R_C$ are as defined for formula I.

In another embodiment, the invention provides compounds of formula IVa where $R_7$ is O or N—OH. More preferred compounds of formula I are those wherein $R_7$ is O.

In a another embodiment, the invention provides compounds of formula IVa where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula IV where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula IVa where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula IVa where $R_C$ is hydrogen, halogen, methyl, ethyl, fluoromethyl, difluoromethyl, trifluoromethyl, cyclopropyl, or cyclopropylmethyl.

In a more preferred embodiment, the invention provides compounds of formula IVa where $R_5$ and $R_6$ are each independently hydrogen or $C_1$-$C_6$ alkyl.

In a more preferred embodiment, the invention provides compounds of formula IVa where $R_5$ and $R_6$ are each independently hydrogen or $C_1$-$C_3$ alkyl.

In another embodiment, the invention provides compounds of formula IVa wherein $R_5$ and $R_6$ together with the carbon to which they are attached form a 3-8 membered cycloalkyl or heterocycloalkyl ring.

In a preferred embodiment, the invention provides compounds of formula IVa wherein $R_5$ and $R_6$ together with the carbon to which they are attached form a 3- or 4-membered cycloalkyl.

In another embodiment, the invention provides compounds of formula IVb, (IVb)

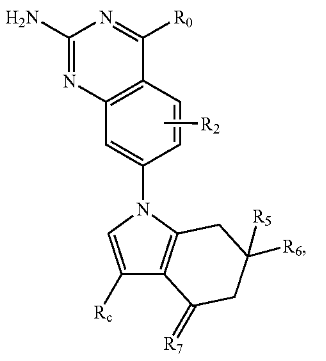

wherein $R_2$, $R_5$, $R_6$, $R_7$, and $R_C$ are as defined for formula I.

In another embodiment, the invention provides compounds of formula IVb where $R_0$ is hydrogen, halogen, $C_1$-$C_3$ alkyl, or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a preferred embodiment, the invention provides compounds of formula IVb wherein $R_0$ is hydrogen, halogen, hydroxyl, $C_1$-$C_3$ alkyl, or -A-$R_{0'}$, wherein A is —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula IVb where $R_0$ is hydroxyl.

In a more preferred embodiment, the invention provides compounds of formula IVb where $R_0$ is —N($R_{0'}$)$_2$—, —N($R_{0'}$)COR$_{0'}$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula IVb where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula IVb where $R_0$ is —N($R_{0'}$)$_2$—, and each $R_{0'}$ is independently hydrogen, $C_1$-$C_{10}$ haloalkyl, $C_1$-$C_{10}$ alkyl.

In a more preferred embodiment, the invention provides compounds of formula IVb where $R_0$ is —$NH_2$.

In another more preferred embodiment, the invention provides compounds of formula IVb where $R_0$ is hydrogen, halogen, hydroxyl, $C_1$-$C_3$ alkyl.

In another embodiment, the invention provides compounds of formula V, (V)

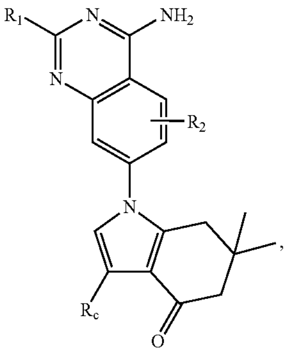

wherein $R_1$, $R_2$, and $R_C$ are as defined for formula I.

In another embodiment, the invention provides compounds of formula V where $R_1$ is hydrogen, halogen, or —B—$R_{1'}$, wherein B is a bond, —O—, —N($R_{1'}$)—, —N($R_{1'}$)CO—, —N[C(O)$R_{1'}$]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula V where $R_1$ is hydrogen, halogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula V where $R_1$ is hydrogen, halogen, —OH, —$C_1$-$C_6$ alkoxy, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a another embodiment, the invention provides compounds of formula V where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula V where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula V where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula V where $R_C$ is hydrogen, halogen, methyl, ethyl, fluoromethyl, difluoromethyl, trifluoromethyl, cyclopropyl, or cyclopropylmethyl; such compounds are referred to hereafter as compounds of formula Va.

In another embodiment, the invention provides compounds of formula Va, (Va)

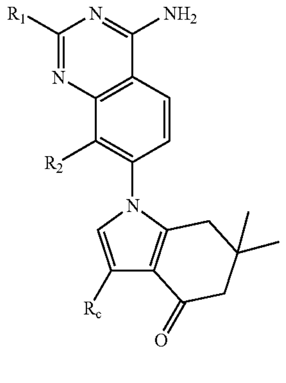

wherein $R_1$ is hydrogen, halogen, or —B—$R_{1'}$, wherein

B is a bond, —O—, —N($R_{1'}$)—, —N($R_{1'}$)CO—, —N[C(O)$R_{1'}$]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula Va where $R_1$ is hydrogen, halogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula Va where $R_1$ is hydrogen, halogen, —OH, —$C_1$-$C_6$ alkoxy, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In another embodiment, the invention provides compounds of formula Vb, (Vb)

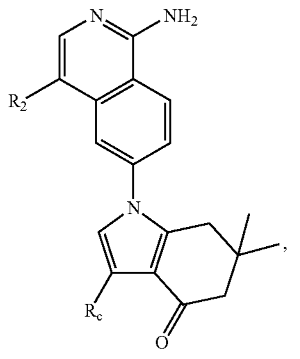

wherein $R_C$ is as defined for formula I.

In a another embodiment, the invention provides compounds of formula Vb where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula Vb where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula Vb where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula Vb where $R_C$ is hydrogen, halogen, methyl, ethyl, fluoromethyl, difluoromethyl, trifluoromethyl, cyclopropyl, or cyclopropylmethyl.

In another embodiment, the invention provides compounds of formula IVc, (IVc)

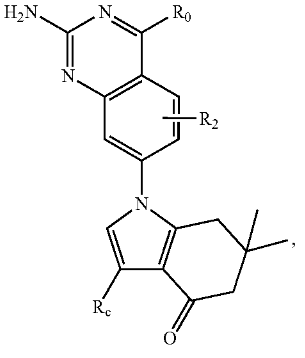

wherein $R_2$, $R_5$, $R_6$, $R_7$, and $R_C$ are as defined for formula I.

In another embodiment, the invention provides compounds of formula IVc where $R_0$ is hydrogen, halogen, $C_1$-$C_3$ alkyl, or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula IVc wherein $R_0$ is hydrogen, halogen, hydroxyl, $C_1$-$C_3$ alkyl, or -A-$R_{0'}$, wherein A is —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula IVc where $R_0$ is hydroxyl.

In a more preferred embodiment, the invention provides compounds of formula IVc where $R_0$ is —N($R_{0'}$)$_2$—, —N($R_{0'}$)COR$_{0'}$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula IVc where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula IVc where $R_0$ is —N($R_{0'}$)$_2$—, and each $R_{0'}$ is independently hydrogen, $C_1$-$C_{10}$ haloalkyl, $C_1$-$C_{10}$ alkyl.

In a more preferred embodiment, the invention provides compounds of formula IVc where $R_0$ is —$NH_2$.

In another more preferred embodiment, the invention provides compounds of formula IVc where $R_0$ is hydrogen, halogen, hydroxyl, $C_1$-$C_3$ alkyl.

In another embodiment, the invention provides compounds of formula VI, (VI)

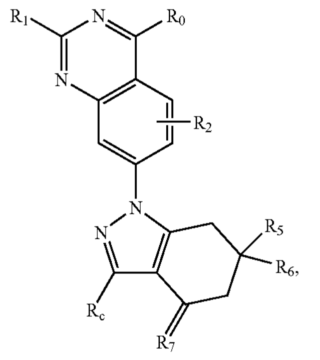

wherein $R_0$, $R_1$, $R_2$, $R_5$, $R_6$, $R_7$, and $R_C$ are as defined for formula I.

In another embodiment, the invention provides compounds of formula VI where $R_7$ is O or N—OH. More preferred compounds of formula I are those wherein $R_7$ is O.

In another embodiment, the invention provides compounds of formula VI where $R_0$ is hydrogen, halogen, $C_1$-$C_3$ alkyl or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a preferred embodiment, the invention provides compounds of formula VI wherein $R_0$ is hydrogen, halogen, hydroxyl, $C_1$-$C_3$ alkyl or -A-$R_{0'}$, wherein A is —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula VI where $R_0$ is hydroxyl.

In a more preferred embodiment, the invention provides compounds of formula VI where $R_0$ is —N($R_{0'}$)$_2$—, —N($R_{0'}$)COR$_0$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula VI where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula VI where $R_0$ is —N($R_{0'}$)$_2$—, and each $R_{0'}$ is independently hydrogen, $C_1$-$C_{10}$ haloalkyl, $C_1$-$C_{10}$ alkyl.

In a more preferred embodiment, the invention provides compounds of formula VI where $R_0$ is —$NH_2$.

In another more preferred embodiment, the invention provides compounds of formula VI where $R_0$ is hydrogen, halogen, hydroxyl, $C_1$-$C_3$ alkyl.

In another embodiment, the invention provides compounds of formula VI where $R_1$ is hydrogen, or —B—$R_{1'}$, wherein B is a bond, —O—, —N($R_{1'}$)—, —N($R_{1'}$)CO—, —N[C(O)$R_{1'}$]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula VI where $R_1$ is hydrogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a preferred embodiment, the invention provides compounds of formula VI where $R_1$ is hydrogen, —OH, —$C_1$-$C_6$alkoxy, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a another embodiment, the invention provides compounds of formula VI where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula VI where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula VI where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula VI where $R_C$ is hydrogen, halogen, methyl, ethyl, fluoromethyl, difluoromethyl, trifluoromethyl, cyclopropyl, or cyclopropylmethyl.

In a more preferred embodiment, the invention provides compounds of formula VI where $R_5$ and $R_6$ are each independently hydrogen or $C_1$-$C_6$ alkyl.

In a more preferred embodiment, the invention provides compounds of formula VI where $R_5$ and $R_6$ are each independently hydrogen or $C_1$-$C_3$ alkyl.

In another embodiment, the invention provides compounds of formula VI wherein $R_5$ and $R_6$ together with the carbon to which they are attached form a 3-8 membered cycloalkyl or heterocycloalkyl ring.

In a preferred embodiment, the invention provides compounds of formula VI wherein $R_5$ and $R_6$ together with the carbon to which they are attached form a 3- or 4-membered cycloalkyl.

In another embodiment, the invention provides compounds of formula VIa, (VIa)

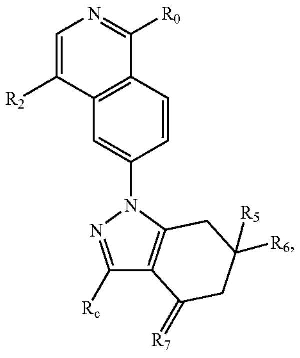

wherein $R_0$, $R_2$, $R_5$, $R_6$, $R_7$, and $R_C$ are as defined for formula I.

In another embodiment, the invention provides compounds of formula VIa where $R_7$ is O or N—OH. More preferred compounds of formula I are those wherein $R_7$ is O.

In another embodiment, the invention provides compounds of formula VIa where $R_0$ is hydrogen, halogen, or -A-$R_{0'}$, wherein A is —O—, —N($R_{0'}$)—, —N($R_{0'}$)CO—, —N[C(O) $R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula VIa wherein $R_0$ is hydrogen, halogen, hydroxyl, or -A-$R_{0'}$, wherein A is —N($R_{0'}$)—, —N($R_{0'}$)CO—, —N[C(O)$R_{0'}$]C(O)—, or —N($R_0$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula VIa where $R_0$ is hydroxyl.

In a more preferred embodiment, the invention provides compounds of formula VIa where $R_0$ is —N($R_{0'}$)$_2$—, —N($R_{0'}$)COR$_{0'}$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula VIa where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula VIa where $R_0$ is —N($R_{0'}$)$_2$—, and each $R_{0'}$ is independently hydrogen, $C_1$-$C_{10}$ haloalkyl, $C_1$-$C_{10}$ alkyl.

In a more preferred embodiment, the invention provides compounds of formula VIa where $R_0$ is —$NH_2$.

In a another embodiment, the invention provides compounds of formula VI where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula VIa where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula VIa where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula VIa where $R_C$ is hydrogen, halogen, methyl, ethyl, fluoromethyl, difluoromethyl, trifluoromethyl, cyclopropyl, or cyclopropylmethyl.

In a more preferred embodiment, the invention provides compounds of formula VIa where $R_5$ and $R_6$ are each independently hydrogen or $C_1$-$C_6$ alkyl.

In a more preferred embodiment, the invention provides compounds of formula VIa where $R_5$ and $R_6$ are each independently hydrogen or $C_1$-$C_3$ alkyl.

In another embodiment, the invention provides compounds of formula VIa wherein $R_5$ and $R_6$ together with the carbon to which they are attached form a 3-8 membered cycloalkyl or heterocycloalkyl ring.

In a preferred embodiment, the invention provides compounds of formula VIa wherein $R_5$ and $R_6$ together with the carbon to which they are attached form a 3- or 4-membered cycloalkyl.

In another embodiment, the invention provides compounds of formula VII, (VII)

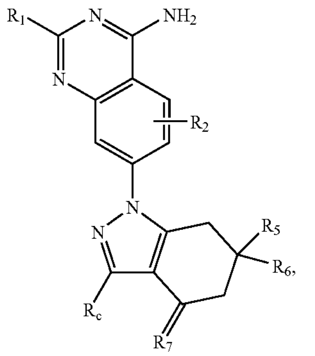

wherein $R_1$, $R_2$, $R_5$, $R_6$, $R_7$, and $R_C$ are as defined for formula I.

In another embodiment, the invention provides compounds of formula VII where $R_7$ is O or N—OH. More preferred compounds of formula I are those wherein $R_7$ is O.

In another embodiment, the invention provides compounds of formula VII where $R_1$ is hydrogen, or —B—$R_{1'}$, wherein B is a bond, —O—, —N($R_{1'}$)—, —N($R_{1'}$)CO—, —N[C(O)$R_{1'}$]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula VII where $R_1$ is hydrogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula VII where $R_1$ is hydrogen, —OH, —$C_1$-$C_6$alkoxy, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a another embodiment, the invention provides compounds of formula VII where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula VII where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula VII where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula VII where $R_C$ is hydrogen, halogen, methyl, ethyl, fluoromethyl, difluoromethyl, trifluoromethyl, cyclopropyl, or cyclopropylmethyl.

In a more preferred embodiment, the invention provides compounds of formula VII where $R_5$ and $R_6$ are each independently hydrogen or $C_1$-$C_6$ alkyl.

In a more preferred embodiment, the invention provides compounds of formula VII where $R_5$ and $R_6$ are each independently hydrogen or $C_1$-$C_3$ alkyl.

In another embodiment, the invention provides compounds of formula VII wherein $R_5$ and $R_6$ together with the carbon to which they are attached form a 3-8 membered cycloalkyl or heterocycloalkyl ring.

In a preferred embodiment, the invention provides compounds of formula VII wherein $R_5$ and $R_6$ together with the carbon to which they are attached form a 3- or 4-membered cycloalkyl.

In another embodiment, the invention provides compounds of formula VIb, (VIb)

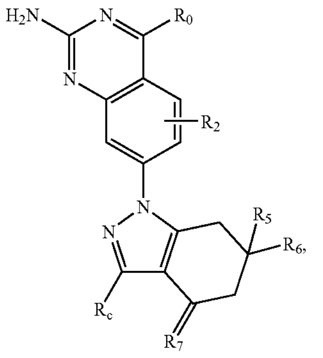

wherein $R_2$, $R_5$, $R_6$, $R_7$, and $R_C$ are as defined for formula I.

In another embodiment, the invention provides compounds of formula VIb where $R_0$ is hydrogen, halogen, $C_1$-$C_3$ alkyl or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a preferred embodiment, the invention provides compounds of formula VIb wherein $R_0$ is hydrogen, halogen, hydroxyl, $C_1$-$C_3$ alkyl or -A-$R_{0'}$, wherein A is —N($R_{0'}$)—, —N($R_{0'}$)CO—, —N[C(O)$R_{0'}$]C(O)—, or —N($R_0$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula VIb where $R_0$ is hydroxyl.

In a more preferred embodiment, the invention provides compounds of formula VIb where $R_0$ is —N($R_{0'}$)$_2$—, —N($R_{0'}$)CO$R_{0'}$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula VIb where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In a more preferred embodiment, the invention provides compounds of formula VIb where $R_0$ is —N($R_{0'}$)$_2$—, and each $R_{0'}$ is independently hydrogen, $C_1$-$C_{10}$ haloalkyl, $C_1$-$C_{10}$ alkyl.

In a more preferred embodiment, the invention provides compounds of formula VIb where $R_0$ is —$NH_2$.

In another more preferred embodiment, the invention provides compounds of formula VIb where $R_0$ is hydrogen, halogen, hydroxyl, $C_1$-$C_3$ alkyl.

In another embodiment, the invention provides compounds of formula VIIa, (VIIa)

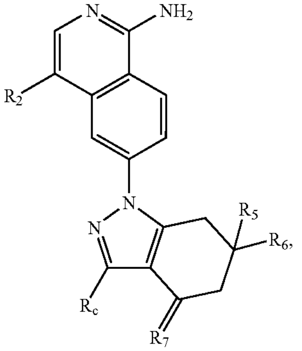

wherein $R_5$, $R_6$, $R_7$, and $R_C$ are as defined for formula I.

In another embodiment, the invention provides compounds of formula VIIa where $R_7$ is O or N—OH. More preferred compounds of formula I are those wherein $R_7$ is O.

In a another embodiment, the invention provides compounds of formula VIIa where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula VIIa where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula VIIa where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula VIIa where $R_C$ is hydrogen, halogen, methyl, ethyl, fluoromethyl, difluoromethyl, trifluoromethyl, cyclopropyl, or cyclopropylmethyl.

In a more preferred embodiment, the invention provides compounds of formula VIIa where $R_5$ and $R_6$ are each independently hydrogen or $C_1$-$C_6$ alkyl.

In a more preferred embodiment, the invention provides compounds of formula VIIa where $R_5$ and $R_6$ are each independently hydrogen or $C_1$-$C_3$ alkyl.

In another embodiment, the invention provides compounds of formula VIIa wherein $R_5$ and $R_6$ together with the carbon to which they are attached form a 3-8 membered cycloalkyl or heterocycloalkyl ring.

In a preferred embodiment, the invention provides compounds of formula VIIa wherein $R_5$ and $R_6$ together with the carbon to which they are attached form a 3- or 4-membered cycloalkyl.

In another embodiment, the invention provides compounds of formula VIII, (VIII)

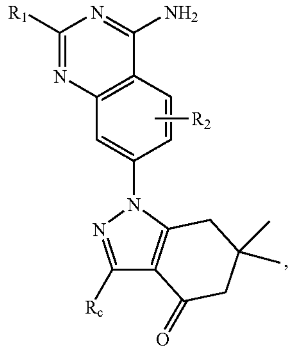

wherein $R_1$, $R_2$, and $R_C$ are as defined for formula I.

In another embodiment, the invention provides compounds of formula VIII where $R_1$ is hydrogen, or —B—$R_{1'}$, wherein B is a bond, —O—, —N($R_{1'}$)—, —N($R_{1'}$)CO—, —N[C(O)$R_{1'}$]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula VIII where $R_1$ is hydrogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula VIII where $R_1$ is hydrogen, —OH, —$C_1$-$C_6$alkoxy, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a another embodiment, the invention provides compounds of formula VIII where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula VIII where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula VIII where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula VIII where $R_C$ is hydrogen, halogen, methyl, ethyl, fluoromethyl, difluoromethyl, trifluoromethyl, cyclopropyl, or cyclopropylmethyl; such compounds are referred to hereafter as compounds of formula VIIIa.

In another embodiment, the invention provides compounds of formula VIIIa, wherein $R_1$ is hydrogen, or —B—$R_{1'}$, wherein B is a bond, —O—, —N($R_{1'}$)—, —N($R_{1'}$)CO—, —N[C(O)$R_{1'}$]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula VIIIa where $R_1$ is hydrogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula VIIIa where $R_1$ is hydrogen, —OH, —$C_1$-$C_6$alkoxy, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In another embodiment, the invention provides compounds of formula VIc, (VIc)

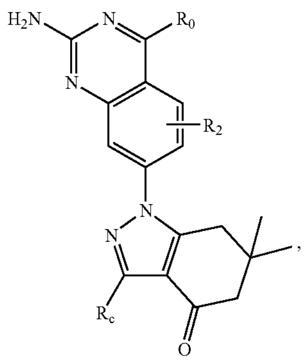

wherein $R_2$, $R_5$, $R_6$, $R_7$, and $R_C$ are as defined for formula I.

In another embodiment, the invention provides compounds of formula VIc where $R_0$ is hydrogen, halogen, $C_1$-$C_3$ alkyl or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a preferred embodiment, the invention provides compounds of formula VIc wherein $R_0$ is hydrogen, halogen, hydroxyl, $C_1$-$C_3$ alkyl or -A-$R_{0'}$, wherein A is —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula VIc where $R_0$ is hydroxyl.

In a more preferred embodiment, the invention provides compounds of formula VIc where $R_0$ is —N($R_{0'}$)$_2$—, —N($R_{0'}$)COR$_{0'}$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula VIc where $R_0$ is —$N(R_{0'})_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

In a more preferred embodiment, the invention provides compounds of formula VIc where $R_0$ is —$N(R_{0'})_2$—, and each $R_{0'}$ is independently hydrogen, $C_1$-$C_{10}$ haloalkyl, $C_1$-$C_{10}$ alkyl.

In a more preferred embodiment, the invention provides compounds of formula VIc where $R_0$ is —$NH_2$.

In another more preferred embodiment, the invention provides compounds of formula VIc where $R_0$ is hydrogen, halogen, hydroxyl, $C_1$-$C_3$ alkyl.

In another embodiment, the invention provides compounds of formula VIIIb, (VIIIb)

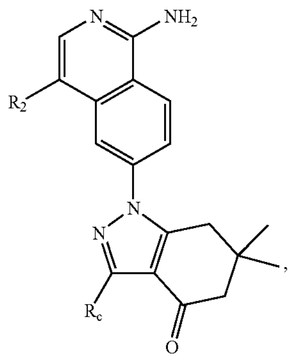

wherein $R_C$ is as defined for formula I.

In a another embodiment, the invention provides compounds of formula VIIIb where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

In a preferred embodiment, the invention provides compounds of formula VIIIb where $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

In a preferred embodiment, the invention provides compounds of formula VIIIb where $R_C$ is hydrogen, halogen, $C_1$-$C_3$ alkyl, $C_1$-$C_3$ haloalkyl, cyclopropyl, or cyclopropylmethyl.

In a preferred embodiment, the invention provides compounds of formula VIIIb where $R_C$ is hydrogen, halogen, methyl, ethyl, fluoromethyl, difluoromethyl, trifluoromethyl, cyclopropyl, or cyclopropylmethyl.

In another embodiment, the invention provides compounds of formula IX,

IX

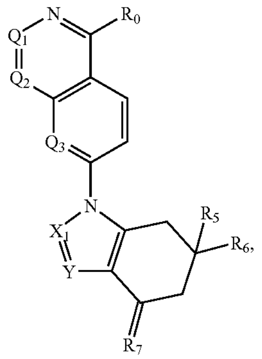

wherein $R_0$, $R_5$, $R_6$, $R_7$, $Q_1$, $Q_2$, $Q_3$, $X_1$, and Y are defined as in formula I.

Preferred compounds of formula IX include those where $R_7$ is O or N—OH. More preferred compounds of formula IX are those wherein $R_7$ is O.

Other preferred compounds of formula IX are those where $R_0$ is hydrogen, halogen, $C_1$-$C_3$ alkyl, or -A-$R_{0'}$, wherein A is —O—, —$N(R_{0'})$—, —$N(R_{0'})CO$—, —$N[C(O)R_{0'}]C(O)$—, or —$N(R_{0'})SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

More preferred compounds of formula IX are those wherein $R_0$ is hydrogen, halogen, hydroxyl, $C_1$-$C_3$ alkyl, or -A-$R_{0'}$, wherein A is —$N(R_{0'})$—, —$N(R_{0'})CO$—, —$N[C(O)R_{0'}]C(O)$—, or —$N(R_0)SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

Even more preferred compounds of formula IX are those where $R_0$ is hydroxyl. Other even more preferred compounds of formula IX are those where $R_0$ is —$N(R_{0'})_2$—, —$N(R_{0'})COR_{0'}$, —$N[C(O)R_{0'}]C(O)$—, or —$N(R_{0'})SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

Other even more preferred compounds of formula IX are those where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

Other even more preferred compounds of formula IX are those where $R_0$ is —N($R_{0'}$)$_2$—, and each $R_{0'}$ is independently hydrogen, $C_1$-$C_{10}$ haloalkyl, $C_1$-$C_{10}$ alkyl.

Other even more preferred compounds of formula IX are those where $R_0$ is —$NH_2$.

Other even more preferred compounds of formula IX are those wherein $R_0$ is hydrogen, halogen, hydroxyl, or $C_1$-$C_3$ alkyl.

Other preferred compounds of formula IX are those where $Q_1$ is $CR_1$ and $Q_2$ is N.

Other preferred compounds of formula IX are those where $Q_1$ is $CR_1$ and $Q_2$ is N, wherein $R_1$ is hydrogen, halogen, or —B—$R_{1'}$, wherein B is a bond, —O—, —N($R_{1'}$)—, —N($R_{1'}$)CO—, —N[C(O)$R_{1'}$]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$) alkylamino, cyano, nitro, halo($C_1$-$C_6$) alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

More preferred compounds of formula IX are those where $Q_1$ is $CR_1$ and $Q_2$ is N, wherein $R_1$ is hydrogen, halogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

More preferred compounds of formula IX are those where $Q_1$ is $CR_1$ and $Q_2$ is N, wherein $R_1$ is hydrogen, halogen, —OH, —$C_1$-$C_6$alkoxy, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

Other preferred compounds of formula IX are those where $Q_3$ is N.

Other preferred compounds of formula IX are those where $Q_3$ is $CR_2$. More preferred compounds of formula IX are those where $Q_3$ is $CR_2$, wherein each $R_2$ is independently (a) H, (b) halogen, or (c) a $C_1$-$C_{15}$ alkyl group wherein each (c) is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono($C_1$-$C_{10}$)alkylamino, or di($C_1$-$C_{10}$)alkylamino.

More preferred compounds of formula IX are those where $Q_3$ is $CR_2$, wherein each $R_2$ is independently H, halogen, or $C_1$-$C_{15}$ alkyl. More preferred compounds of formula IX are those where $Q_3$ is $CR_2$, wherein each $R_2$ is independently H or halogen.

Other preferred compounds of formula IX are those where $X_1$ is N.

Other preferred compounds of formula IX are those where Y is N.

Other preferred compounds of formula IX are those where $X_1$ is $CR_C$.

Other preferred compounds of formula IX are those where Y is $CR_C$.

More preferred embodiments of formula IX are those compounds where $X_1$ is N and Y is $CR_C$. Even more preferred compounds of formula IX are those where, $X_1$ is N and Y is $CR_C$, wherein $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

Even more preferred compounds of formula IX are those where, $X_1$ is N and Y is $CR_C$, wherein $R_C$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

Even more preferred compounds of formula IX are those where, $X_1$ is N and Y is $CR_C$, wherein $R_C$ is hydrogen, halogen, $C_1$-$C_3$ alkyl, $C_1$-$C_3$ haloalkyl, cyclooproyl, or cyclopropylmethyl.

Even more preferred compounds of formula IX are those where, $X_1$ is N and Y is $CR_C$, wherein $R_C$ is independently hydrogen, halogen, methyl, ethyl, fluoromethyl, difluoromethyl, trifluoromethyl, cyclopropyl, or cyclopropylmethyl.

In another embodiment, more preferred compounds formula IX are those where $X_1$ and Y are each $CR_C$, wherein each $R_C$ is independently hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl, wherein each alkyl or cycloalkyl is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

Even more preferred compounds of formula IX are those where, $X_1$ and Y are each $CR_C$, wherein each $R_C$ is independently hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1$-$C_{10}$)alkyl.

Even more preferred compounds of formula IX are those where, $X_1$ and Y are each $CR_C$, wherein each $R_C$ is independently hydrogen, halogen, $C_1$-$C_3$ alkyl, $C_1$-$C_3$ haloalkyl, cyclopropyl, or cyclopropylmethyl.

Even more preferred compounds of formula IX are those where, $X_1$ and Y are each $CR_C$, wherein each $R_C$ is independently hydrogen, halogen, methyl, ethyl, fluoromethyl, difluoromethyl, trifluoromethyl, cyclopropyl, or cyclopropylmethyl.

In another embodiment, the invention provides compounds of formula IX wherein $R_5$ and $R_6$ are each independently hydrogen or $C_1$-$C_6$ alkyl. In a preferred embodiment, the invention provides compounds of formula IX where $R_5$ and $R_6$ are each independently hydrogen or $C_1$-$C_3$ alkyl.

In another embodiment, the invention provides compounds of formula IX wherein $R_5$ and $R_6$ together with the carbon to which they are attached form a 3-8 membered cycloalkyl or heterocycloalkyl ring.

In a preferred embodiment, the invention provides compounds of formula IX wherein $R_5$ and $R_6$ together with the carbon to which they are attached form a 3- or 4-membered cycloalkyl.

The invention also provides intermediate compounds of formula X,

X

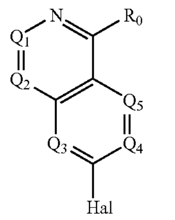

wherein

Hal is halogen;

$R_0$ is hydrogen, halogen, cyano, nitro, or -A-$R_{0'}$, wherein

A is a bond, —O—, —S—, —N($R_{0'}$)—, —N($R_{0'}$)CO—, —N[C(O)$R_{0'}$]C(O)—, —N($R_{0'}$)$SO_2$—, —$SO_2$N($R_{0'}$)—, —$SO_2$—, —CO—, —$CO_2$— or —C(O)N($R_{0'}$)—; and each $R_{0'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide;

$Q_1$ and $Q_2$ are each independently N or $CR_1$, wherein each $R_1$ is hydrogen, halogen, cyano, nitro, or —B—$R_{1'}$, wherein B is a bond, —O—, —S—, —N($R_{1'}$)—, —N($R_{1'}$)CO—, —N[C(O)$R_{1'}$]C(O)—, —N($R_{1'}$)$SO_2$, —$SO_2$N($R_{1'}$)—, —$SO_2$—, —CO—, —$CO_2$—, or —C(O)N($R_{1'}$)—; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide;

$Q_3$, $Q_4$, and $Q_5$ are each independently N or $CR_2$, wherein each $R_2$ is independently (a) H, (b) halogen, or (c) a $C_1$-$C_{15}$ alkyl group where up to five of the carbon atoms in said alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{22}$ is (i) heteroaryl, (ii) aryl, (iii) saturated or unsaturated $C_3$-$C_{10}$ cycloalkyl, or (iv) saturated or unsaturated $C_2$-$C_{10}$ heterocycloalkyl, wherein each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$)alkyl, —$SO_2$—($C_1$-$C_6$)alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, ($C_1$-$C_6$)alkoxy, or mono- or di-($C_1$-$C_{10}$)alkylamino; and each $R_{22}$ is optionally fused to a $C_6$-$C_{10}$ aryl group, $C_5$-$C_8$ saturated cyclic group, or a $C_5$-$C_{10}$ heterocycloalkyl group;

wherein each (c) is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, or $R_{23}$, wherein $R_{23}$ is (1) heteroaryl, (2) aryl, (3) saturated or unsaturated $C_5$-$C_{10}$ cycloalkyl, or (4) saturated or unsaturated $C_5$-$C_{10}$ heterocycloalkyl, and the $R_{23}$ groups are optionally substituted at least one group which is independently hydroxy, oxo, halo, amino, cyano, nitro, —SH, —S—($C_1$-$C_6$)alkyl, —$SO_2$—($C_1$-$C_6$)alkyl, —$SO_2$-aryl, —SO—($C_1$-$C_6$)alkyl, —SO-aryl, —$SO_2NH_2$, —$SO_2NH$—($C_1$-$C_6$)alkyl, —$SO_2NH$-aryl, ($C_1$-$C_6$)alkoxy, or mono- or di-($C_1$-$C_{10}$)alkylamino;

provided that (i) one and only one of $Q_1$ and $Q_2$ is N; and (ii) one and only one of $Q_3$, $Q_4$ and $Q_5$ is N.

Preferred compounds of formula X are those where $R_0$ is hydrogen, halogen, $C_1$-$C_3$ alkyl, or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

More preferred compounds of formula X are those wherein $R_0$ is hydrogen, halogen, hydroxyl, $C_1$-$C_3$ alkyl, or -A-$R_{0'}$, wherein A is —N($R_{0'}$)—, —N($R_{0'}$)CO—, —N[C(O)$R_{0'}$]C(O)—, or —N($R_0$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

Even more preferred compounds of formula X are those where $R_0$ is hydroxyl. Other even more preferred compounds of formula X are those where $R_0$ is —N($R_{0'}$)$_2$—, —N($R_{0'}$)COR$_{0'}$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

Other even more preferred compounds of formula X are those where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

Other even more preferred compounds of formula X are those where $R_0$ is —N($R_{0'}$)$_2$—, and each $R_{0'}$ is independently hydrogen, $C_1$-$C_{10}$ haloalkyl, $C_1$-$C_{10}$ alkyl.

Other even more preferred compounds of formula X are those where $R_0$ is —$NH_2$.

Other even more preferred compounds of formula X are those where $R_0$ is hydrogen, halogen, hydroxyl, $C_1$-$C_3$ alkyl.

Other preferred compounds of formula X are those where $Q_1$ is $CR_1$ and $Q_2$ is N.

Other preferred compounds of formula X are those where $Q_1$ is $CR_1$ and $Q_2$ is N, wherein $R_1$ is hydrogen, halogen, or —B—$R_{1'}$, wherein B is a bond, —O—, —N($R_1$)—, —N($R_{1'}$)CO—, —N[C(O)$R_{1'}$W]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$) alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

More preferred compounds of formula X are those where $Q_1$ is $CR_1$ and $Q_2$ is N, wherein $R_1$ is hydrogen, halogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

More preferred compounds of formula X are those where $Q_1$ is $CR_1$ and $Q_2$ is N, wherein $R_1$ is hydrogen, halogen, —OH, —$C_1$-$C_6$ alkoxy, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

Other preferred compounds of formula X are those where $Q_3$, $Q_4$, and $Q_5$ are $CR_2$. More preferred compounds of formula X are those where $Q_3$, $Q_4$, and $Q_5$ are $CR_2$, wherein each $R_2$ is independently (a) H, (b) halogen, or (c) a $C_1$-$C_{15}$ alkyl group wherein each (c) is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono($C_1$-$C_{10}$)alkylamino, or di($C_1$-$C_{10}$)alkylamino.

More preferred compounds of formula X are those where $Q_3$, $Q_4$, and $Q_5$ are $CR_2$, wherein each $R_2$ is independently H, halogen, or $C_1$-$C_{15}$ alkyl. More preferred compounds of formula X are those where $Q_3$, $Q_4$, and $Q_5$ are $CR_2$, wherein each $R_2$ is independently H or halogen.

Other preferred compounds of formula X are those where $Q_3$ is N. More preferred compounds of formula X are those where $Q_3$ is N and $Q_4$ and $Q_5$ are $CR_2$. More preferred compounds of formula X are those where $Q_3$ is N and $Q_4$ and $Q_5$ are $CR_2$, wherein each $R_2$ is independently H, halogen, or $C_1$-$C_{15}$ alkyl. More preferred compounds of formula X are those where $Q_3$ is N and $Q_4$ and $Q_5$ are $CR_2$, wherein each $R_2$ is independently H or halogen In another embodiment, the invention provide compounds according to formula X, wherein Hal is F, Cl, or Br. In a preferred embodiment, the invention provides compounds according to formula X, wherein Hal is F or Cl. In a more preferred embodiment, the invention provides compounds according to formula X, wherein Hal is —F.

The invention also provides intermediate compounds of formula XI,

XI

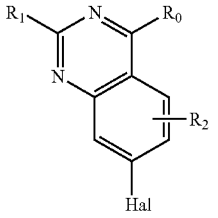

wherein

Hal is halogen;

and $R_0$, $R_1$, and $R_2$ are as defined for formula I.

Preferred compounds of formula XI are those where $R_0$ is hydrogen, halogen, —$C_1$-$C_3$ alkyl, or -A-$R_{0'}$, wherein A is —O—, —N($R_{0'}$)—, —N($R_{0'}$)CO—, —N[C(O)$R_{0'}$]C(O)—, or —N($R_{0'}$) $SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

More preferred compounds of formula XI are those wherein $R_0$ is hydrogen, halogen, hydroxyl, —$C_1$-$C_3$ alkyl, or -A-$R_{0'}$, wherein A is —N($R_{0'}$)—, —N($R_{0'}$)CO—, —N[C(O)$R_{0'}$]C(O)—, or —N($R_0$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

Even more preferred compounds of formula XI are those where $R_0$ is hydroxyl. Other even more preferred compounds of formula XI are those where $R_0$ is —N($R_{0'}$)$_2$—, —N($R_{0'}$)COR$_{0'}$, —N[C(O)$R_{0'}$]C(O)—, or —N($R_0$) $SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

Other even more preferred compounds of formula XI are those where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

Other even more preferred compounds of formula XI are those where $R_0$ is —N($R_{0'}$)$_2$—, and each $R_{0'}$ is independently hydrogen, $C_1$-$C_{10}$ haloalkyl, $C_1$-$C_{10}$ alkyl.

Other even more preferred compounds of formula XI are those where $R_0$ is —$NH_2$ Other even more preferred compounds of formula XI are those where $R_0$ is hydrogen, halogen, hydroxyl, or —$C_1$-$C_3$ alkyl.

Other preferred compounds of formula XI are those wherein $R_1$ is hydrogen, halogen, or —B—$R_{1'}$, wherein B is a bond, —O—, —N(R)—, —N($R_{1'}$)CO—, —N[C(O)$R_{1'}$]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

More preferred compounds of formula XI are those wherein $R_1$ is hydrogen, halogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

More preferred compounds of formula XI are those wherein $R_1$ is hydrogen, halogen, —OH, —$C_1$-$C_6$alkoxy, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

In another embodiment, the invention provide compounds according to formula XI, wherein Hal is F, Cl, or Br. In a preferred embodiment, the invention provides compounds according to formula XI, wherein Hal is F or Cl. In a more preferred embodiment, the invention provides compounds according to formula XI, wherein Hal is —F; such compounds are referred to hereafter as compounds of formula XIa.

Preferred compounds of formula XIa are those where $R_0$ is hydrogen, halogen, $C_1$-$C_3$ alkyl, or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

More preferred compounds of formula XIa are those wherein $R_0$ is hydrogen, halogen, hydroxyl, $C_1$-$C_3$ alkyl, or -A-$R_{0'}$, wherein A is —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

Even more preferred compounds of formula XIa are those where $R_0$ is hydroxyl. Other even more preferred compounds of formula XIa are those where $R_0$ is —N($R_{0'}$)$_2$—, —N($R_{0'}$)COR$_{0'}$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

Other even more preferred compounds of formula XIa are those where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

Other even more preferred compounds of formula XIa are those where $R_0$ is —N($R_{0'}$)$_2$—, and each $R_{0'}$ is independently hydrogen, $C_1$-$C_{10}$ haloalkyl, $C_1$-$C_{10}$ alkyl.

Other even more preferred compounds of formula XIa are those where $R_0$ is —$NH_2$.

Other even more preferred compounds of formula XIa are those where $R_0$ is hydrogen, halogen, hydroxyl, or $C_1$-$C_3$ alkyl.

Other preferred compounds of formula XIa are those wherein $R_1$ is hydrogen, halogen, or —B—$R_{1'}$, wherein B is a bond, —O—, —N($R_{1'}$)—, —N($R_{1'}$)CO—, —N[C(O)$R_{1'}$]C(O)—, —N($R_{1'}$)$SO_2$; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$) alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide.

More preferred compounds of formula XIa are those wherein $R_1$ is hydrogen, halogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

More preferred compounds of formula XIa are those wherein $R_1$ is hydrogen, halogen, —OH, —$C_1$-$C_6$ alkoxy, or —B—$R_{1'}$, wherein B is a bond, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

The invention also provides intermediate compounds of formula XIb,

XIb

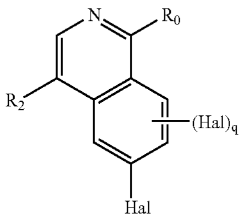

wherein

Each Hal is halogen; q is 0 or 1;

and $R_0$ is as defined for formula I.

Preferred compounds of formula XI are those where $R_0$ is hydrogen, halogen, $C_1$-$C_3$ alkyl, or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

More preferred compounds of formula XI are those wherein $R_0$ is hydrogen, halogen, hydroxyl, $C_1$-$C_3$ alkyl, or -A-$R_{0'}$, wherein A is —N($R_{0'}$)—, —N($R_{0'}$)CO—, —N[C(O)$R_{0'}$]C(O)—, or —N($R_0$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

Even more preferred compounds of formula XI are those where $R_0$ is hydroxyl. Other even more preferred compounds of formula XI are those where $R_0$ is —N($R_{0'}$)$_2$, —N($R_{0'}$)COR$_{0'}$, —N[C(O)$R_{0'}$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

Other even more preferred compounds of formula XI are those where $R_0$ is —N($R_{0'}$)$_2$, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo ($C_1$-$C_6$)alkyl, halo($C_1$-$C_6$)alkoxy, carboxamide, heterocycloalkyl, aryl, or heteroaryl.

Other even more preferred compounds of formula XI are those where $R_0$ is —N($R_{0'}$)$_2$, and each $R_{0'}$ is independently hydrogen, $C_1$-$C_{10}$ haloalkyl, $C_1$-$C_{10}$ alkyl.

Other even more preferred compounds of formula XI are those where $R_0$ is —$NH_2$.

Other even more preferred compounds of formula XI are those where $R_0$ is hydrogen, halogen, hydroxyl, $C_1$-$C_3$ alkyl.

In another embodiment, the invention provide compounds according to formula XI, wherein Hal is F, Cl, or Br. In a preferred embodiment, the invention provides compounds according to formula XI, wherein Hal is F or Cl. In a more preferred embodiment, the invention provides compounds according to formula XI, wherein Hal is —F; such compounds are referred to hereafter as compounds of formula XIc.

Preferred compounds of formula XIc are those where $R_0$ is hydrogen, halogen, $C_1$-$C_3$ alkyl, or -A-$R_{0'}$, wherein A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

More preferred compounds of formula XIc are those wherein $R_0$ is hydrogen, halogen, hydroxyl, $C_1$-$C_3$ alkyl, or -A-$R_{0'}$, wherein A is —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

Even more preferred compounds of formula XIc are those where $R_0$ is hydroxyl. Other even more preferred compounds of formula XIa are those where $R_0$ is —N($R_{0'}$)$_2$—, —N($R_{0'}$)COR$_{0'}$, —N[C(O)$R_0$]C(O)—, or —N($R_{0'}$)$SO_2R_{0'}$; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

Other even more preferred compounds of formula XIc are those where $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl.

Other even more preferred compounds of formula XIc are those where $R_0$ is —N($R_{0'}$)$_2$—, and each $R_{0'}$ is independently hydrogen, $C_1$-$C_{10}$ haloalkyl, $C_1$-$C_{10}$ alkyl.

Other even more preferred compounds of formula XIc are those where $R_0$ is —$NH_2$.

In a second aspect, the invention encompasses a method of treating cancer comprising administering to a patient in need thereof, a pharmaceutically acceptable amount of a compound or salt of any of Formulas I-IX or a pharmaceutical composition comprising a compound or salt of Formula I.

In a preferred embodiment of the second aspect, the invention encompasses a method of treating cancer comprising administering to a patient in need thereof, a pharmaceutically acceptable amount of a compound or salt of Formula I or a pharmaceutical composition comprising a compound or salt of Formula I.

In a third aspect, the invention encompasses the use of a therapeutically effective amount of a compound or salt of any of Formulas I-IX for the preparation of a medicament for the treatment of cancer, inflammation, or arthritis in a patient in need of such treatment.

In a preferred embodiment of the third aspect, the invention encompasses the use of a therapeutically effective amount of a compound or salt of Formula I for the preparation of a medicament for the treatment of cancer, inflammation, or arthritis in a patient in need of such treatment.

In a fourth aspect, the invention encompasses a package comprising a compound or salt of any of Formulas I-IX in a container with instructions on how to use the compound.

In a preferred embodiment of the fourth aspect, the invention encompasses a package comprising a compound or salt of Formula I in a container with instructions on how to use the compound.

In a fifth aspect, the invention encompasses the use of a therapeutically effective amount of a compound or salt according to any of Formulas I-IX for the preparation of a medicament for the treatment of a disease or condition related to cell proliferation in a patient in need of such treatment.

In a preferred embodiment of the fifth aspect, the invention encompasses the use of a therapeutically effective amount of a compound or salt according to Formula I for the preparation of a medicament for the treatment of a disease or condition related to cell proliferation in a patient in need of such treatment.

In a sixth aspect, the invention encompasses the use of a therapeutically effective amount of a compound or salt according to any of Formulas I-IX for the preparation of a medicament for the treatment of a disease or condition related to cell proliferation in a patient in need of such treatment, wherein the disease or condition is cancer, inflammation, or arthritis.

In a preferred embodiment of the sixth aspect, the invention encompasses the use of a therapeutically effective amount of a compound or salt according to Formula I for the preparation of a medicament for the treatment of a disease or condition related to cell proliferation in a patient in need of such treatment, wherein the disease or condition is cancer, inflammation, or arthritis.

In a seventh aspect, the invention encompasses the use of therapeutically effective amount of a compound or salt of any of Formulas I-IX for the preparation of a medicament for the treatment of a disease or disorder related to the activity of heat shock protein 90, in a subject in need of such.

In a preferred embodiment of the seventh aspect, the invention encompasses the use of therapeutically effective amount of a compound or salt of Formula I for the preparation of a medicament for the treatment of a disease or disorder related to the activity of heat shock protein 90, in a subject in need of such.

In a eighth aspect, the invention encompasses the use of therapeutically effective amount of a compound or salt of any of Formulas I-IX, alone or in combination with another therapeutic agent, for the preparation of a medicament for the treatment of a disease or disorder related to the activity of heat shock protein 90 and/or its client proteins, in a subject in need of such, wherein the HSP-90 mediated disorder is selected from the group of inflammatory diseases, infections, autoimmune disorders, stroke, ischemia, cardiac disorders, neurological disorders, fibrogenetic disorders, proliferative disorders, tumors, leukemias, neoplasms, cancers, carcinomas, metabolic diseases and malignant disease.

In a preferred embodiment of the eighth aspect, the invention encompasses the use of therapeutically effective amount of a compound or salt of Formula I, alone or in combination with another therapeutic agent, for the preparation of a medicament for the treatment of a disease or disorder related to the activity of heat shock protein 90 and/or its client proteins, in a subject in need of such, wherein the HSP-90 mediated disorder is selected from the group of inflammatory diseases, infections, autoimmune disorders, stroke, ischemia, cardiac disorders, neurological disorders, fibrogenetic disorders, proliferative disorders, tumors, leukemias, neoplasms, cancers, carcinomas, metabolic diseases and malignant disease.

In a preferred aspect embodiment of the eighth aspect, the invention encompasses methods for the treatment of cancer in a subject in need of such treatment comprising administration of therapeutically effective amount of a compound or salt of Formula I, in combination with at least one other therapeutic agent.

In a more preferred aspect embodiment of the eighth aspect, the invention encompasses methods for treating cancer in a subject in need of such treatment, the methods comprising administration of therapeutically effective amount of a compound or salt of Formula I, in combination with at least one other anti-cancer agent.

In another preferred aspect embodiment of the eighth aspect, the invention encompasses methods for treating cancer, the methods comprising administration, to a subject in need of such treatment, of a therapeutically effective amount of a compound or salt of Formula I, in combination with radiation therapy.

In a ninth aspect, the invention encompasses the use of therapeutically effective amount of a compound or salt of any of Formulas I-IX for the preparation of a medicament for the treatment of a fibrogenetic disorder related to the activity of heat shock protein 90, in a subject in need of such, wherein the fibrogenetic disorder is selected from the group of scleroderma, polymyositis, systemic lupus, rheumatoid arthritis, liver cirrhosis, keloid formation, interstitial nephritis and pulmonary fibrosis.

In a tenth aspect, the invention encompasses the use of a therapeutically effective amount of a compound or salt of any of Formulas I-IX for the preparation of a medicament for protecting a subject from infection caused by an organism selected from *Plasmodium* species.

In a preferred embodiment of the tenth aspect, the invention encompasses the use of a therapeutically effective amount of a compound or salt of Formula I for the preparation of a medicament for protecting a subject from infection caused by *Plasmodium falciparum.*

In an eleventh aspect, the invention encompasses the use of a therapeutically effective amount of a compound or salt of any of Formulas I-IX for the preparation of a medicament for reducing the level of infection caused by an organism selected from *Plasmodium* species in a subject in need of such treatment.

In a preferred embodiment of the eleventh aspect, the invention encompasses the use of a therapeutically effective amount of a compound or salt of Formula I for the preparation of a medicament for reducing the level of infection caused by an organism selected from *Plasmodium* species in a subject in need of such treatment.

In a preferred aspect of the eleventh aspect, the invention encompasses the use of a therapeutically effective amount of a compound or salt of Formula I for the preparation of a medicament for reducing the level of infection caused by *Plasmodium falciparum* in a subject in need of such treatment In a twelfth aspect, the invention encompasses the use of a therapeutically effective amount of a compound or salt of any of Formulas I-IX for the preparation of a medicament for treating a patient infected with a metazoan parasite.

In a preferred embodiment of the twelfth aspect, the invention encompasses the use of a therapeutically effective amount of a compound or salt of Formula I for the preparation of a medicament for treating a patient infected with a metazoan parasite.

In a more preferred embodiment of the twelfth aspect, the invention encompasses the use of a therapeutically effective amount of a compound or salt of Formula I for the preparation of a medicament for treating a patient infected by a metazoan parasite which is *Plasmodium falciparum.*

In a thirteenth aspect, the invention encompasses the use of a therapeutically effective amount of a compound or salt of any of Formulas I-IX in combination with one or more known anti-fungal drugs for the preparation of a medicament for treating a patient infected with a fungal infection.

In a preferred embodiment of the thirteenth aspect, the invention encompasses the use of a therapeutically effective amount of a compound or salt of Formula I in combination with one or more known anti-fungal drugs for the preparation of a medicament for treating a patient infected with a fungal infection.

In the methods for treating viral infections, particular viral infections include those resulting from HIV-1 and Hepatitis C virus.

The invention further encompasses intermediates useful for preparing compounds of Formula I. These include compounds of the formula B1

B1

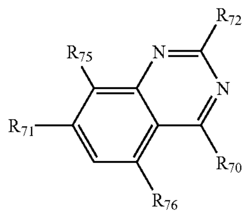

wherein $R_{70}$ is —$NR_{73}R_{74}$ where $R_{73}$ and $R_{74}$ independently represent hydrogen, $C_1$-$C_6$ alkyl, $C_3$-$C_7$ cycloalkyl, or $C_3$-$C_7$ cycloalkyl ($C_1$-$C_6$)alkyl;

$R_{71}$ is halogen or hydrazino;

$R_{72}$ is hydrogen or $C_1$-$C_6$ alkyl;

$R_{75}$ is hydrogen or halogen; and $R_{76}$ is hydrogen or halogen.

Particular compounds of formula B1 are those where $R_{71}$ is fluoro.

Other particular compounds of formula B1 are those where $R_{72}$ is methyl or hydrogen.

Still other particular compounds of formula B1 are those where $R_{71}$ is fluoro or hydrazino.

Other particular compounds of formula B1 are those where $R_{76}$ is hydrogen or fluoro.

Yet other particular compounds of formula B1 are those where $R_{71}$ and $R_{75}$ are both fluoro.

Other intermediates useful in the invention include those of Formula B2:

B2

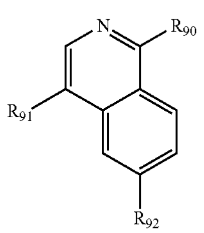

wherein $R_{90}$ is —$NR_{93}R_{94}$ where $R_{93}$ and $R_{94}$ independently represent hydrogen, $C_1$-$C_6$ alkyl, $C_3$-$C_7$ cycloalkyl, or $C_3$-$C_7$ cycloalkyl ($C_1$-$C_6$)alkyl;

$R_{91}$ is halogen, cyano, $C_1$-$C_6$ alkanoyl, hydroxyimino($C_2$-$C_6$) alkyl, or hydrogen; and $R_{92}$ is hydrazino or fluoro.

Particular compounds of formula B2 are those where $R_{92}$ is fluoro.

Other particular compounds of formula B2 are those where $R_{92}$ is hydrazino.

Other particular compounds of formula B2 are those where $R_{91}$ is bromo or acetyl.

Other particular compounds of formula B2 are those where $R_{90}$ is amino.

Definitions

In Formula I, $R_2$ is, as noted above, independently (a) hydrogen, (b) halo, or (c) an alkyl group having from 1-15 carbon atoms. All, but no more than about six, of the carbon atoms in the alkyl group may be replaced independently by the various groups listed above in connection with Formula I. Replacement of any carbon atom is permitted, i.e., both internal and terminal carbon atoms. Further, the alkyl groups of from 1-15 carbon atoms may be straight or branched.

Thus, when the alkyl group is methyl, i.e., a one carbon atom alkyl group, replacement of that carbon atom with, for example, nitrogen or sulfur, the resulting group will not be an alkyl group but instead will be an amino or thio group, respectively. Similarly, when the carbon atom being replaced terminates the alkyl group, the terminal group will become another moiety such as pyrimidinyl, amino, phenyl, or hydroxy.

Replacement of a carbon atom with a group such as, for example, oxygen, nitrogen, or sulfur will require appropriate adjustment of the number of hydrogens or other atoms required to satisfy the replacing atom's valency. Thus, when the replacement is N or O, the number of groups attached to the atom being replaced will be reduced by one or two to satisfy the valency of the nitrogen or oxygen respectively. Similar considerations will be readily apparent to those skilled in the art with respect to replacement by ethenyl and ethynyl.

Thus, replacement as permitted herein results in the term "$C_1$-$C_{15}$ alkyl" as defined in connection with Formula I encompassing groups such as, but not limited to:

amino, hydroxy, phenyl, benzyl, propylaminoethoxy, butoxyethylamino, pyrid-2-ylpropyl, diethylaminomethyl, pentylsulfonyl, methylsulfonamidoethyl, 3-[4-(butylpyrimidin-2-yl)ethyl]phenyl, butoxy, dimethylamino, 4-(2-(benzylamino)ethyl)pyridyl, but-2-enylamino, 4-(1-(methylamino)pent-3-en-2-ylthio)phenyl, 2-(N-methyl-hexanamido)ethoxy)methyl, and 4-(((3-methoxy-4-(4-methyl-1H-imidazol-2-yl)but-1-enyl)(methyl)amino)-methyl)phenyl.

Further, replacement as permitted herein may result in an $R_3$ group that exceeds 15 atoms. For example, replacing 6 carbon atoms of a 11-carbon atom straight chain alkyl group with amino, tetrahydropyran, amino, chlorophenyl, imidazolyl, and hydroxy could result in an $R_3$ group of the formula:

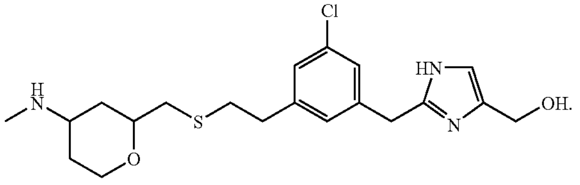

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

As used herein, the term "alkyl" includes those alkyl groups of a designated number of carbon atoms. Alkyl groups may be straight, or branched. Examples of "alkyl" include methyl, ethyl, propyl, isopropyl, butyl, iso-, sec- and tert-butyl, pentyl, hexyl, heptyl, 3-ethylbutyl, and the like.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenoxy" refers to an alkenyl group attached to the parent group through an oxygen atom.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl, naphthyl, and anthracenyl. More preferred aryl groups are phenyl and naphthyl. Most preferred is phenyl. The aryl groups of the invention may be substituted with various groups as provided herein. Thus, any carbon atom present within an aryl ring system and available for substitution may be further bonded to a variety of ring substituents, such as, for example, halogen, hydroxy, nitro, cyano, amino, $C_1$-$C_8$alkyl, $C_1$-$C_8$alkoxy, mono- and di($C_1$-$C_8$alkyl)amino, $C_3$-$C_{10}$cycloalkyl, ($C_3$-$C_{10}$cycloalkyl)alkyl, ($C_3$-$C_{10}$cycloalkyl)alkoxy, $C_2$-$C_9$heterocycloalkyl, $C_1$-$C_8$alkenyl, $C_1$-$C_8$alkynyl, halo($C_1$-$C_8$)alkyl, halo($C_1$-$C_8$)alkoxy, oxo, amino($C_1$-$C_8$)alkyl, mono- and di($C_1$-$C_8$alkyl)amino($C_1$-$C_8$)alkyl, $C_1$-$C_8$acyl, $C_1$-$C_8$acyloxy, $C_1$-$C_8$sulfonyl, $C_1$-$C_8$thio, $C_1$-$C_8$sulfonamido, $C_1$-$C_8$aminosulfonyl.

The term "carboxy" as used herein, means a —$CO_2H$ group.

The term "cycloalkyl" refers to a $C_3$-$C_8$ cyclic hydrocarbon. Examples of cycloalkyl include cyclopropyl, cyclobutyl, cyclopentyl, cyclohexyl, cycloheptyl and cyclooctyl. More preferred are $C_3$-$C_6$ cycloalkyl groups. The cycloalkyl groups of the invention may be substituted with various groups as provided herein. Thus, any carbon atom present within a cycloalkyl ring system and available for substitution may be further bonded to a variety of ring substituents, such as, for example, halogen, hydroxy, nitro, cyano, amino, $C_1$-$C_8$alkyl, $C_1$-$C_8$alkoxy, mono- and di($C_1$-$C_8$alkyl)amino, $C_3$-$C_{10}$cycloalkyl, ($C_3$-$C_{10}$cycloalkyl)alkyl, ($C_3$-$C_{10}$cycloalkyl)alkoxy, $C_2$-$C_8$heterocycloalkyl, $C_1$-$C_8$alkenyl, $C_1$-$C_8$alkynyl, halo($C_1$-$C_8$)alkyl, halo($C_1$-$C_8$) alkoxy, oxo, amino($C_1$-$C_8$)alkyl and mono- and di($C_1$-$C_8$alkyl)amino($C_1$-$C_8$)alkyl.

The terms "halogen" or "halo" indicate fluorine, chlorine, bromine, and iodine.

The term "haloalkoxy" refers to an alkoxy group substituted with one or more halogen atoms, where each halogen is independently F, Cl, Br or I. Preferred halogens are F and Cl. Preferred haloalkoxy groups contain 1-6 carbons, more preferably 1-4 carbons, and still more preferably 1-2 carbons. "Haloalkoxy" includes perhaloalkoxy groups, such as $OCF_3$ or $OCF_2CF_3$. A preferred haloalkoxy group is trifluoromethoxy.

The term "haloalkyl" refers to an alkyl group substituted with one or more halogen atoms, where each halogen is independently F, Cl, Br or I. Preferred halogens are F and Cl. Preferred haloalkyl groups contain 1-6 carbons, more preferably 1-4 carbons, and still more preferably 1-2 carbons. "Haloalkyl" includes perhaloalkyl groups, such as $CF_3$ or $CF_2CF_3$. A preferred haloalkyl group is trifluoromethyl.

The term "heterocycloalkyl" refers to a ring or ring system containing at least one heteroatom selected from nitrogen, oxygen, and sulfur, wherein said heteroatom is in a non-aromatic ring. The heterocycloalkyl ring is optionally fused to or otherwise attached to other heterocycloalkyl rings and/or non-aromatic hydrocarbon rings and/or phenyl rings. Preferred heterocycloalkyl groups have from 3 to 7 members. More preferred heterocycloalkyl groups have 5 or 6 members. Examples of heterocycloalkyl groups include, for example, 1,2,3,4-tetrahydroisoquinolinyl, piperazinyl, morpholinyl, piperidinyl, tetrahydrofuranyl, pyrrolidinyl, pyridinoyl, and pyrazolidinyl. Preferred heterocycloalkyl groups include piperidinyl, piperazinyl, morpholinyl, pyrrolidinyl, pyridinonyl, dihydropyrrolidinyl, and pyrrolidinonyl. The heterocycloalkyl groups of the invention may be substituted with various groups as provided herein. Thus, any atom present within a heterocycloalkyl ring and available for substitution may be further bonded to a variety of ring substituents, such as, for example, halogen, hydroxy, nitro, cyano, amino, $C_1$-$C_8$alkyl, $C_1$-$C_8$alkoxy, mono- and di($C_1$-$C_8$alkyl)amino, $C_3$-$C_{10}$cycloalkyl, ($C_3$-$C_{10}$cycloalkyl)alkyl, ($C_3$-$C_{10}$cycloalkyl)alkoxy, $C_2$-$C_8$heterocycloalkyl, $C_1$-$C_8$alkenyl, $C_1$-$C_8$alkynyl, halo($C_1$-$C_8$)alkyl, halo($C_1$-$C_8$) alkoxy, oxo, amino($C_1$-$C_8$)alkyl and mono- and di($C_1$-$C_8$alkyl)amino($C_1$-$C_8$)alkyl.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thienyl, 5,6,7,8-tetrahydroisoquinoline and pyrimidines. The heteroaryl groups of the invention may be substituted with various groups as provided herein. Thus, any carbon atom present within an heteroaryl ring system and available for substitution may be further bonded to a variety of ring substituents, such as, for example, halogen, hydroxy, nitro, cyano, amino, $C_1$-$C_8$alkyl, $C_1$-$C_8$alkoxy, mono- and di($C_1$-$C_8$alkyl)amino, $C_3$-$C_{10}$cycloalkyl, ($C_3$-$C_{10}$cycloalkyl) alkyl, ($C_3$-$C_{10}$cycloalkyl)alkoxy, $C_2$-$C_8$heterocycloalkyl, $C_1$-$C_8$alkenyl, $C_1$-$C_8$alkynyl, halo($C_1$-$C_8$)alkyl, halo($C_1$-$C_8$) alkoxy, oxo, amino($C_1$-$C_8$)alkyl and mono- and di($C_1$-$C_8$alkyl)amino($C_1$-$C_8$)alkyl.

Preferred examples of heteroaryl groups include thienyl, benzothienyl, pyridyl, quinolyl, pyrazolyl, pyrimidyl, imidazolyl, benzimidazolyl, furanyl, benzofuranyl, dibenzofuranyl, thiazolyl, benzothiazolyl, isoxazolyl, oxadiazolyl, isothiazolyl, benzisothiazolyl, triazolyl, pyrrolyl, indolyl, pyrazolyl, and benzopyrazolyl.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

Pharmaceutical Compositions

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water. Preferred non-human animals include domesticated animals.

The compounds of the present invention may be administered alone or in combination with at least one additional therapeutic agent or therapy, e.g., radiation therapy, to a patient in need of such treatment. The additional therapeutic agent or therapy may be administered at the same time, separately, or sequentially with respect to the administration of a compound of the invention. Such additional therapeutic agents included, but are not limited to, anti-cancer agents, anti-inflammatory agents, and the like.

The compounds of the present invention may be prepared by use of known chemical reactions and procedures. Representative methods for synthesizing compounds of the invention are presented below. It is understood that the nature of the substituents required for the desired target compound often determines the preferred method of synthesis. All variable groups of these methods are as described in the generic description if they are not specifically defined below.

Methods of Preparation

General Procedure

Representative synthetic procedures for the preparation of compounds of the invention are outlined below in following schemes. Unless otherwise indicated, all variables carry the definitions set forth above in connection with Formula I.

Those having skill in the art will recognize that the starting materials and reaction conditions may be varied, the sequence of the reactions altered, and additional steps employed to produce compounds encompassed by the present invention, as demonstrated by the following examples. In some cases, protection of certain reactive functionalities may be necessary to achieve some of the above transformations. In general, the need for such protecting groups as well as the conditions necessary to attach and remove such groups will be apparent to those skilled in the art of organic synthesis.

The disclosure of all articles and references mentioned in this application, including patents, are incorporated herein by reference in their entirety.

Scheme 1
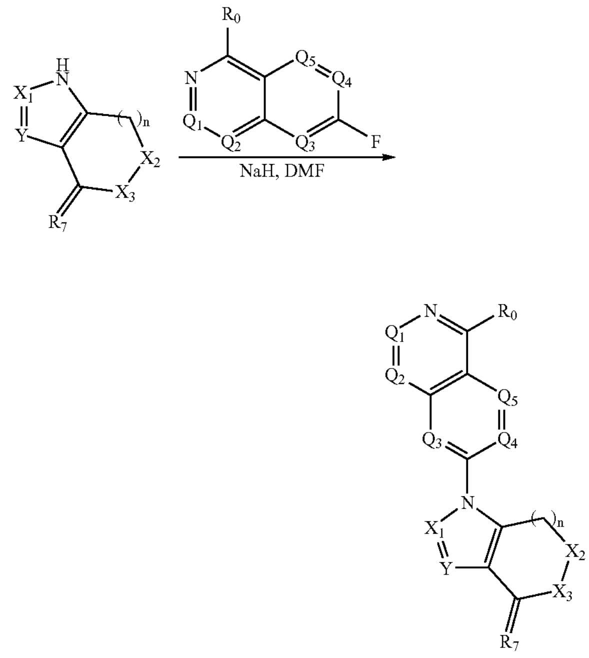
Scheme 1'
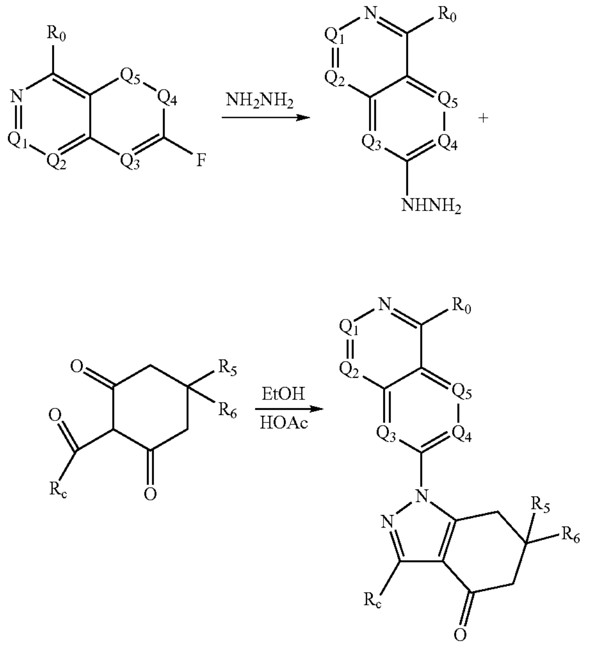
Scheme 2
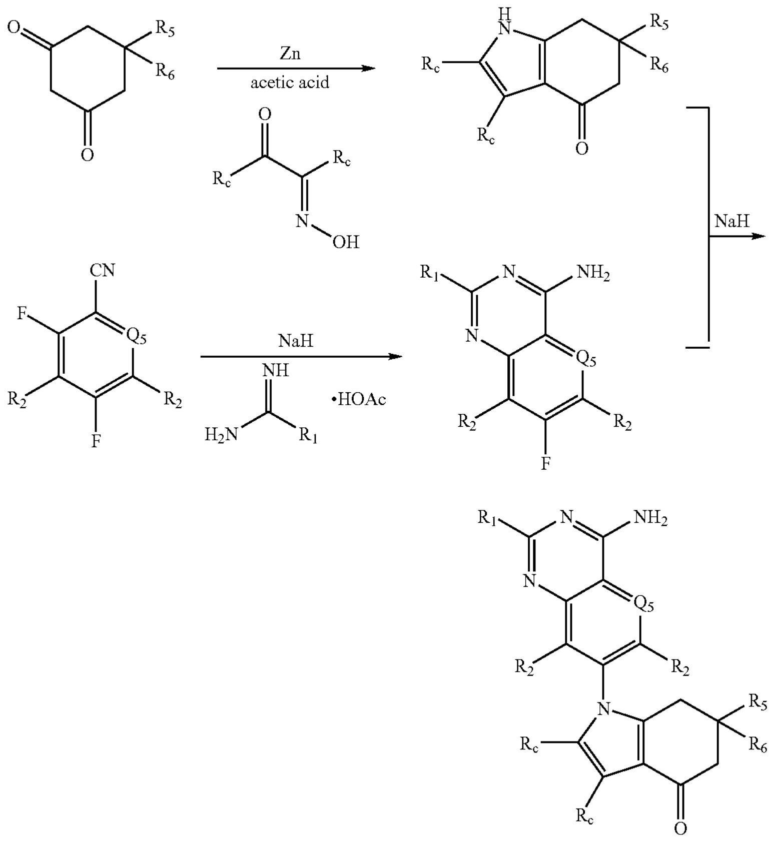

Scheme 3
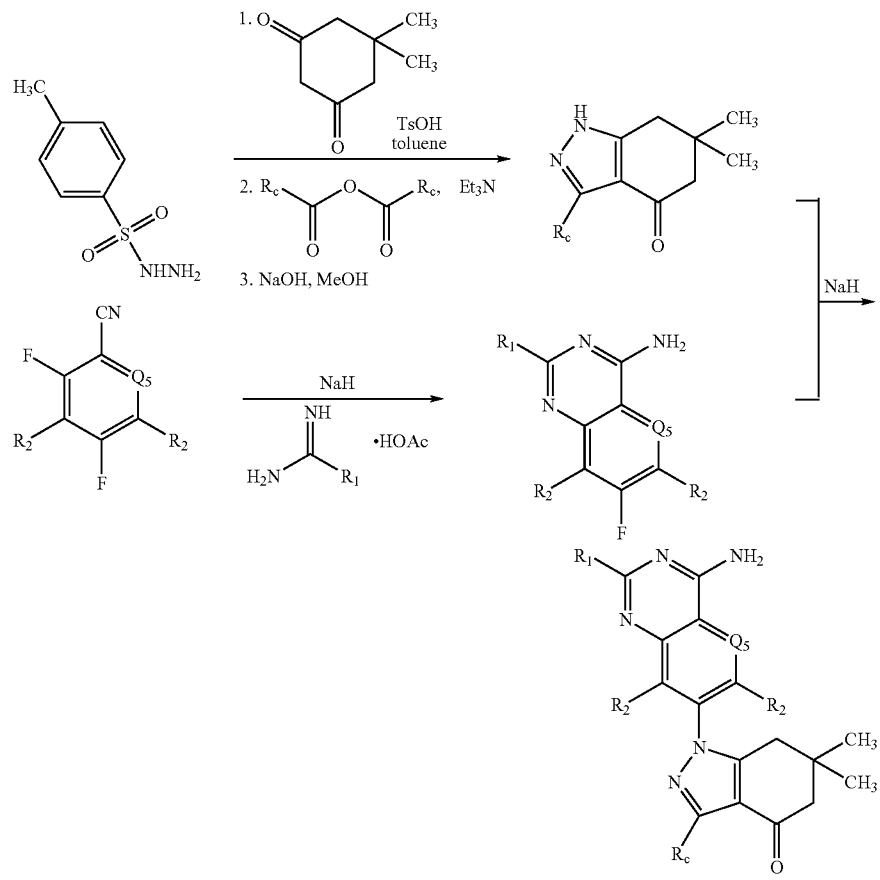
Scheme 4
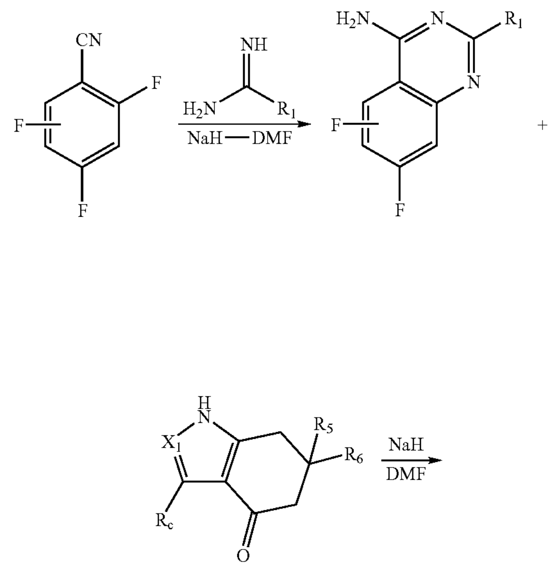
-continued
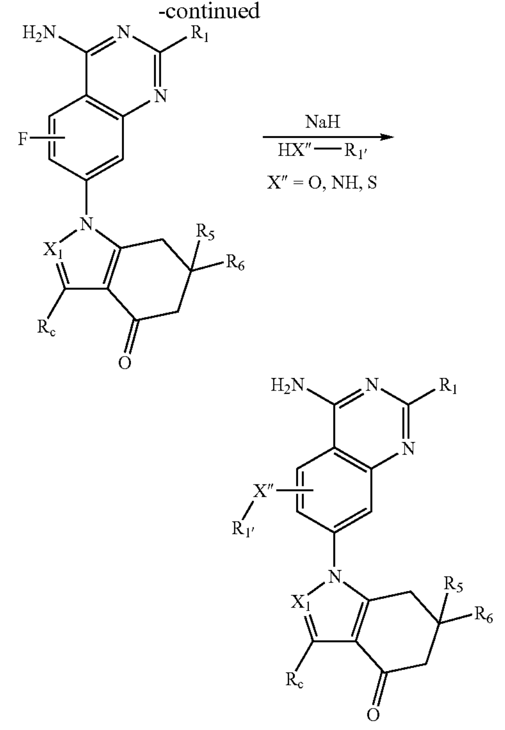

Scheme 4'
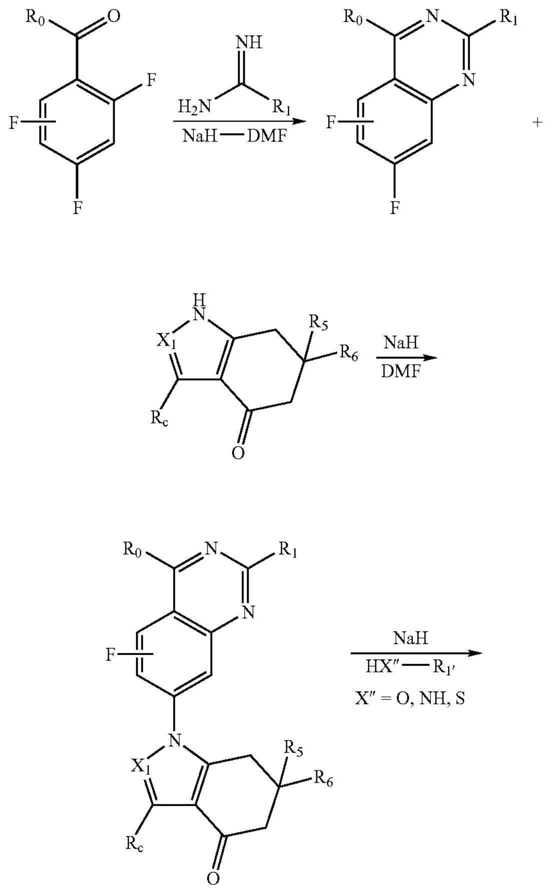
-continued
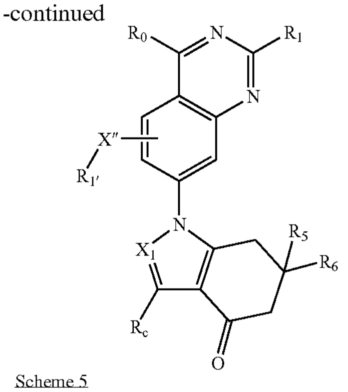
Scheme 5
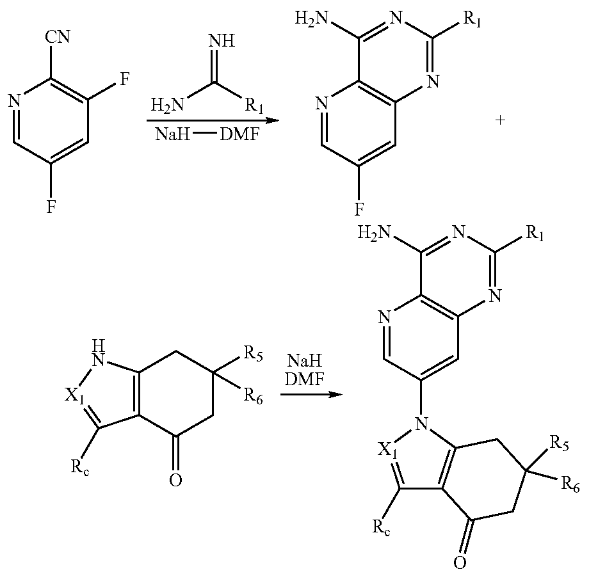
Scheme 6
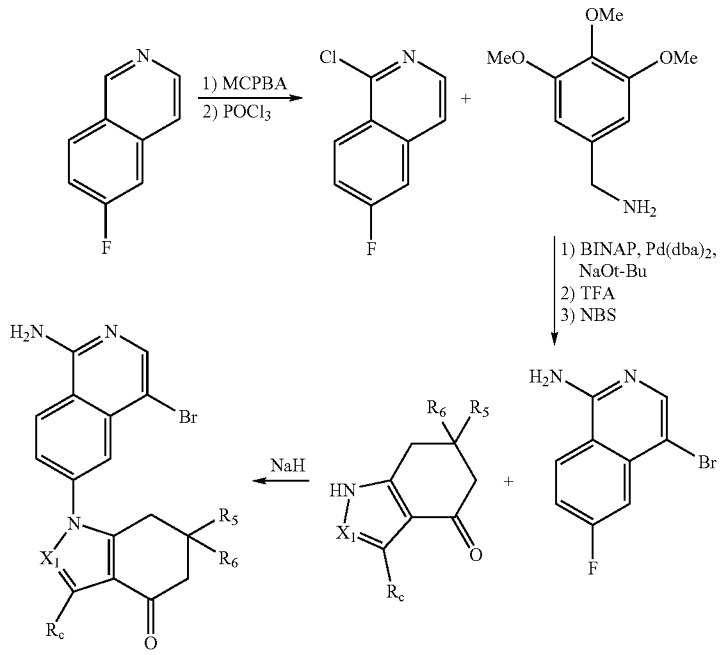

Scheme 7
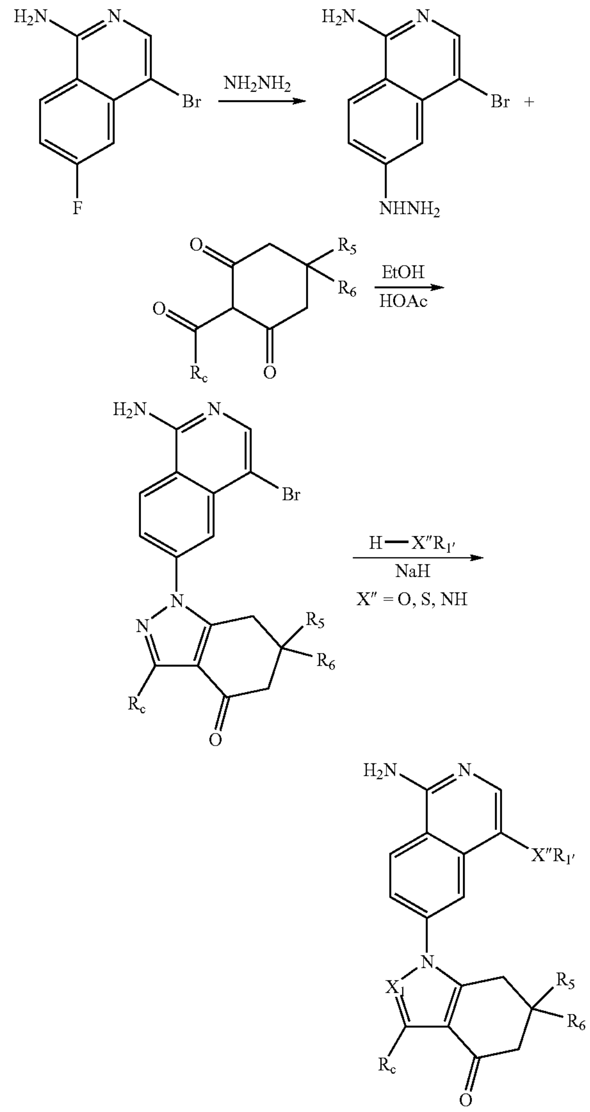
Scheme 8
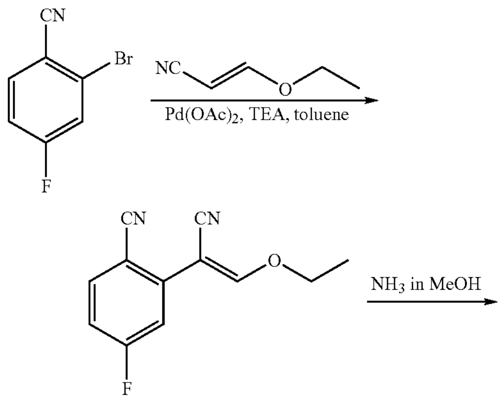
-continued
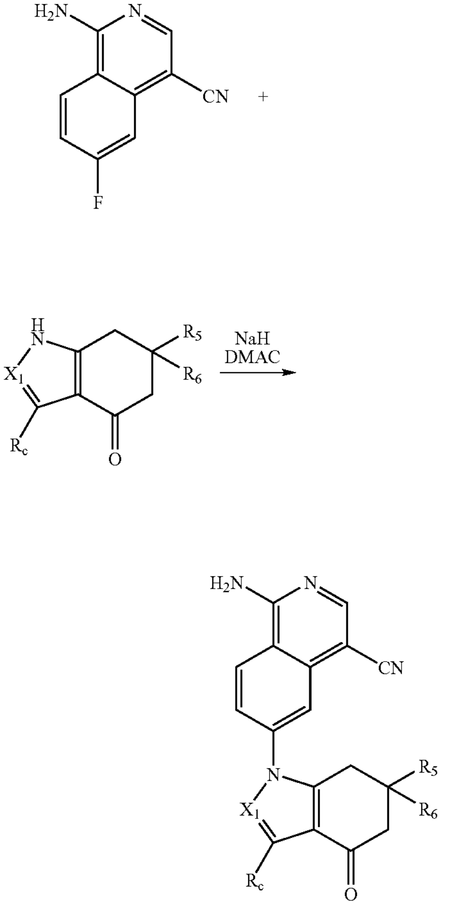
Scheme 9
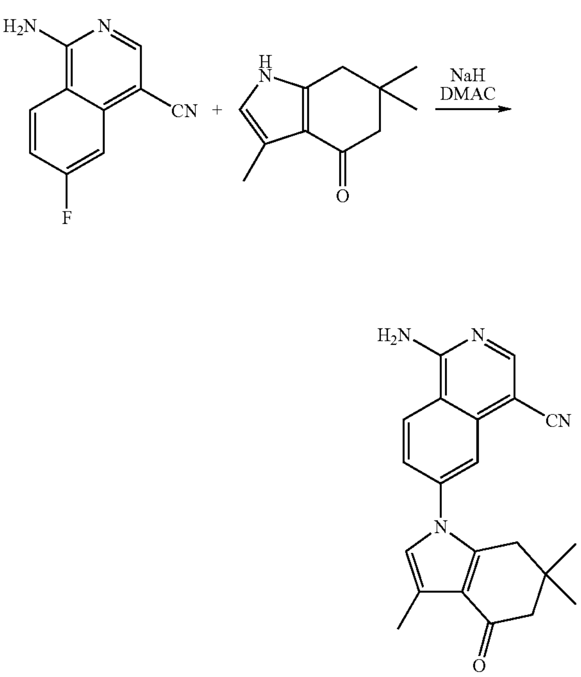

-continued
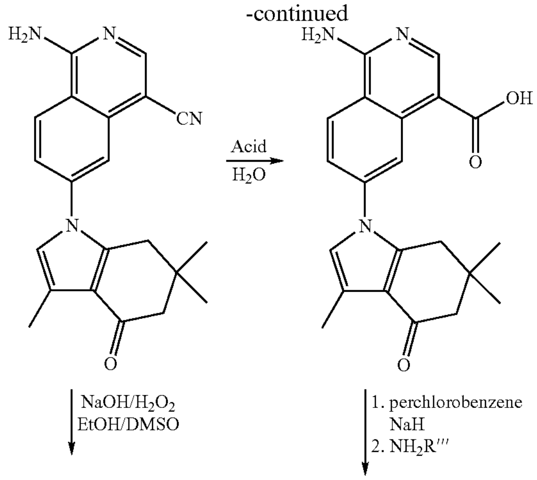
-continued
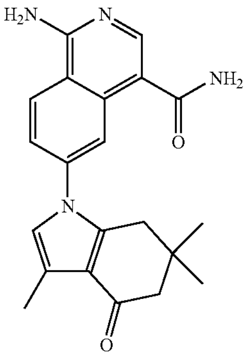
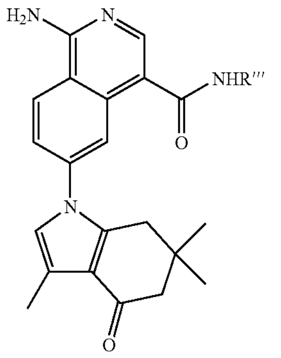
Scheme 10
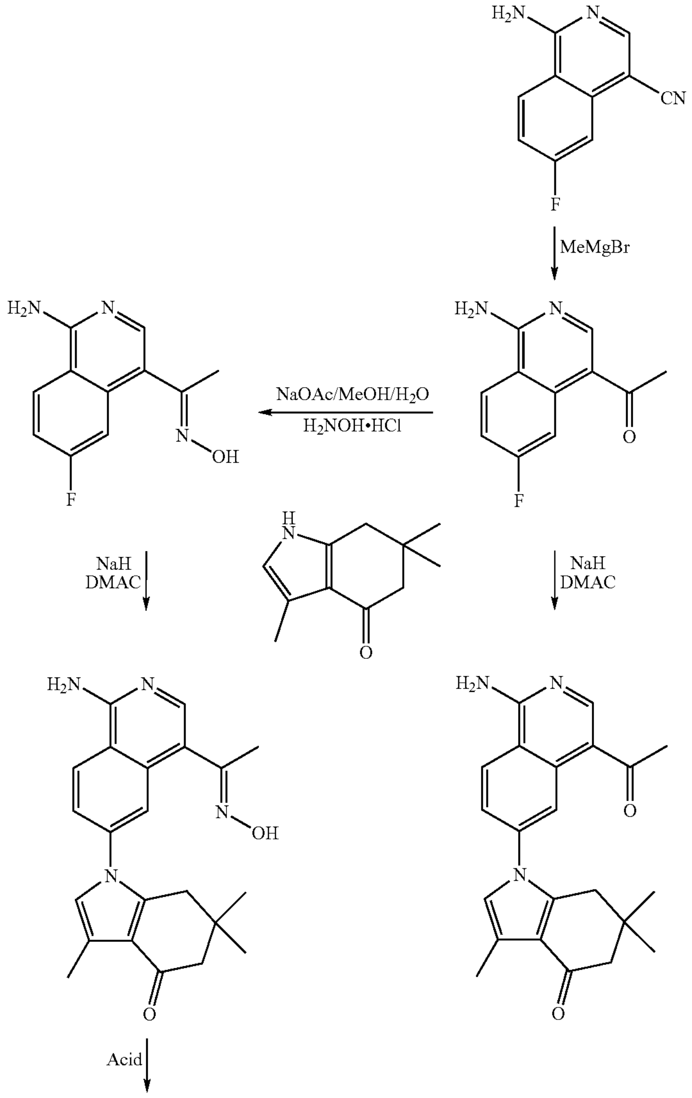

-continued

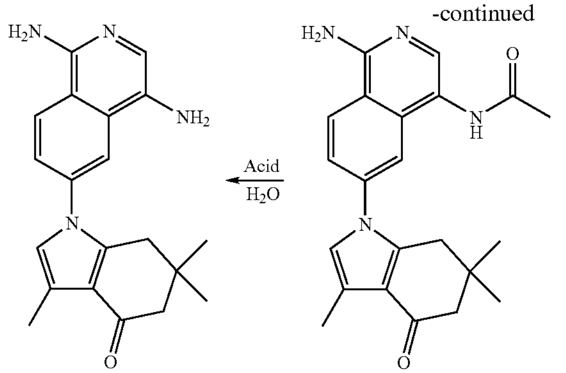

EXAMPLES

The preparation of the compounds of the invention is illustrated further by the following examples, which are not to be construed as limiting the invention in scope or spirit to the specific procedures and compounds described in them. In all cases, unless otherwise specified, the column chromatography is performed using a silica gel solid phase.

Example 1

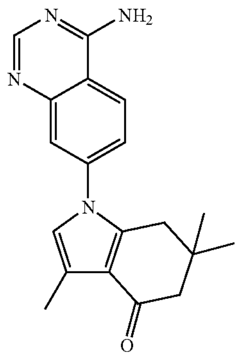

1-(4-Amino-quinazolin-7-yl)-3,6,6-trimethyl-1,5,6,7-tetrahydro-indol-4-one (Compound 1)

A suspension of 2,4-difluorobenzonitrile (1 g, 7.17 mmol), formamidine acetate (2.98 g, 28.68 mmol), and NaH (60% suspension in mineral oil, 2.29 g, 57.36 mmol) in dimethylacetamide (50 mL) is stirred at 120° C. for overnight. The reaction mixture is poured onto a saturated solution of $NaHCO_3$ (100 mL), and the aqueous phase is extracted with EtOAc (3×). The combined organic layers is washed with brine, dried over $MgSO_4$, and evaporated to dryness. Purification of the crude material by column chromatography (10% MeOH in $CH_2Cl_2$) affords 7-Fluoro-quinazolin-4-ylamine (0.2874 g, 25%). LC/MS m/z=164 $[M+H]^+$.

A solution of 7-Fluoro-quinazolin-4-ylamine (0.2203 g, 1.35 mmol), 6,6,6,-trimethyl-1,5,6,7-tetrahydro-indol-4-one (0.286 g, 1.62 mmol) and NaH (60% suspension in mineral oil, 0.081 g, 2.025 mmol) in dimethylacetamide (5 mL) is microwaved at 160° C. for 20 min. The reaction mixture is poured onto a saturated solution of $NH_4Cl$ (5 mL), and the aqueous phase is extracted with EtOAc (3×). The combined organic layers are washed with brine, dried over $MgSO_4$, and evaporated to dryness. Purification of the crude material by column chromatography (5% MeOH in $CH_2Cl_2$) affords 1-(4-Amino-quinazolin-7-yl)-3,6,6-trimethyl-1,5,6,7-tetrahydro-indol-4-one (0.1131 g, 26%). LC/MS m/z=321 $[M+H]^+$.

Example 2

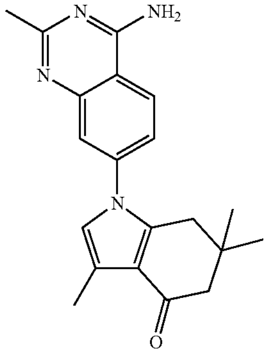

1-(4-Amino-2-methyl-quinazolin-7-yl)-3,6,6-trimethyl-1,5,6,7-tetrahydro-indol-4-one (Compound 2)

A mixture of 2,4-Difluorobenzonitrile (1.1 g, 1 eq), acetamidine hydrochloride (2.8 g, 3.78 eq) and sodium hydride (1.52 g, 8 eq) in dimethylacetamide (50 mL) is stirred at 150° C. for overnight. Then the reaction mixture is poured into sat'd $NaHCO_3$ aq. solution (300 mL), extracted by EtOAc (3×200 mL), the combined organic layers dried over $Na_2SO_4$, filtered, concentrated to give a crude product. Purification of that by flash column chromatography yields 7-Fluoro-2-methyl-quinazolin-4-ylamine (0.46 g, 33% yield). LC/MS m/z=178 $[M+H]^+$.

To 3,6,6,-trimethyl-1,5,6,7-tetrahydro-indol-4-one (0.3 g, 1.2 eq) in dimethylacetamide (50 mL) is added slowly sodium hydride (50.8 mg, 1.5 eq). The resulting mixture is stirred at RT for 0.5 h. To that 7-Fluoro-2-methyl-quinazolin-4-ylamine (0.25 g, 1 eq) is added and the mixture is stirred at 150° C. for overnight. The mixture is poured into sat'd $NaHCO_3$ aq. solution (300 mL), and extracted by EtOAc (3×100 mL). The combined organic layers are dried over $Na_2SO_4$, filtered, concentrated. The crude product is purified by flash chromatography, eluted by 50% EtOAc in Hexane to EtOAc to give 1-(4-Amino-2-methyl-quinazolin-7-yl)-3,6,6-trimethyl-1,5,6,7-tetrahydro-indol-4-one (0.135 g, 29% yield). LC/MS m/z=335 $[M+H]^+$.

Example 3

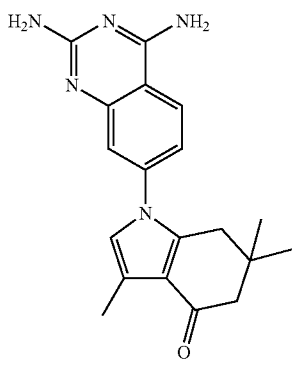

1-(2,4-Diamino-quinazolin-7-yl)-3,6,6-trimethyl-1,5,6,7-tetrahydro-indol-4-one (Compound 3)

2,4-Difluorobenzonitrile (2.78 g, 1 eq), guanidine hydrochloride (7.15 g, 3.74 eq), and sodium hydride (3.6 g, 7.6 eq) are added to dimethylacetamide (50 mL) and the resulting mixture is stirred at 150° C. for overnight. Then the reaction mixture is poured into sat'd $NaHCO_3$ aq. solution (300 mL), extracted by EtOAc (3×200 mL). The combined organic layers is dried over $Na_2SO_4$, filtered, concentrated. The crude product is purified by flash chromatography to give 7-Fluoro-quinazolin-2,4-diamine (1 g, 28% yield). LC/MS m/z=179 $[M+H]^+$.

To 3,6,6,-trimethyl-1,5,6,7-tetrahydro-indol-4-one (0.41 g, 1.2 eq) in dimethylacetamide (50 mL) is added slowly sodium hydride (69.5 mg, 1.5 eq) and the resulting mixture is stirred at RT for 0.5 h. Then 7-Fluoro-quinazolin-2,4-diamine (0.342 g, 1 eq) is added and the mixture is stirred at 150° C. for overnight. The reaction mixture is poured into sat'd $NaHCO_3$ aq. solution (300 mL), extracted by EtOAc (3×150 mL). The combined organic layers are dried over $Na_2SO_4$, filtered, concentrated. The crude product is purified by flash chromatography to give 1-(2,4-Diamino-quinazolin-7-yl)-3,6,6-trimethyl-1,5,6,7-tetrahydro-indol-4-one (0.5 g, 77.6% yield). LC/MS m/z=336 $[M+H]^+$.

Example 4

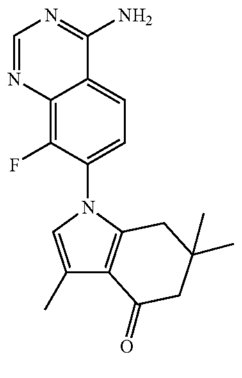

1-(4-Amino-8-fluoro-quinazolin-7-yl)-3,6,6-trimethyl-1,5,6,7-tetrahydro-indol-4-one (Compound 4)

2,3,4-Trifluoro-benzonitrile (3.00 g, 19.1 mmol) is mixed with dimethylacetamide (30 mL). Formamidine acetate (1.99 g, 19.1 mmol) and diisopropylethyl amine (10 mL, 57.3 mmol) are added, and the resulting reaction mixture is slowly heated. Upon heating, the starting heterogeneous mixture slowly turns into a homogeneous solution. At 80° C., precipitates start to form. The reaction mixture proceeds at 80° C. for ~30 minutes before it is cooled and filtered. The collected solid is further washed with DCM to afford 1.50 g of 7,8-Difluoro-quinazolin-4-ylamine (43% yield) as white solid. LC/MS found m/z=182 $[M+H]^+$.

Sodium hydride (60% suspension in mineral oil, 50 mg, 1.3 mmol) is added to a solution of 3,6,6-Trimethyl-1,5,6,7-tetrahydro-indol-4-one (50 mg, 0.29 mmol) in anhydrous DMF (1 mL). This mixture is stirred at room temperature for 5 minutes before 7,8-Difluoro-quinazolin-4-ylamine (75 mg, 0.41 mmol) is added. After 10 minutes at room temperature, the reaction mixture is heated at 50° C. overnight. The cooled reaction mixture is partitioned between ethyl acetate and water to remove DMF, and the organic layer is concentrated to dryness via Rotovap. The resulting crude residue is further purified through two consecutive silica gel columns (0%-8% of methanol in DCM, gradient) to afford 1-(4-Amino-8-fluoro-quinazolin-7-yl)-3,6,6-trimethyl-1,5,6,7-tetrahydro-indol-4-one (15 mg, not optimized) as white solid. LC/MS m/z=339 $[M+H]^+$.

Example 5

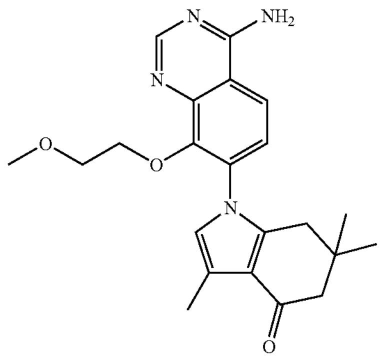

1-[4-Amino-8-(2-methoxy-ethoxy)-quinazolin-7-yl]-3,6,6-trimethyl-1,5,6,7-tetrahydro-indol-4-one (Compound 5)

In a small microwave vial with a stir bar, 2-methoxyethanol (19.3 mg, 0.253 mmol) is dissolved in DMF (1 mL). To this solution is added sodium hydride (60% suspension in mineral oil, 10.13 mg, 0.2532 mmol) and the mixture is stirred at room temperature for 5 minutes and 1-(4-Amino-8-fluoro-quinazolin-7-yl)-3,6,6-trimethyl-1,5,6,7-tetrahydro-indol-4-one (42.8 mg, 0.126 mmol) is added. The reaction is sealed and placed in the microwave reactor where it is heated to 150° C. for 30 minutes. The reaction is cooled, quenched by adding 5 mL sat. $NH_4Cl$ (aq) and extracted with $CH_2Cl_2$ (3×1 mL). The combined organics are purified by silica gel chromatography by two gradient runs on the same column, the first 0% to 100% ethyl acetate in hexanes and the second 0% to 50% methanol in ethyl acetate. This gives the desired 1-[4-Amino-8-(2-methoxy-ethoxy)-quinazolin-7-yl]-3,6,6-trimethyl-1,5,6,7-tetrahydro-indol-4-one as a tan powder (40 mg, 80% yield) (LC/MS m/z=395 $[M+H]^+$).

Example 6

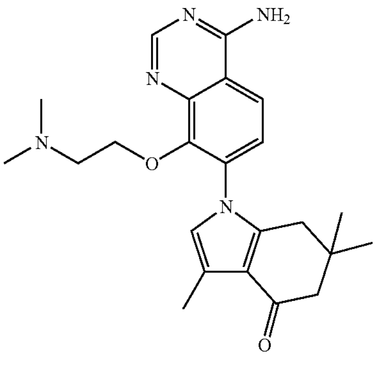

1-[4-Amino-8-(2-dimethylamino-ethoxy)-quinazolin-7-yl]-3,6,6-trimethyl-1,5,6,7-tetrahydro-indol-4-one (Compound 6)

In a microwave vial with a stir bar, N,N-dimethylethanolamine (101 mg, 1.13 mmol) is dissolved in DMF (5 mL). To this solution is added sodium hydride (60% suspension in mineral oil, 45 mg, 1.136 mmol) and the mixture stirred at room temperature for 5 minutes and 1-(4-Amino-8-fluoro-quinazolin-7-yl)-3,6,6-trimethyl-1,5,6,7-tetrahydro-indol-4-one (192 mg, 0.568 mmol) is added. The reaction is sealed and placed in the microwave reactor where it is heated to 150° C. for 30 minutes. The reaction is cooled, quenched by adding 25 mL sat. $NH_4Cl$ (aq) and extracted with $CH_2Cl_2$ (3×5 mL). The combined organics are dried with $Na_2SO_4$, concentrated and purified by silica gel chromatography by two gradient runs on the same column, the first 0% to 100% ethyl acetate in hexanes and the second 0% to 50% methanol in ethyl acetate. This gives 1-[4-Amino-8-(2-dimethylamino-ethoxy)-quinazolin-7-yl]-3,6,6-trimethyl-1,5,6,7-tetrahydro-indol-4-one as a yellow powder (171 mg, 74% yield) (LC/MS m/z=408 $[M+H]^+$).

Example 7

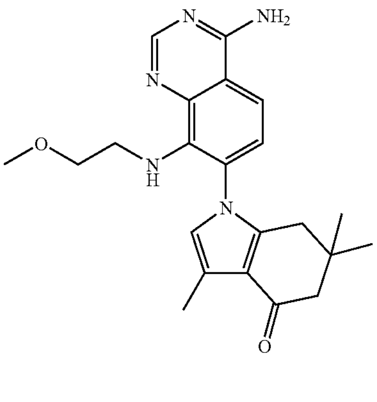

1-[4-Amino-8-(2-methoxy-ethylamino)-quinazolin-7-yl]-3,6,6-trimethyl-1,5,6,7-tetrahydro-indol-4-one In a small microwave vial with a stir bar, 2-Methoxy-ethylamine (0.1 mmol, 75 mg) is dissolved in 1 mL DMF. To this solution is added sodium hydride (60% suspension in mineral oil) (0.1 mmol, 4 mg) and the mixture is stirred at rt for 5 min. and then 1-(4-Amino-8-fluoro-quinazolin-7-yl)-3,6,6-trimethyl-1,5,6,7-tetrahydro-indol-4-one (0.044 mmol, 15 mg) is added. The reaction is sealed and placed in the microwave reactor where it is heated to 150° C. for 30 min. The reaction is cooled and quenched by pouring into 10 mL of Sat'd. $NH_4Cl$ aq. and extracted 3 times with 2 mL $CH_2Cl_2$. The combined organics are dried with $Na_2SO_4$, concentrated, and purified by silica gel chromatography on Biotage using a gradient of 0-50% MeOH in $CH_2Cl_2$. 1-[4-Amino-8-(2-methoxy-ethylamino)-quinazolin-7-yl]-3,6,6-trimethyl-1,5,6,7-tetrahydro-indol-4-one is isolated (8 mg, LC/MS m/z=393 $[M+H]^+$) as a tan powder.

Example 8

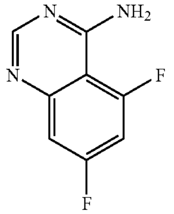

5,7-Difluoro-quinazolin-4-ylamine 2,4,6-Trifluoro-benzonitrile (3.59 mmol, 500 mg) is dissolved in DMA (5 mL) and then formamidine acetate is added (3.59 mmol, 373.75 mg) followed by DIEA (10.78 mmol, 1.39 g). The reaction is stirred for 16 hr at 100° C. A solid forms, is collected by filtration and the solid is washed with $CH_2Cl_2$. This gives desired product 5,7-Difluoro-quinazolin-4-ylamine (227 mg, LC/MS m/z=182 $[M+H]^+$) as a white powder.

Example 9

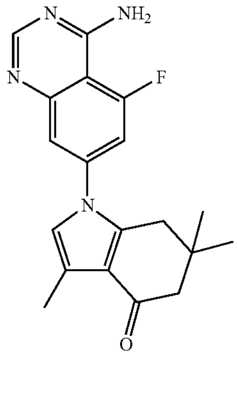

1-(4-Amino-5-fluoro-quinazolin-7-yl)-3,6,6-trimethyl-1,5,6,7-tetrahydro-indol-4-one 3,6,6-Trimethyl-1,5,6,7-tetrahydro-indol-4-one (0.61 mmol, 107.6 mg) is dissolved in 5 mL DMF. To this solution is added sodium hydride (60% suspension in mineral oil) (0.77 mmol, 30.8 mg) and the mixture is stirred at rt for 5 min.

and then 5,7-Difluoro-quinazolin-4-ylamine (0.55 mmol, 100 mg) is added. The reaction is stirred at 50° C. for 22 h. The reaction is cooled and quenched by pouring into 100 ml sat. $NH_4Cl$ aq. and extracted 3 times with 20 mL $CH_2Cl_2$. The combined organics are dried with $Na_2SO_4$, concentrated, and purified by silica gel chromatography on Biotage using a gradient of 0-15% MeOH in $CH_2Cl_2$. 1-(4-Amino-5-fluoro-quinazolin-7-yl)-3,6,6-trimethyl-1,5,6,7-tetrahydro-indol-4-one is isolated (35 mg, LC/MS m/z=339 $[M+H]^+$) as a white powder.

Example 10

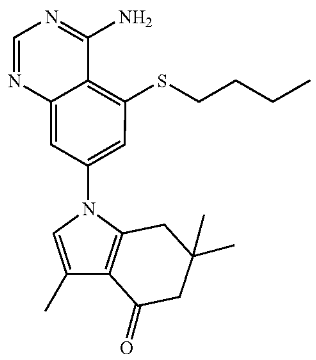

1-(4-Amino-5-butylsulfanyl-quinazolin-7-yl)-3,6,6-trimethyl-1,5,6,7-tetrahydro-indol-4-one In a small microwave vial with a stir bar, butanethiol (0.494 mmol, 44.56 mg) is dissolved in 3 mL DMF. To this solution is added NaH (60% suspension in mineral oil) (0.494 mmol, 20 mg) and the mixture is stirred at rt for 5 minutes and then 1-(4-Amino-5-fluoro-quinazolin-7-yl)-3,6,6-trimethyl-1,5,6,7-tetrahydro-indol-4-one (0.0988 mmol, 33.4 mg) is added. The reaction is sealed and placed in the microwave reactor where it is heated to 120° C. for 30 min. The reaction is cooled and quenched by pouring into 30 ml sat. $NH_4Cl$ aq. and extracted 3 times with 10 mL EtOAc. The combined organics are dried with $Na_2SO_4$, concentrated, and purified by silica gel chromatography on Biotage using a gradient of 0-20% MeOH in DCM. 1-(4-Amino-5-butylsulfanyl-quinazolin-7-yl)-3,6,6-trimethyl-1,5,6,7-tetrahydro-indol-4-one is isolated (22.1 mg, LC/MS m/z=409 $[M+H]^+$) as a yellow powder.

Example 11

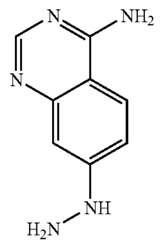

7-Hydrazino-quinazolin-4-ylamine

7-Fluoro-quinazolin-4-ylamine (0.306 mmol, 50 mg) is dissolved in Hydrazine (2 mL) and heated in an open flask until all the liquid is gone. The resulting solid is taken up in isopropanol and stirred for 30 minutes and the solid is collected by filtration. This gives desired product 7-Hydrazino-quinazolin-4-ylamine (32 mg, LC/MS m/z=176 $[M+H]^+$) as a tan powder.

Example 12

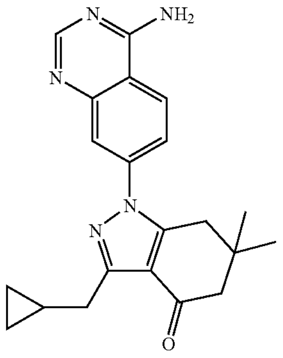

1-(4-Amino-quinazolin-7-yl)-3-cyclopropylmethyl-6,6-dimethyl-1,5,6,7-tetrahydro-indazol-4-one 7-Hydrazino-quinazolin-4-ylamine (0.092, 16 mg) is dissolved in 1 mL EtOH and 2-(2-Cyclopropyl-acetyl)-5,5-dimethyl-cyclohexane-1,3-dione (0.092 mmol, 20.4 mg) is added. The reaction is stirred at 50° C. for 22 h. The reaction is cooled and quenched by pouring into 20 mL $H_2O$ and extracted 3 times with 5 mL $CH_2Cl_2$. The combined organics are dried with $Na_2SO_4$, concentrated, and purified by silica gel chromatography on Biotage using a gradient of 0-15% MeOH in DCM. 1-(4-Amino-quinazolin-7-yl)-3-cyclopropylmethyl-6,6-dimethyl-1,5,6,7-tetrahydro-indazol-4-one is isolated (1 mg, LC/MS m/z=362 $[M+H]^+$)) as a white powder.

Example 13

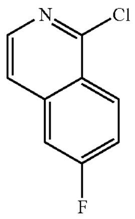

1-chloro-6-fluoro-isoquinoline

To a solution of 6-fluoroisoquinoline (2.64 g, 17.9 mmol) in $CH_2Cl_2$ (70 mL) cooled at 0° C., MCPBA is added (3.4 g, 19.69 mmol). The reaction mixture is stirred at RT for 16 h. After 1 h of stirring, a yellow white precipitate forms. The solvent is evaporated under reduced pressure. To the yellow solid is added $CH_2Cl_2$ (5 mL), and the solid is isolated by vacuum filtration. Rinsing the solid with $CH_2Cl_2$ yields a white solid, which is dried under vacuum to afford 3 g (100%) of 6-fluoro-isoquinoline N-oxide.

To a solution of 6-fluoroisoquinoline N-oxide (3 g, 18 mmol) in $CHCl_3$ (50 mL) is added phosphorus oxychloride (5 mL, 54 mmol). The reaction mixture is refluxed for 2 h. The reaction mixture is poured into ice, and the pH is brought to pH 8-9 with 5 M NaOH. The aqueous phase is extracted with $CH_2Cl_2$ (3×). The combined organic layers are dried over $MgSO_4$, and evaporated. Purification of the crude product by Biotage column eluted with 0-30% EtOAc/hexanes afforded 1.06 g (35%) of 1-chloro-6-fluoro-isoquinoline. LC/MS m/z=182 $[M+H]^+$.

Example 14

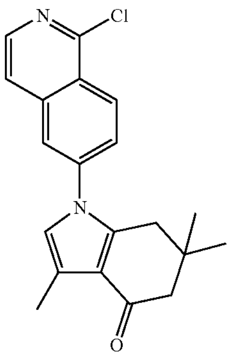

1-(3-chloro-isoquinolin-6-yl)-3,6,6-trimethyl-1,5,6,7-tetrahydro-indol-4-one

To a solution of 1-chloro-6-fluoro-isoquinoline (0.0847 g, 0.47 mmol) in DMF (2 mL) are added pyrrole (0.1 g, 0.56 mmol) and NaH (0.028 g, 0.71 mmol). The reaction mixture is microwaved at 160° C. for 20 min. The reaction mixture is cooled to RT, and treated with $NH_4Cl$ (satd. aq., 2 mL). The aqueous phase is extracted with EtOAc (2×). The combined organic layers are washed with brine, and dried over $MgSO_4$. The solvent is evaporated and the residue is dried under vacuum. Purification of the crude material using a Biotage column (0-50% EtOAc/hexanes) affords 0.014 g (9%) of 1-(3-chloro-isoquinolin-6-yl)-3,6,6-trimethyl-1,5,6,7-tetrahydro-indol-4-one. LC/MS m/z=339 $[M+H]^+$, RT=4.01 min.

Example 15

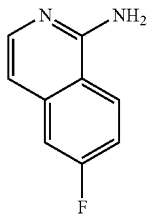

1-amino-6-fluoro-isoquinoline

A suspension of 1-chloro-6-fluoro-isoquinoline (0.9708 g, 5.35 mmol), 3,4,5-methoxybenzylamine (0.92 mL, 5.35 mmol), $Pd(dba)_2$ (0.31 g, 0.54 mmol), BINAP (0.34 g, 0.54 mmol) and NaOtBu (1.54 g, 16.05 mmol) in toluene (15 mL) is microwaved at 120° C. for 40 min. The reaction mixture is cooled to RT, then filtered through a pad of Celite. The filter cake is rinsed with EtOAc. The filtrate is concentrated and the crude product is purified by chromatography using a Biotage column (10-60% EtOAc/hexanes) to afford 1.26 g (69%) of 1-(3,4,5-trimethoxybenzyl)amino-6-fluoro-isoquinoline. m/z=343 $[M+H]^+$.

A solution of 1-(3,4,5-trimethoxybenzyl)amino-6-fluoro-isoquinoline (1.26 g, 3.68 mmol) in TFA (30 mL) is refluxed for 16 h. The solvent is evaporated under reduced pressure. Anhydrous MeOH (30 mL) is added to the residue. Solid $K_2CO_3$ is slowly added until pH>8. The suspension is filtered through a pad of Celite, and the solvent is evaporated under reduced pressure. The residue is dissolved in $CH_2Cl_2$ and filtered through a pad of Celite. The filter cake is rinsed with $CH_2Cl_2$, and the solvent is evaporated under reduced pressure. The residue is dried under vacuum to afford 0.41 g (69%) of 1-amino-6-fluoro-isoquinoline. LC/MS m/z=163 $[M+H]^+$.

Example 16

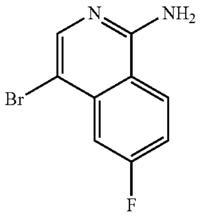

1-amino-4-bromo-6-fluoro-isoquinoline (Compound 7)

To a solution of 1-amino-6-fluoro-isoquinoline (0.41 g, 2.53 mmol) in $CHCl_3$ (25 mL) is added NBS (0.45 g, 2.53 mmol), and the reaction mixture is stirred RT for 1.5 h. The reaction mixture is treated with water (10 mL). The aqueous phase is extracted with $CH_2Cl_2$ (2×). The combined organic layers are washed with brine, and dried over $MgSO_4$. The solvent is evaporated and the residue is dried under vacuum. Purification of the crude material using a Biotage column (10-40% $MeOH/CH_2Cl_2$) afforded 0.395 g (65%) of 1-amino-4-bromo-6-fluoro-isoquinoline. LC/MS m/z=242 $[M+H]^+$.

Example 17

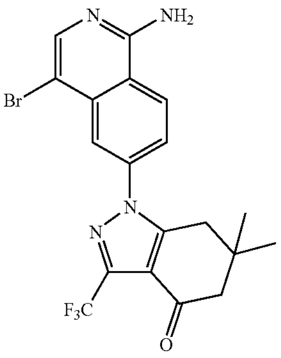

1-(1-Amino-4-bromo-isoquinolin-6-yl)-6,6-dimethyl-3-trifluoromethyl-1,5,6,7-tetrahydro-indazol-4-one (Compound 8)

To a solution of 1-amino-4-bromo-6-fluoro-isoquinoline (0.0395 g, 0.164 mmol) in DMF (1 mL) are added 6,6-Dimethyl-3-trifluoromethyl-1,5,6,7-tetrahydro-indazol-4-one (0.046 g, 0.2 mmol) and NaH (0.008 g, 0.2 mmol). The reaction mixture is microwaved at 120° C. for 40 min, cooled to RT, and treated with $NH_4Cl$ (satd. aq, 2 mL). The aqueous phase is extracted with EtOAc (2×). The combined organic layers are washed with brine, and dried over $MgSO_4$. The solvent is evaporated and the residue is dried under vacuum. Purification of the crude material using a Biotage column (10% $MeOH/CH_2Cl_2$) affords 0.039 g (53%) of 1-(1-Amino-4-bromo-isoquinolin-6-yl)-6,6-dimethyl-3-trifluoromethyl-1,5,6,7-tetrahydro-indazol-4-one. LC/MS m/z=454 $[M+H]^+$.

Example 18

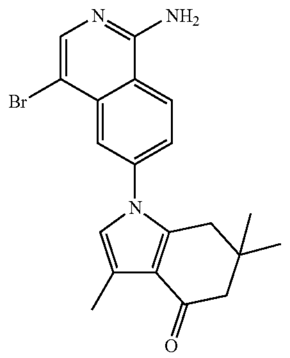

1-(1-Amino-4-bromo-isoquinolin-6-yl)-3,6,6-trimethyl-1,5,6,7-tetrahydro-indol-4-one (Compound 9)

To a solution of 1-amino-4-bromo-6-fluoro-isoquinoline (0.029 g, 0.12 mmol) in DMF (1 mL) are added 3,6,6-Trimethyl-1,5,6,7-tetrahydro-indol-4-one (0.042 g, 0.24 mmol) and NaH (0.01 g, 0.24 mmol). The reaction mixture is microwaved at 120° C. for 40 min, cooled to RT, and treated with $NH_4Cl$ (satd. aq, 2 mL). The aqueous phase is extracted with EtOAc (2×). The combined organic layers are washed with brine, and dried over $MgSO_4$. The solvent is evaporated and the residue is dried under vacuum. Purification of the crude material using a Biotage column (0-10% $MeOH/CH_2Cl_2$) affords 0.0118 g (25%) of 1-(1-Amino-4-bromo-isoquinolin-6-yl)-3,6,6-trimethyl-1,5,6,7-tetrahydro-indol-4-one. LC/MS m/z=399 $[M+H]^+$.

Example 19

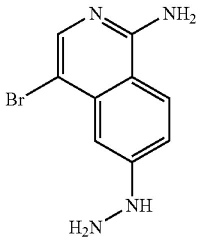

4-Bromo-6-hydrazino-isoquinolin-1-ylamine

A solution of 1-amino-4-bromo-6-fluoro-isoquinoline (0.1179 g, 0.49 mmol), and hydrazine (0.5 mL) in THF (5 mL) is microwaved at 100° C. for 40 min. Then it is placed in an oil bath and is stirred at 100° C. for 16 h. The reaction mixture is cooled to RT. It is treated with $NaHCO_3$ (satd. aq, 10 mL). The aqueous phase is extracted with EtOAc (2×). The combined organic layers are washed with brine, and dried over $MgSO_4$. The solvent is evaporated and the residue is dried under vacuum to afford 0.079 g (64%) of 4-Bromo-6-hydrazino-isoquinolin-1-ylamine. LC/MS m/z=254 $[M+H]^+$.

Example 20

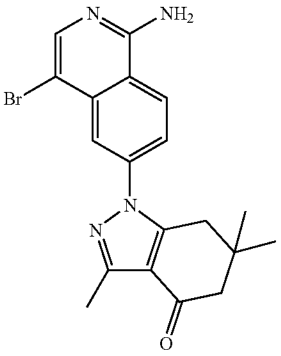

1-(1-Amino-4-bromo-isoquinolin-6-yl)-3,6,6-trimethyl-1,5,6,7-tetrahydro-indazol-4-one (Compound 10)

A suspension of 4-Bromo-6-hydrazino-isoquinolin-1-ylamine (0.097 g, 0.38 mmol) and 2-acetyl-5,5-dimethyl-1,3-cyclohexanedione (0.074 g, 0.41 mmol) in EtOH/Acetic acid (3:1, 7 mL) is microwaved at 150° C. for 20 min. The solvent is evaporated and the residue is dried under vacuum. Purification of the crude material using a Biotage column (0-10% $MeOH/CH_2Cl_2$) afforded 0.1223 g (80%) of 1-(1-Amino-4-bromo-isoquinolin-6-yl)-3,6,6-trimethyl-1,5,6,7-tetrahydro-indazol-4-one. LC/MS m/z=400 $[M+H]^+$.

Example 21

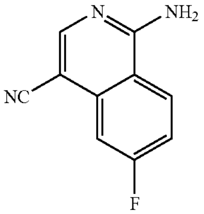

1-amino-6-fluoro-isoquinoline-4-carbonitrile

Palladium acetate (II) (0.556 g, 2.5 mmol) is added to a degassed solution of 2-bromo-4-fluoro-benzonitrile (10 g, 50 mmol), 3-ethoxyacrylonitrile (10.3 mL, 100 mmol) and triethylamine (14 mL, 100 mmol) in toluene (75 mL). The reaction mixture is stirred in an oil bath at 100° C. for 1 day. The reaction mixture is cooled to RT, filtered through a pad of Celite, and the filter cake is rinsed with EtOAc. After evaporation of the solvent, the residue is purified using a Biotage column eluted with 0-50% EtOAc/hexanes (20 CV) to afford 8.77 g (94%) of 2-(1-cyano-2-ethoxy-vinyl)-4-fluoro-benzonitrile. LC/MS: RT=3.38 min, no ionization.

A solution of ammonia in MeOH (7 N, 20 mL) is added to 2-(1-cyano-2-ethoxy-vinyl)-4-fluoro-benzonitrile (0.88 g, 4 mmol). The reaction mixture is stirred at RT for 5 h. The orange precipitate is collected by vacuum filtration to afford 0.297 g (40%) of 1-amino-6-fluoro-isoquinoline-4-carbonitrile as an orange solid. LC/MS m/z=188 $[M+H]^+$, RT=2.10-2.15 min. $^1H$ NMR ($CDCl_3$, 25 deg, 500 MHz): δ 8.44 (dd, 2H), 8.18 (t, 1H), 8.04 (bs, 4H), 7.73 (d, 1H), 7.63 (dt, 1H), 7.53 (dt, 2H), 7.43 (dd, 2H)

Example 22

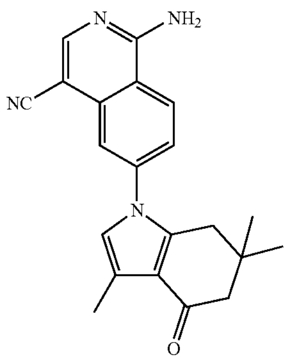

1-amino-6-(3,6,6-trimethyl-4-oxo-4,5,6,7-tetrahydro-indol-1-yl)-isoquinoline-4-carbonitrile To a solution of 1-amino-6-fluoro-isoquinoline-4-carbonitrile (0.109 g, 0.58 mmol) in DMF (5 mL) are added pyrrole (0.15 g, 0.87 mmol) and NaH (0.035 g, 0.87 mmol). The reaction mixture is microwaved at 120° C. for 40 min. The reaction mixture is cooled to RT, and treated with $H_2O$ (10 mL). The aqueous phase is extracted with EtOAc (2×). The combined organic layers are washed with brine, and dried over $MgSO_4$. The solvent is evaporated and the residue is dried under vacuum. Purification of the crude material using a Biotage column (0-20% $MeOH/CH_2Cl_2$) affords 0.08 g (40%) of 1-amino-6-(3,6,6-trimethyl-4-oxo-4,5,6,7-tetrahydro-indol-1-yl)-isoquinoline-4-carbonitrile. LC/MS m/z=345 $[M+H]^+$, RT=2.98 min.

Example 23

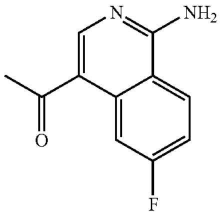

1-(1-amino-6-fluoro-isoquinolin-4-yl)-ethanone

To the solution of 1-amino-6-fluoro-isoquinoline-4-carbonitrile (3 g, 1 eq) in toluene (100 mL) is added 3M MeMgBr in ether (53 mL, 10 eq) at 0° C., then the mixture is stirred at RT for 2 h, then refluxed overnight. The reaction is cooled down and acidified by 2 N HCl aq. to pH~3, then neutralized by Sat'd $NaHCO_3$ aq (300 mL), extracted by dichloromethane (3×150 mL). The organic layer is dried over $Na_2SO_4$, filtered, concentrated to give product 1-(1-amino-6-fluoro-isoquinolin-4-yl)-ethanone (0.8 g, 24%). LC/MS m/z=205 $[M+H]^+$.

Example 24

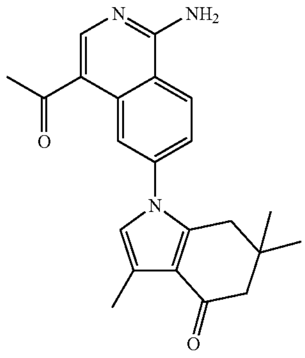

1-(4-acetyl-1-amino-isoquinolin-6-yl)-3,6,6 trimethyl-1,5,6,7-tetrahydro-indol-4-one To 3,6,6,-trimethyl-1,5,6,7-tetrahydro-indol-4-one (0.104 g, 1.2 eq) in dimethylacetamide (3 mL), sodium hydride (14.4 mg, 1.2 eq) is added slowly and stirred at RT for 0.5 h. Then 1-(1-amino-6-fluoro-isoquinolin-4-yl)-ethanone (0.1 g, 1 eq) is added and stirred at 150° C. overnight. The reaction mixture is poured into Sat'd $NH_4Cl$ aq. (200 mL), extracted by EtOAc (3×100 mL), dried over $Na_2SO_4$, filtered, concentrated to give a crude product. That is purified by Biotage chromatography, eluted by 50-100% EtOAc in Hexanes to give 1-(4-acetyl-1-amino-isoquinolin-6-yl)-3,6,6 trimethyl-1,5,6,7-tetrahydro-indol-4-one (48.1 mg, 27%). LC/MS m/z=362 $[M+H]^+$.

Example 25

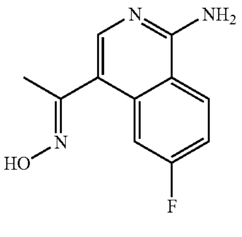

1-(1-amino-6-fluoro-isoquinolin-4-yl)-ethanone oxime 1-(1-amino-6-fluoro-isoquinolin-4-yl)-ethanone (0.8 g, 1 eq), hydroxylamine hydrochloride (1.36 g, 5 eq), and NaOAc (1.6 g. 5 eq) in MeOH (70 mL) and $H_2O$ (70 mL) is stirred at RT over 3-day, then concentrated to remove MeOH, poured into Sat'd $NaHCO_3$ aq. (300 mL), extracted by dichloromethane (3×150 mL), dried over $Na_2SO_4$, filtered, concentrated to give product 1-(1-amino-6-fluoro-isoquinolin-4-yl)-ethanone oxime (0.75 g, 87%). LC/MS m/z=220 $[M+H]^+$.

Example 26

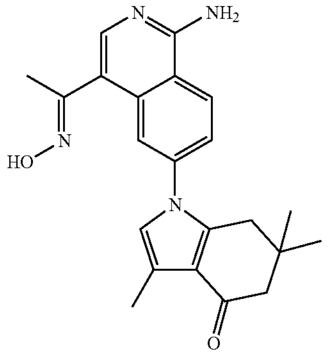

1-(1-amino-4-(1-(hydroxyimino)ethyl)isoquinolin-6-yl)-3,6,6-trimethyl-6,7-dihydro-1H-indol-4(5H)-one To 3,6,6,-trimethyl-1,5,6,7-tetrahydro-indol-4-one (0.104 g, 1.4 eq) in dimethylacetamide (3 mL), sodium hydride (14.4 mg, 1.4 eq) is added slowly and stirred at RT for 0.5 h. Then 1-(1-amino-6-fluoro-isoquinolin-4-yl)-ethanone oxime (90 mg, 1 eq) is added and the mixture is stirred at 150° C. overnight. The reaction is poured into Sat'd $NH_4Cl$ aq. (200 mL), extracted by EtOAc (3×100 mL), dried over $Na_2SO_4$, filtered, concentrated to give a crude product. That is purified by Biotage chromatography, eluted by 20% MeOH in DCM to give 1-(1-amino-4-(1-(hydroxyimino)ethyl)isoquinolin-6-yl)-3,6,6-trimethyl-6,7-dihydro-1H-indol-4(5H)-one (20 mg, 13%). LC/MS m/z=377 $[M+H]^+$.

Example 27

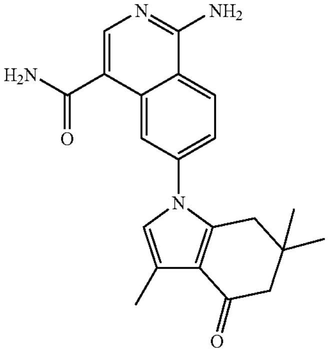

1-amino-6-(3,6,6-trimethyl-4-oxo-4,5,6,7-tetrahydro-indol-1-yl)-isoquinoline-4-carboxylic acid amide A suspension of 1-amino-6-(3,6,6-trimethyl-4-oxo-4,5,6,7-tetrahydro-indol-1-yl)-isoquinoline-4-carbonitrile (0.066 g, 0.19 mmol) in EtOH/DMSO (3:1, 2 mL) is treated with an aqueous solution of NaOH (1 M, 0.03 mL) and $H_2O_2$ (30%, 0.1 mL). The reaction mixture is stirred at RT for 2 h. The reaction mixture is treated with $H_2O$ (20 mL). The aqueous phase is extracted with EtOAc (2×). The combined organic layers are dried over $MgSO_4$. The solvent is evaporated and the residue is dried under vacuum. Purification of the crude material using a Biotage column (0-20% $MeOH/CH_2Cl_2$) affords 0.02 g (29%) of 1-amino-6-(3,6,6-trimethyl-4-oxo-4,5,6,7-tetrahydro-indol-1-yl)-isoquinoline-4-carboxylic acid amide. LC/MS m/z=363 $[M+H]^+$, RT=1.93 min.

Example 28

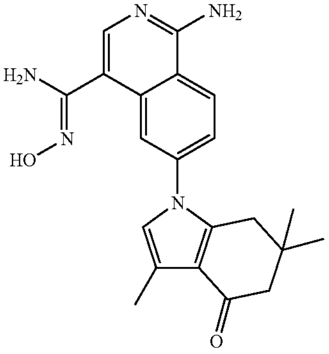

1-amino-N-hydroxy-6-(3,6,6-trimethyl-4-oxo-4,5,6,7-tetrahydro-indol-1-yl)-isoquinoline-4-carboxamidine A suspension of 1-amino-6-(3,6,6-trimethyl-4-oxo-4,5,6,7-tetrahydro-indol-1-yl)-isoquinoline-4-carbonitrile (0.035 g, 0.1 mmol), hydroxylamine (7 mg, 0.1 mmol) and triethylamine (0.01 mL, 0.1 mmol) in EtOH (2 mL) is placed in an oil bath at 100° C. and stirred for 2 days. The solvent is evaporated under reduced pressure, and the residue is purified using a Biotage column (0-20% $MeOH/CH_2Cl_2$) to afford 0.017 g (48%) of 1-amino-N-hydroxy-6-(3,6,6-trimethyl-4-oxo-4,5,6,7-tetrahydro-indol-1-yl)-isoquinoline-4-carboxamidine. LC/MS m/z=378 $[M+H]^+$, RT=1.82 min.

Example 29

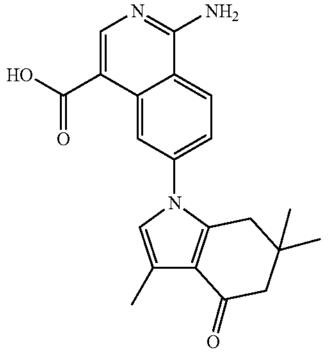

1-amino-6-(3,6,6-trimethyl-4-oxo-4,5,6,7-tetrahydro-indol-1-yl)-isoquinoline-4-carboxylic acid A solution of 1-amino-6-(3,6,6-trimethyl-4-oxo-4,5,6,7-tetrahydro-indol-1-yl)-isoquinoline-4-carbonitrile (0.15 g, 0.44 mmol) in THF (2 mL) and $H_2O$ (2 mL) is treated with concentrated HCl (10 mL). The reaction mixture is microwaved at 150° C. for 1.5 h. The reaction mixture is then treated with 5 M NaOH until pH=8. The crystals formed are collected by vacuum filtration, and dried to afford 0.07 g (44%) of 1-amino-6-(3,6,6-trimethyl-4-oxo-4,5,6,7-tetrahydro-indol-1-yl)-isoquinoline-4-carboxylic acid. LC/MS m/z=364 $[M+H]^+$, RT=2.12 min.

Example 30

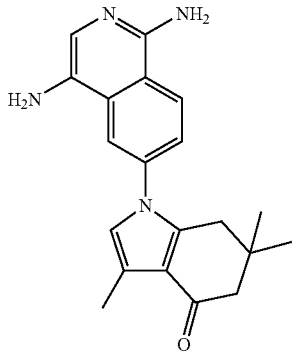

1-(1,4-diamino-isoquinolin-6-yl)-3,6,6-trimethyl-1,5,6,7-tetrahydro-indol-4-one

A solution of 1-[1-amino-4-(1-hydroxyimino-ethyl)-isoquinolin-6-yl]-3,6,6-trimethyl-1,5,6,7-tetrahydro-indol-4-one (5 mg, 0.03 mmol) in HCl (0.2 mL) and acetic acid (0.5 mL) is microwaved at 100° C. for 30 min. The reaction mixture is then treated with 1 M NaOH until pH=8. The aqueous phase is extracted with EtOAc (2×). The combined organic layers are dried over $MgSO_4$. The solvent is evaporated and the residue is dried under vacuum to afford 4.5 mg (100%) of product 1-(1,4-diamino-isoquinolin-6-yl)-3,6,6-trimethyl-1,5,6,7-tetrahydro-indol-4-one. LC/MS m/z=335 $[M+H]^+$, RT=2.10 min.

Example 31

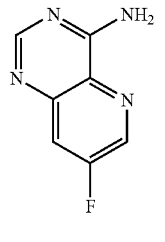

7-Fluoro-pyrido[3,2-d]pyrimidin-4-ylamine 3,5-Difluoro-pyridine-2-carbonitrile (2.54 mmol, 356 mg) is dissolved in DMA (5 mL) and then formamidine acetate is added (2.54 mmol, 264.6 mg) followed by DIEA (7.62 mmol, 983 mg). The reaction mixture is stirred for 16 h at 100° C., then poured into saturated $NH_4Cl$ aq. and extracted 3 times with $CH_2Cl_2$. The organics are dried with $Na_2SO_4$, concentrated, and purified on Biotage with 0-20% MeOH in $CH_2Cl_2$. This gives the desired product 7-Fluoro-pyrido[3,2-d]pyrimidin-4-ylamine (27 mg, LC/MS m/z=165 $[M+H]^+$) as a white powder.

Example 32

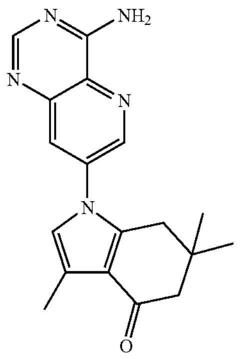

1-(4-Amino-pyrido[3,2-d]pyrimidin-7-yl)-3,6,6-trimethyl-1,5,6,7-tetrahydro-indol-4-one 3,6,6-Trimethyl-1,5,6,7-tetrahydro-indol-4-one (0.181, 32 mg) is dissolved in 1 mL DMF. To this solution is added sodium hydride (60% suspension in mineral oil, 0.229 mmol, 9.18 mg) and the mixture is stirred at rt for 5 min. and then 7-Fluoro-pyrido[3,2-d]pyrimidin-4-ylamine (0.164 mmol, 27 mg) is added. The reaction mixture is stirred at 50° C. for 22 h. The reaction mixture is cooled and quenched by pouring into 20 mL sat. $NH_4Cl$ aq. and extracted 3 times with 5 mL $CH_2Cl_2$. The combined organics are dried with $Na_2SO_4$, concentrated, and purified by silica gel chromatography on Biotage using a gradient of 0-15% MeOH in DCM. 1-(4-Amino-pyrido[3,2-d]pyrimidin-7-yl)-3,6,6-trimethyl-1,5,6,7-tetrahydro-indol-4-one is isolated (12 mg, LC/MS m/z=322 $[M+H]^+$) as a white powder.

Example 33

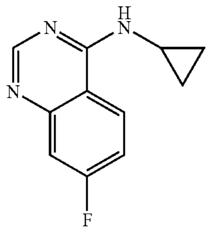

Cyclopropyl-(7-fluoro-quinazolin-4-yl)-amine

Formamidine acetate (31.2 g, 300 mmol) and 2-amino-4-fluorobenzoic acid (23.3 g, 150 mmol) are heated at reflux in ethoxyethanol for 16 h. The crude product is poured into saturate sodium bicarbonate solution. The solid is collected, washed, and dried, affording the titled 7-Fluoro-3H-quinazolin-4-one (21.8 g, 89%).

7-Fluoro-3H-quinazolin-4-one (8.2 g, 50 mmol) is heated at reflux in thionyl chloride (80 mL). Concentration affords the expected 4-Chloro-7-fluoro-quinazoline (9.1 g, ~quant).

4-Chloro-7-fluoro-quinazoline (0.73 g, 4 mmol) and cyclopropylamine (0.23 g, 4 mmol) are stirred in dichloromethane at ambient temperature overnight. The solid product is precipitated with hexanes, filtered, and washed with hexane and ethyl acetate, affording 0.3 g of desired Cyclopropyl-(7-fluoro-quinazolin-4-yl)-amine. The filtrate is concentrated and precipitated with hexanes, yielding an additional 0.35, for a combined yield of 80%. LC/MS m/z=204 $[M+H]^+$).

Example 34

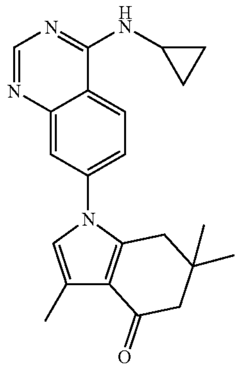

1-(4-Cyclopropylamino-quinazolin-7-yl)-3,6,6-trimethyl-1,5,6,7-tetrahydro-indol-4-one 3,6,6-Trimethyl-1,5,6,7-tetrahydro-indol-4-one (0.177 g, 1 mmol), sodium hydride (60% in oil, 40 mg, 1 mmol), Cyclopropyl-(7-fluoro-quinazolin-4-yl)-amine (0.20 g, 1 mmol), and N,N-dimethylformamide are sealed in a microwave vessel and irradiated at 100 degrees Celsius for 1500 seconds. The mixture is extracted with ethyl acetate and washed with water. The organic phase is dried over magnesium sulfate, filtered concentrated, and chromatographed to afford 0.2 g of 1-(4-Cyclopropylamino-quinazolin-7-yl)-3,6,6-trimethyl-1,5,6,7-tetrahydro-indol-4-one as a solid (55%). LC/MS m/z=361 $[M+H]^+$.

Example 35

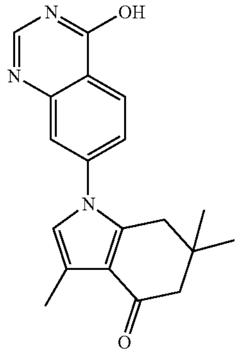

1-(4-hydroxyquinazolin-7-yl)-3,6,6-trimethyl-6,7-dihydro-1H-indol-4(5H)-one 1-(4-Amino-quinazolin-7-yl)-3,6,6-trimethyl-1,5,6,7-tetrahydro-indol-4-one (0.2 g 0.62 mmol) is microwaved at 80 degrees Celsius for 300 seconds in the presence of excess 36% HCl. The crude product is taken up in ethyl acetate/water. The organic phase is dried over magnesium sulfate, filtered, concentrated and chromatographed to afford 1-(4-hydroxyquinazolin-7-yl)-3,6,6-trimethyl-6,7-dihydro-1H-indol-4(5H)-one as a solid (0.12 g, 60%). LC/MS m/z=322 $[M+H]^+$.

Example 36

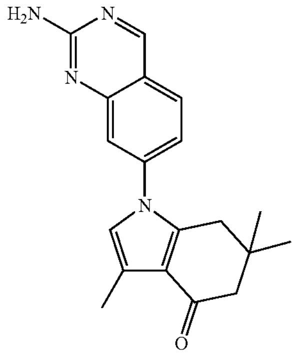

1-(2-Amino-quinazolin-7-yl)-3,6,6-trimethyl-1,5,6,7-tetrahydro-indol-4-one 2,4-difluorobenzaldehyde (4.26 g, 30 mmol), guanidine carbonate (5.40 g, 30 mmol), N,N-diisopropylethylamine (3.87 g, 30 mmol), and N,N-dimethylacetamide (25 mL) are heated at 160 degrees Celsius overnight. The crude product is taken up in ethyl acetate/water. The organic layer is dried over magnesium sulfate, then concentrated and subjected to chromatography, affording the desired 7-fluoroquinazolin-2-amine (0.95 g, 19%). LC/MS m/z=164 $[M+H]^+$.

3,6,6-Trimethyl-1,5,6,7-tetrahydro-indol-4-one (0.65 g, 3.68 mmol), sodium hydride (60% in oil, 0.177 g, 4.4 mmol), 7-fluoroquinazolin-2-amine (0.60 g, 3.68 mmol), and N,N-dimethylformamide are sealed in a microwave vessel and irradiated at 150 degrees Celsius for 1500 seconds. The mixture is purified by column chromatography and recrystallized from dichloromethane/hexane, affording 0.96 g of 1-(2-Amino-quinazolin-7-yl)-3,6,6-trimethyl-1,5,6,7-tetrahydro-indol-4-one (81%). LC/MS m/z=321 $[M+H]^+$.

Example 37

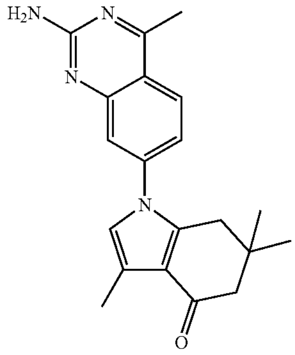

1-(2-Amino-4-methyl-quinazolin-7-yl)-3,6,6-trimethyl-1,5,6,7-tetrahydro-indol-4-one 2,4-Difluoroacetophenone (5 g, 32 mmol) and guanidine carbonate (8.65 g, 48 mmol) are heated at 140 degrees Celsius for 2 hours in N,N-dimethylacetamide (35 mL). The product is collected by ethyl acetate/water extraction, and the crude product is purified by column chromatography, affording 1.7 g of solid product 7-Fluoro-4-methyl-quinazolin-2-ylamine (30%). LC/MS m/z=178 $[M+H]^+$.

3,6,6-Trimethyl-1,5,6,7-tetrahydro-indol-4-one (0.7 g, 4 mmol), sodium hydride (60% in oil, 0.20 g, 4.8 mmol), 7-Fluoro-4-methyl-quinazolin-2-ylamine (0.7 g, 4 mmol), and N,N-dimethylformamide are heated at 150 degrees Celsius for 2 h. The mixture is extracted with ethyl acetate/water. The organic layer is dried and concentrated. The residue is purified by column chromatography, affording 0.9 g of a solid 1-(2-Amino-4-methyl-quinazolin-7-yl)-3,6,6-trimethyl-1,5,6,7-tetrahydro-indol-4-one (68%). LC/MS m/z=335 $[M+H]^+$.

Example 38

The following compounds are prepared essentially according to the procedures set forth in the above schemes and detailed in the preceding examples.

| Compound No. | Structure | Name | $[M + H]^+$ |
|---|---|---|---|
| 38 | 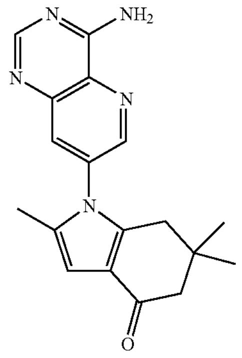 | 1-(4-aminopyrido[3,2-d]pyrimidin-7-yl)-2,6,6-trimethyl-6,7-dihydro-1H-indol-4(5H)-one | 322 |
| 39 | 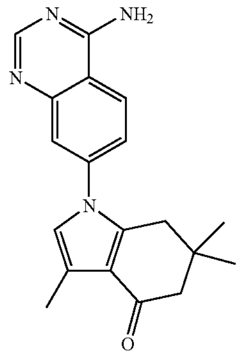 | 1-(4-aminoquinazolin-7-yl)-3,6,6-trimethyl-6,7-dihydro-1H-indol-4(5H)-one | 321 |
| 40 | 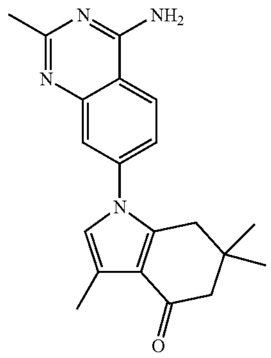 | 1-(4-amino-2-methylquinazolin-7-yl)-3,6,6-trimethyl-6,7-dihydro-1H-indol-4(5H)-one | 335 |

-continued
| Compound No. | Structure | Name | [M + H]$^+$ |
|---|---|---|---|
| 41 | 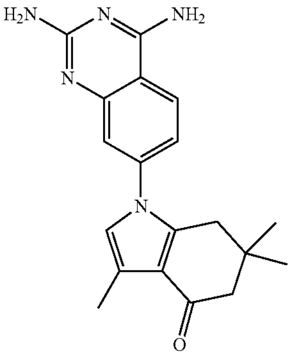 | 1-(2,4-diaminoquinazolin-7-yl)-3,6,6-trimethyl-6,7-dihydro-1H-indol-4(5H)-one | 336 |
| 42 | 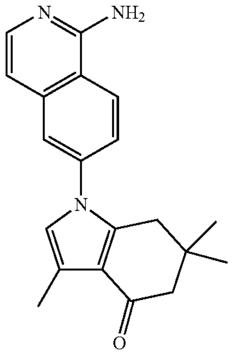 | 1-(1-aminoisoquinolin-6-yl)-3,6,6-trimethyl-6,7-dihydro-1H-indol-4(5H)-one | 320 |
| 43 | 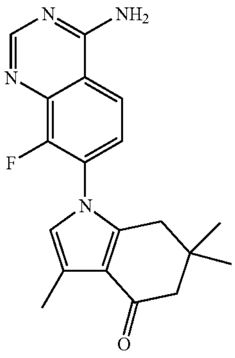 | 1-(4-amino-8-fluoroquinazolin-7-yl)-3,6,6-trimethyl-6,7-dihydro-1H-indol-4(5H)-one | 339 |
| 44 | 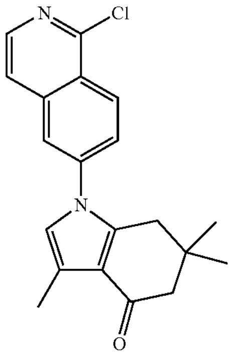 | 1-(1-chloroisoquinolin-6-yl)-3,6,6-trimethyl-6,7-dihydro-1H-indol-4(5H)-one | 339 |

-continued
| Compound No. | Structure | Name | [M + H]$^+$ |
|---|---|---|---|
| 45 | 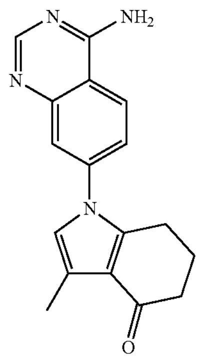 | 1-(4-aminoquinazolin-7-yl)-3-methyl-6,7-dihydro-1H-indol-4(5H)-one | 293 |
| 46 | 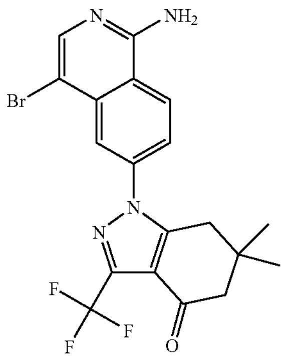 | 1-(1-amino-4-bromoisoquinolin-6-yl)-6,6-dimethyl-3-(trifluoromethyl)-6,7-dihydro-1H-indazol-4(5H)-one | 453 |
| 47 | 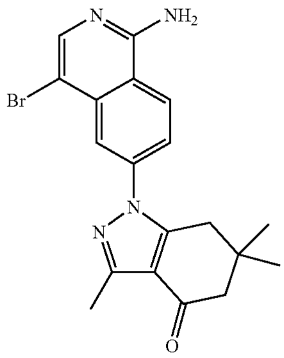 | 1-(1-amino-4-bromoisoquinolin-6-yl)-3,6,6-trimethyl-6,7-dihydro-1H-indazol-4(5H)-one | 399 |
| 48 | 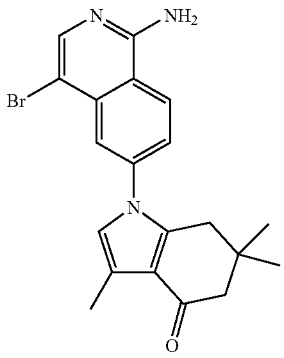 | 1-(1-amino-4-bromoisoquinolin-6-yl)-3,6,6-trimethyl-6,7-dihydro-1H-indol-4(5H)-one | 398 |

-continued
| Compound No. | Structure | Name | [M + H]$^+$ |
|---|---|---|---|
| 49 | 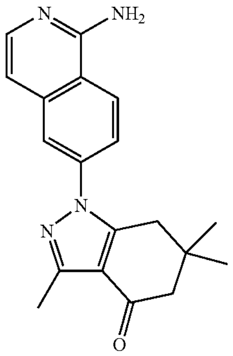 | 1-(1-aminoisoquinolin-6-yl)-3,6,6-trimethyl-6,7-dihydro-1H-indazol-4(5H)-one | 321 |
| 50 | 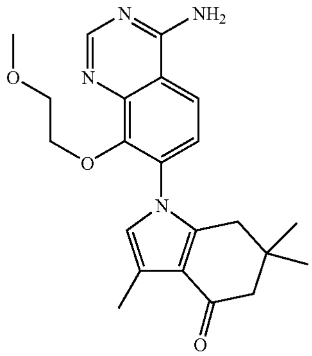 | 1-(4-amino-8-(2-methoxyethoxy)quinazolin-7-yl)-3,6,6-trimethyl-6,7-dihydro-1H-indol-4(5H)-one | 395 |
| 51 | 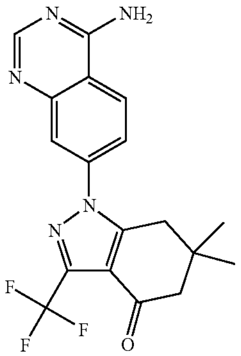 | 1-(4-aminoquinazolin-7-yl)-6,6-dimethyl-3-(trifluoromethyl)-6,7-dihydro-1H-indazol-4(5H)-one | 376 |
| 52 | 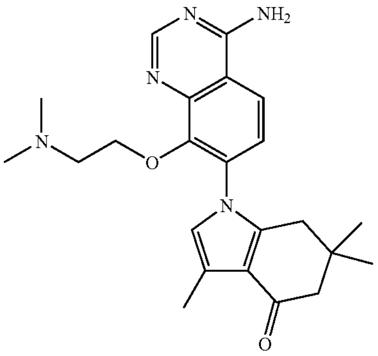 | 1-(4-amino-8-(2-(dimethylamino)ethoxy)quinazolin-7-yl)-3,6,6-trimethyl-6,7-dihydro-1H-indol-4(5H)-one | 408 |

-continued
| Compound No. | Structure | Name | [M + H]$^+$ |
|---|---|---|---|
| 53 | 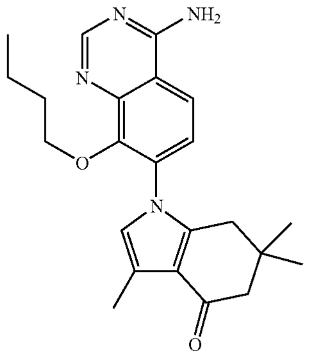 | 1-(4-amino-8-butoxyquinazolin-7-yl)-3,6,6-trimethyl-6,7-dihydro-1H-indol-4(5H)-one | 393 |
| 54 | 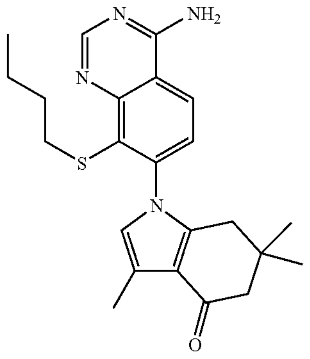 | 1-(4-amino-8-(butylthio)quinazolin-7-yl)-3,6,6-trimethyl-6,7-dihydro-1H-indol-4(5H)-one | 409 |
| 55 | 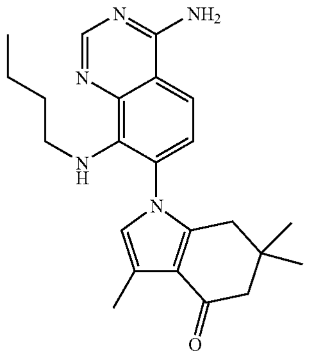 | 1-(4-amino-8-(butylamino)quinazolin-7-yl)-3,6,6-trimethyl-6,7-dihydro-1H-indol-4(5H)-one | 392 |
| 56 | 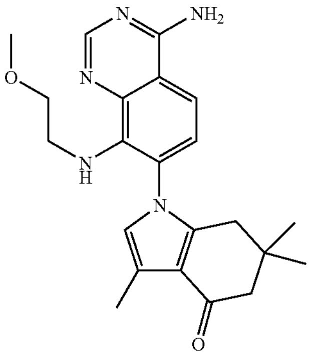 | 1-(4-amino-8-(2-methoxyethylamino)quinazolin-7-yl)-3,6,6-trimethyl-6,7-dihydro-1H-indol-4(5H)-one | 394 |

-continued
| Compound No. | Structure | Name | [M + H]$^+$ |
|---|---|---|---|
| 57 | 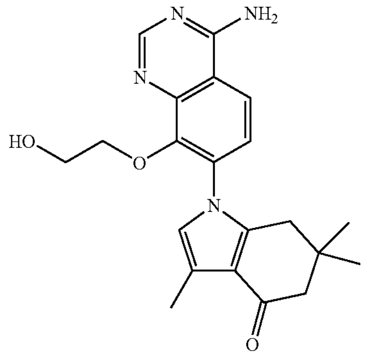 | 1-(4-amino-8-(2-hydroxyethoxy)quinazolin-7-yl)-3,6,6-trimethyl-6,7-dihydro-1H-indol-4(5H)-one | 381 |
| 58 | 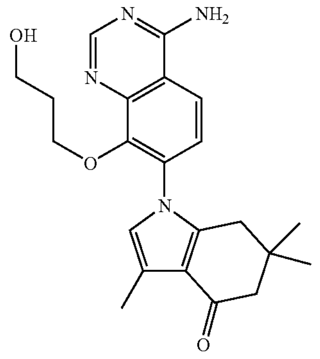 | 1-(4-amino-8-(3-hydroxypropoxy)quinazolin-7-yl)-3,6,6-trimethyl-6,7-dihydro-1H-indol-4(5H)-one | 395 |
| 59 | 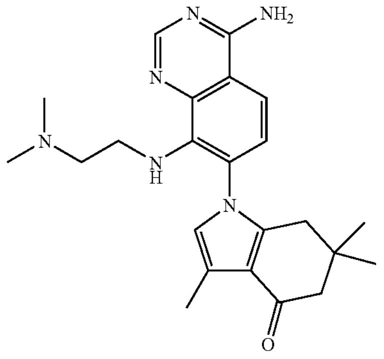 | 1-(4-amino-8-(2-(dimethylamino)ethylamino)quinazolin-7-yl)-3,6,6-trimethyl-6,7-dihydro-1H-indol-4(5H)-one | 406 |
| 60 | 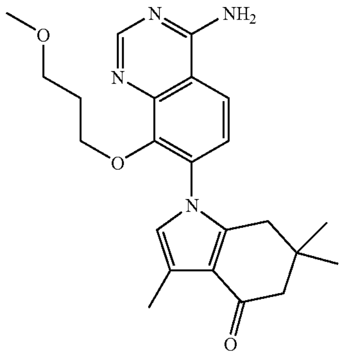 | 1-(4-amino-8-(3-methoxypropoxy)quinazolin-7-yl)-3,6,6-trimethyl-6,7-dihydro-1H-indol-4(5H)-one | 409 |

-continued
| Compound No. | Structure | Name | [M + H]$^+$ |
|---|---|---|---|
| 61 | 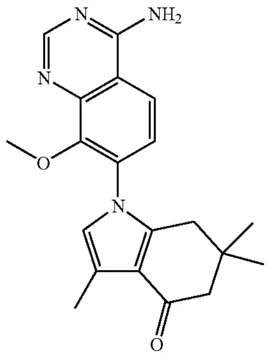 | 1-(4-amino-8-methoxyquinazolin-7-yl)-3,6,6-trimethyl-6,7-dihydro-1H-indol-4(5H)-one | 351 |
| 62 | 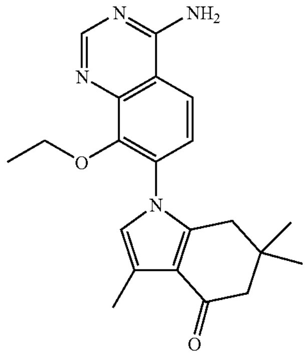 | 1-(4-amino-8-ethoxyquinazolin-7-yl)-3,6,6-trimethyl-6,7-dihydro-1H-indol-4(5H)-one | 365 |
| 63 | 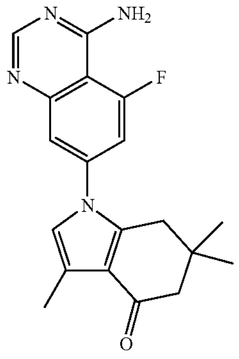 | 1-(4-amino-5-fluoroquinazolin-7-yl)-3,6,6-trimethyl-6,7-dihydro-1H-indol-4(5H)-one | 339 |
| 64 | 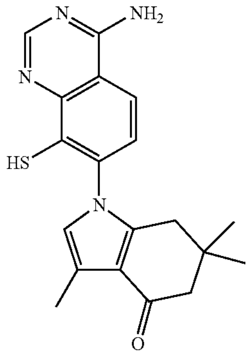 | 1-(4-amino-8-mercaptoquinazolin-7-yl)-3,6,6-trimethyl-6,7-dihydro-1H-indol-4(5H)-one | 353 |

-continued
| Compound No. | Structure | Name | [M + H]$^+$ |
|---|---|---|---|
| 65 | 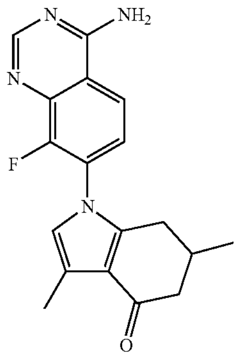 | 1-(4-amino-8-fluoroquinazolin-7-yl)-3,6-dimethyl-6,7-dihydro-1H-indol-4(5H)-one | 325 |
| 66 | 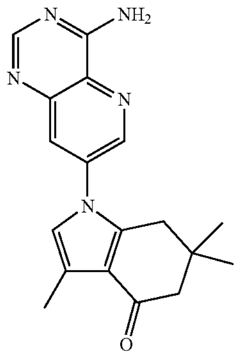 | 1-(4-aminopyrido[3,2-d]pyrimidin-7-yl)-3,6,6-trimethyl-6,7-dihydro-1H-indol-4(5H)-one | 322 |
| 67 | 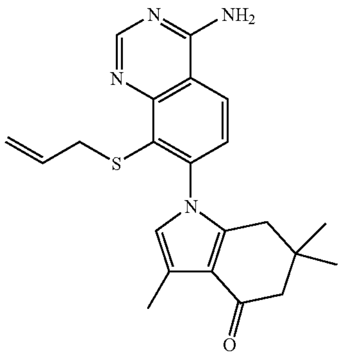 | 1-(8-(allylthio)-4-aminoquinazolin-7-yl)-3,6,6-trimethyl-6,7-dihydro-1H-indol-4(5H)-one | 393 |
| 68 | 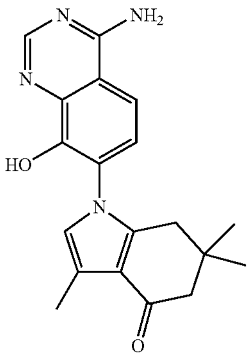 | 1-(4-amino-8-hydroxyquinazolin-7-yl)-3,6,6-trimethyl-6,7-dihydro-1H-indol-4(5H)-one | 337 |

-continued
| Compound No. | Structure | Name | [M + H]+ |
|---|---|---|---|
| 69 | 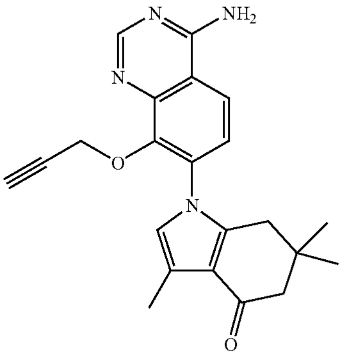 | 1-(4-amino-8-(prop-2-ynyloxy)quinazolin-7-yl)-3,6,6-trimethyl-6,7-dihydro-1H-indol-4(5H)-one | 375 |
| 70 | 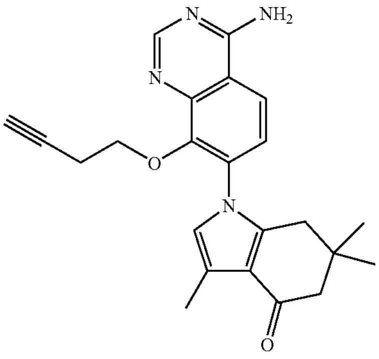 | 1-(4-amino-8-(but-3-ynyloxy)quinazolin-7-yl)-3,6,6-trimethyl-6,7-dihydro-1H-indol-4(5H)-one | 389 |
| 71 | 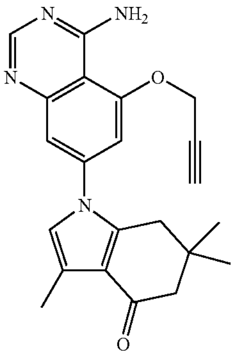 | 1-(4-amino-5-(prop-2-ynyloxy)quinazolin-7-yl)-3,6,6-trimethyl-6,7-dihydro-1H-indol-4(5H)-one | 375 |
| 72 | 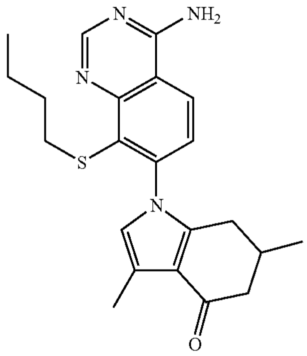 | 1-(4-amino-8-(butylthio)quinazolin-7-yl)-3,6-dimethyl-6,7-dihydro-1H-indol-4(5H)-one | 395 |

-continued
| Compound No. | Structure | Name | [M + H]$^+$ |
|---|---|---|---|
| 73 | 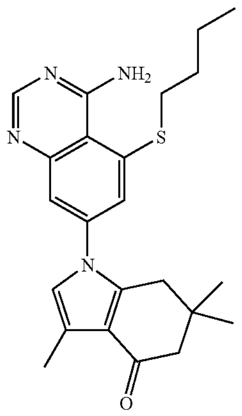 | 1-(4-amino-5-(butylthio)quinazolin-7-yl)-3,6,6-trimethyl-6,7-dihydro-1H-indol-4(5H)-one | 409 |
| 74 | 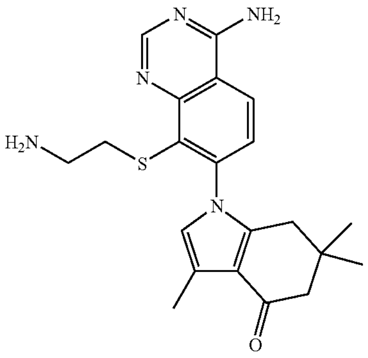 | 1-(4-amino-8-(2-aminoethylthio)quinazolin-7-yl)-3,6,6-trimethyl-6,7-dihydro-1H-indol-4(5H)-one | 396 |
| 75 | 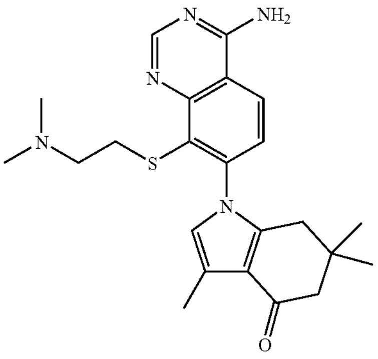 | 1-(4-amino-8-(2-(dimethylamino)ethylthio)quinazolin-7-yl)-3,6,6-trimethyl-6,7-dihydro-1H-indol-4(5H)-one | 424 |
| 76 | 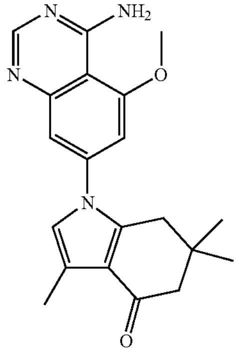 | 1-(4-amino-5-methoxyquinazolin-7-yl)-3,6,6-trimethyl-6,7-dihydro-1H-indol-4(5H)-one | 351 |

-continued
| Compound No. | Structure | Name | [M + H]+ |
|---|---|---|---|
| 77 | 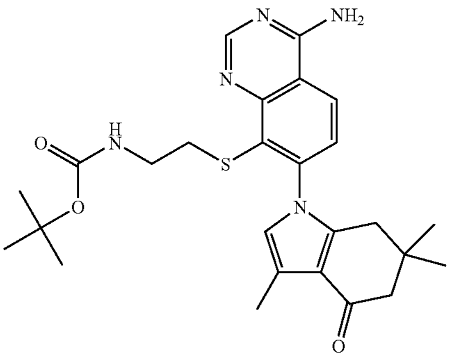 | tert-butyl 2-(4-amino-7-(3,6,6-trimethyl-4-oxo-4,5,6,7-tetrahydro-1H-indol-1-yl)quinazolin-8-ylthio)ethylcarbamate | 496 |
| 78 | 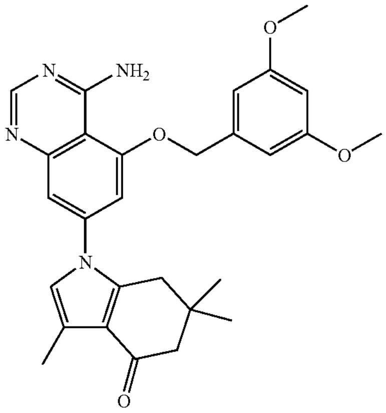 | 1-(4-amino-5-(3,5-dimethoxybenzyloxy) quinazolin-7-yl)-3,6,6-trimethyl-6,7-dihydro-1H-indol-4(5H)-one | 487 |
| 79 | 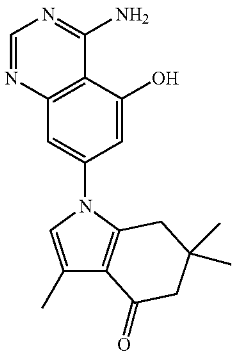 | 1-(4-amino-5-hydroxyquinazolin-7-yl)-3,6,6-trimethyl-6,7-dihydro-1H-indol-4(5H)-one | 337 |
| 80 | 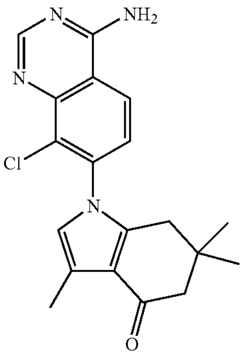 | 1-(4-amino-8-chloroquinazolin-7-yl)-3,6,6-trimethyl-6,7-dihydro-1H-indol-4(5H)-one | 355 |

-continued
| Compound No. | Structure | Name | [M + H]+ |
|---|---|---|---|
| 81 | 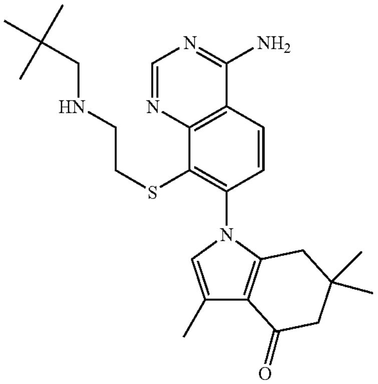 | 1-(4-amino-8-(2-(neopentylamino)ethylthio)quinazolin-7-yl)-3,6,6-trimethyl-6,7-dihydro-1H-indol-4(5H)-one | 466 |
| 82 | 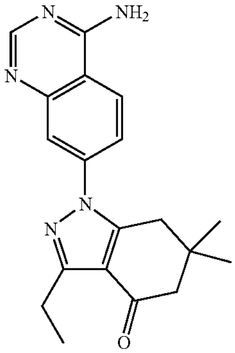 | 1-(4-aminoquinazolin-7-yl)-3-ethyl-6,6-dimethyl-6,7-dihydro-1H-indazol-4(5H)-one | 336 |
| 83 | 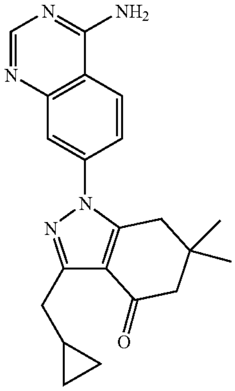 | 1-(4-aminoquinazolin-7-yl)-3-(cyclopropylmethyl)-6,6-dimethyl-6,7-dihydro-1H-indazol-4(5H)-one | 362 |
| 84 | 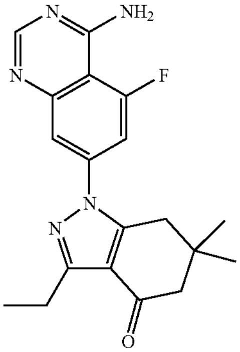 | 1-(4-amino-5-fluoroquinazolin-7-yl)-3-ethyl-6,6-dimethyl-6,7-dihydro-1H-indazol-4(5H)-one | 354 |

-continued
| Compound No. | Structure | Name | [M + H]$^+$ |
| --- | --- | --- | --- |
| 85 | 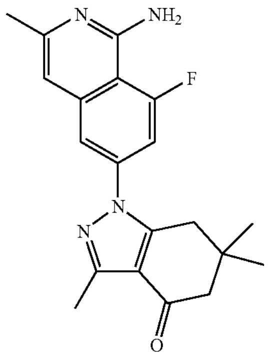 | 1-(1-amino-8-fluoro-3-methylisoquinolin-6-yl)-3,6,6-trimethyl-6,7-dihydro-1H-indazol-4(5H)-one | 353 |
| 86 | 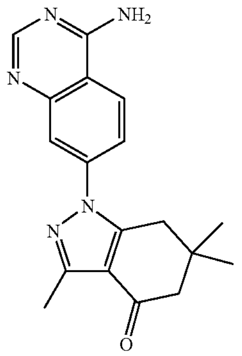 | 1-(4-aminoquinazolin-7-yl)-3,6,6-trimethyl-6,7-dihydro-1H-indazol-4(5H)-one | 322 |
| 87 | 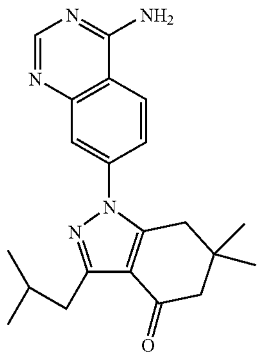 | 1-(4-aminoquinazolin-7-yl)-3-isobutyl-6,6-dimethyl-6,7-dihydro-1H-indazol-4(5H)-one | 364 |
| 88 | 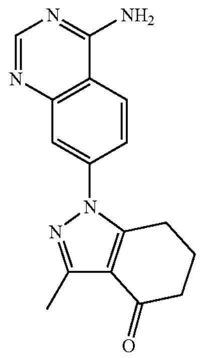 | 1-(4-aminoquinazolin-7-yl)-3-methyl-6,7-dihydro-1H-indazol-4(5H)-one | 294 |

-continued
| Compound No. | Structure | Name | [M + H]+ |
| --- | --- | --- | --- |
| 89 | 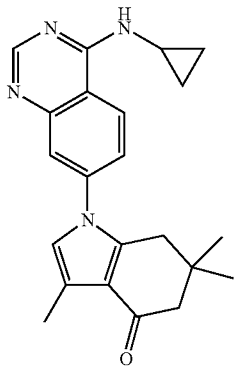 | 1-(4-(cyclopropylamino)quinazolin-7-yl)-3,6,6-trimethyl-6,7-dihydro-1H-indol-4(5H)-one | 361 |
| 90 | 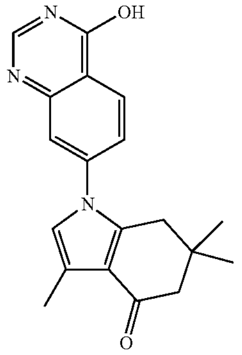 | 1-(4-hydroxyquinazolin-7-yl)-3,6,6-trimethyl-6,7-dihydro-1H-indol-4(5H)-one | 322 |
| 91 | 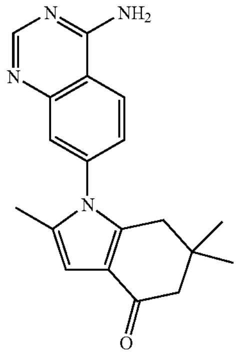 | 1-(4-aminoquinazolin-7-yl)-2,6,6-trimethyl-6,7-dihydro-1H-indol-4(5H)-one | 321 |
| 92 | 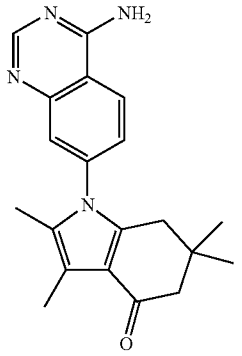 | 1-(4-aminoquinazolin-7-yl)-2,3,6,6-tetramethyl-6,7-dihydro-1H-indol-4(5H)-one | 335 |

-continued
| Compound No. | Structure | Name | [M + H]$^+$ |
|---|---|---|---|
| 93 | 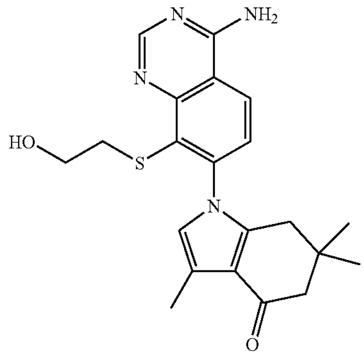 | 1-(4-amino-8-(2-hydroxyethylthio)quinazolin-7-yl)-3,6,6-trimethyl-6,7-dihydro-1H-indol-4(5H)-one | 397 |
| 94 | 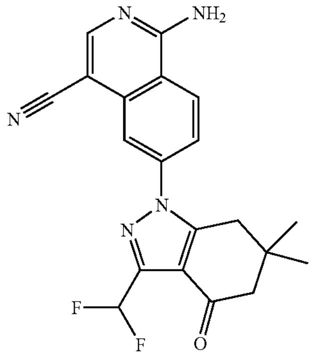 | 1-amino-6-(3-(difluoromethyl)-6,6-dimethyl-4-oxo-4,5,6,7-tetrahydro-1H-indazol-1-yl)isoquinoline-4-carbonitrile | 382 |
| 95 | 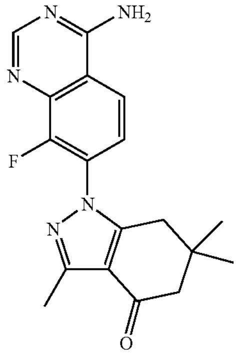 | 1-(4-amino-8-fluoroquinazolin-7-yl)-3,6,6-trimethyl-6,7-dihydro-1H-indazol-4(5H)-one | 340 |
| 96 | 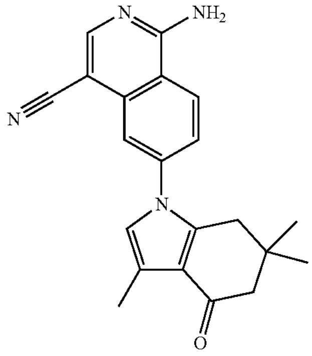 | 1-amino-6-(3,6,6-trimethyl-4-oxo-4,5,6,7-tetrahydro-1H-indol-1-yl)isoquinoline-4-carbonitrile | 345 |

-continued
| Compound No. | Structure | Name | [M + H]$^+$ |
|---|---|---|---|
| 97 | 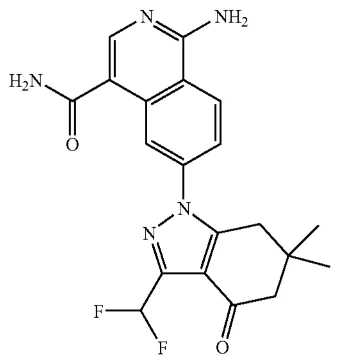 | 1-amino-6-(3-(difluoromethyl)-6,6-dimethyl-4-oxo-4,5,6,7-tetrahydro-1H-indazol-1-yl)isoquinoline-4-carboxamide | 400 |
| 98 | 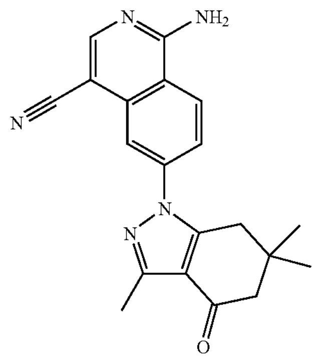 | 1-amino-6-(3,6,6-trimethyl-4-oxo-4,5,6,7-tetrahydro-1H-indazol-1-yl)isoquinoline-4-carbonitrile | 346 |
| 99 | 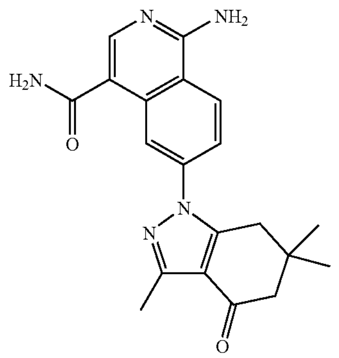 | 1-amino-6-(3,6,6-trimethyl-4-oxo-4,5,6,7-tetrahydro-1H-indazol-1-yl)isoquinoline-4-carboxamide | 364 |
| 100 | 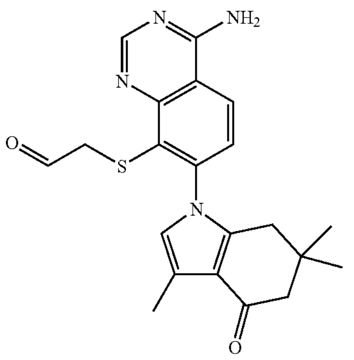 | 2-(4-amino-7-(3,6,6-trimethyl-4-oxo-4,5,6,7-tetrahydro-1H-indol-1-yl)quinazolin-8-ylthio)acetaldehyde | 395 |

-continued
| Compound No. | Structure | Name | [M + H]+ |
| --- | --- | --- | --- |
| 101 | 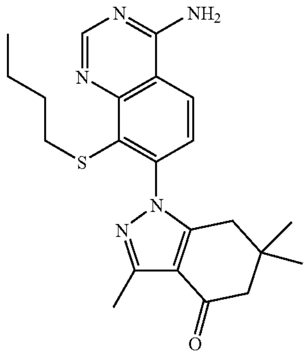 | 1-(4-amino-8-(butylthio)quinazolin-7-yl)-3,6,6-trimethyl-6,7-dihydro-1H-indazol-4(5H)-one | 410 |
| 102 | 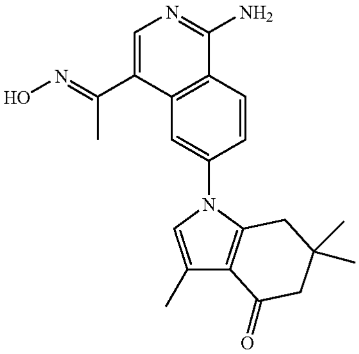 | (E)-1-(1-amino-4-(1-(hydroxyimino)ethyl)isoquinolin-6-yl)-3,6,6-trimethyl-6,7-dihydro-1H-indol-4(5H)-one | 377 |
| 103 | 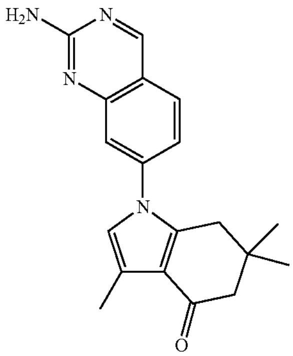 | 1-(2-aminoquinazolin-7-yl)-3,6,6-trimethyl-6,7-dihydro-1H-indol-4(5H)-one | 321 |
| 104 | 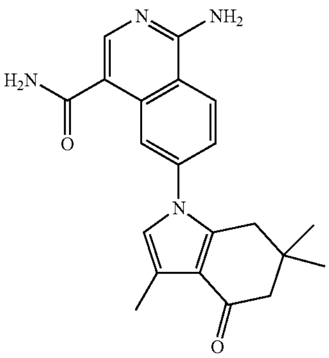 | 1-amino-6-(3,6,6-trimethyl-4-oxo-4,5,6,7-tetrahydro-1H-indol-1-yl)isoquinoline-4-carboxamide | 363 |

-continued
| Compound No. | Structure | Name | [M + H]+ |
|---|---|---|---|
| 105 | 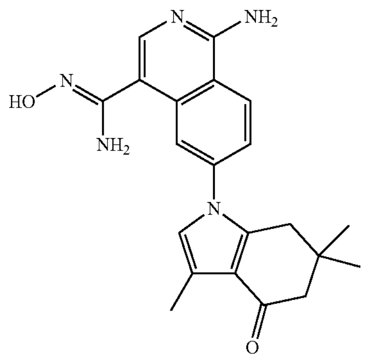 | (Z)-1-amino-N'-hydroxy-6-(3,6,6-trimethyl-4-oxo-4,5,6,7-tetrahydro-1H-indol-1-yl)isoquinoline-4-carboximidamide | 378 |
| 106 | 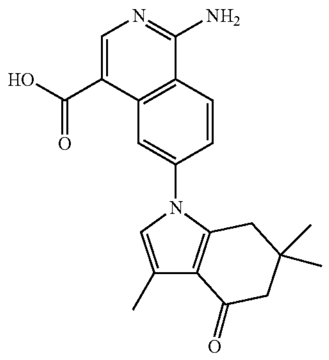 | 1-amino-6-(3,6,6-trimethyl-4-oxo-4,5,6,7-tetrahydro-1H-indol-1-yl)isoquinoline-4-carboxylic acid | 364 |
| 107 | 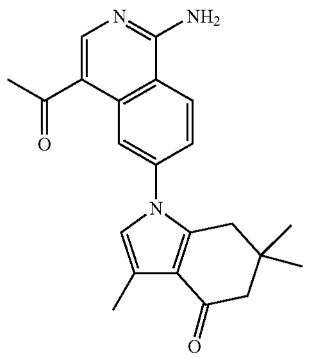 | 1-(4-acetyl-1-aminoisoquinolin-6-yl)-3,6,6-trimethyl-6,7-dihydro-1H-indol-4(5H)-one | 362 |
| 108 | 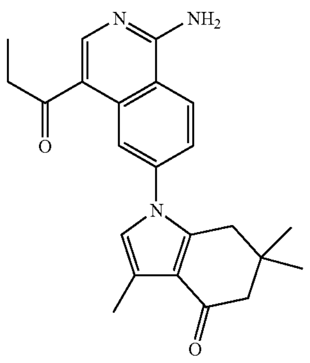 | 1-(1-amino-4-propionylisoquinolin-6-yl)-3,6,6-trimethyl-6,7-dihydro-1H-indol-4(5H)-one | 376 |

-continued

| Compound No. | Structure | Name | [M + H]$^+$ |
| --- | --- | --- | --- |
| 109 | 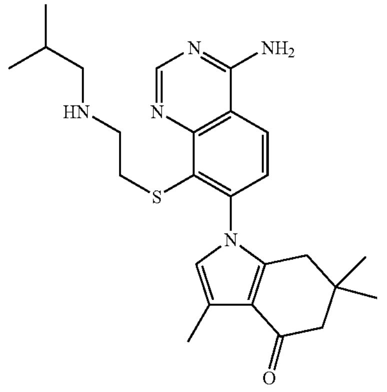 | 1-(4-amino-8-(2-(isobutylamino)ethylthio)quinazolin-7-yl)-3,6,6-trimethyl-6,7-dihydro-1H-indol-4(5H)-one | 452 |
| 110 | 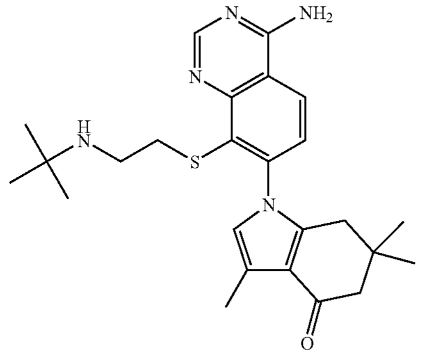 | 1-(4-amino-8-(2-(tert-butylamino)ethylthio)quinazolin-7-yl)-3,6,6-trimethyl-6,7-dihydro-1H-indol-4(5H)-one | 452 |
| 111 | 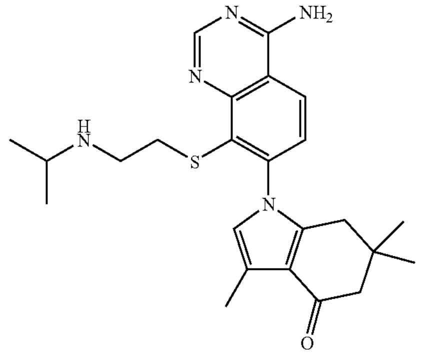 | 1-(4-amino-8-(2-(isopropylamino)ethylthio)quinazolin-7-yl)-3,6,6-trimethyl-6,7-dihydro-1H-indol-4(5H)-one | 438 |
| 112 | 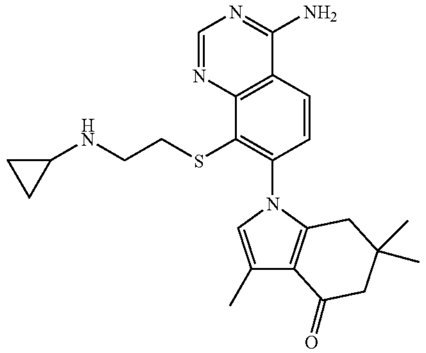 | 1-(4-amino-8-(2-(cyclopropylamino)ethylthio)quinazolin-7-yl)-3,6,6-trimethyl-6,7-dihydro-1H-indol-4(5H)-one | 436 |

-continued

| Compound No. | Structure | Name | $[M + H]^+$ |
|---|---|---|---|
| 113 | 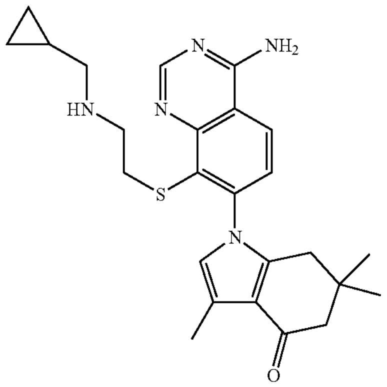 | 1-(4-amino-8-(2-(cyclopropylmethylamino)ethylthio)quinazolin-7-yl)-3,6,6-trimethyl-6,7-dihydro-1H-indol-4(5H)-one | 450 |
| 114 | 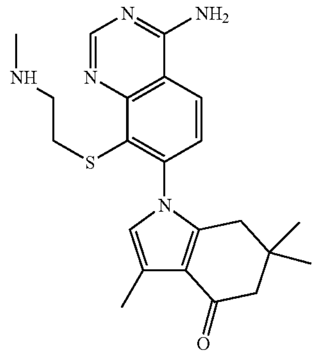 | 1-(4-amino-8-(2-(methylamino)ethylthio)quinazolin-7-yl)-3,6,6-trimethyl-6,7-dihydro-1H-indol-4(5H)-one | 410 |
| 115 | 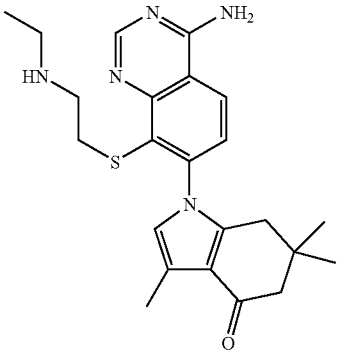 | 1-(4-amino-8-(2-(ethylamino)ethylthio)quinazolin-7-yl)-3,6,6-trimethyl-6,7-dihydro-1H-indol-4(5H)-one | 424 |
| 116 | 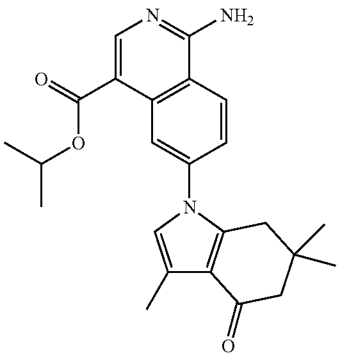 | isopropyl 1-amino-6-(3,6,6-trimethyl-4-oxo-4,5,6,7-tetrahydro-1H-indol-1-yl)isoquinoline-4-carboxylate | 406 |

-continued
| Compound No. | Structure | Name | [M + H]$^+$ |
|---|---|---|---|
| 117 | 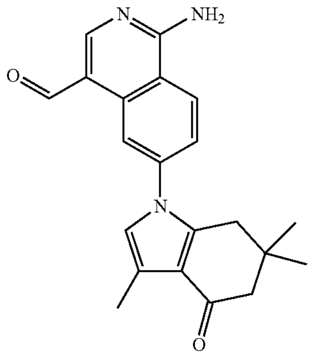 | 1-amino-6-(3,6,6-trimethyl-4-oxo-4,5,6,7-tetrahydro-1H-indol-1-yl)isoquinoline-4-carbaldehyde | 348 |
| 118 | 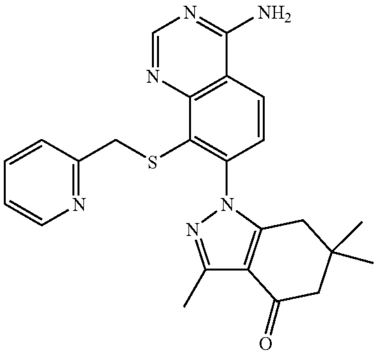 | 1-(4-amino-8-(pyridin-2-ylmethylthio)quinazolin-7-yl)-3,6,6-trimethyl-6,7-dihydro-1H-indazol-4(5H)-one | 445 |
| 119 | 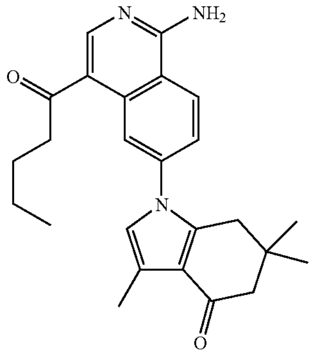 | 1-(1-amino-4-pentanoylisoquinolin-6-yl)-3,6,6-trimethyl-6,7-dihydro-1H-indol-4(5H)-one | 404 |
| 120 | 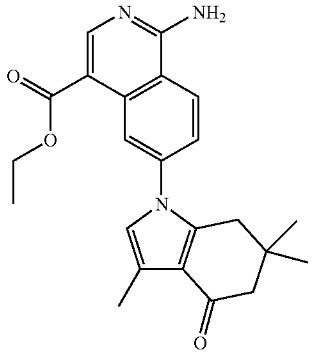 | ethyl 1-amino-6-(3,6,6-trimethyl-4-oxo-4,5,6,7-tetrahydro-1H-indol-1-yl)isoquinoline-4-carboxylate | 392 |

-continued
| Compound No. | Structure | Name | [M + H]+ |
| --- | --- | --- | --- |
| 121 | 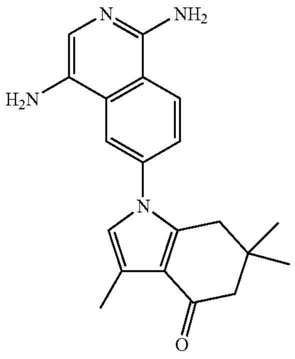 | 1-(1,4-diaminoisoquinolin-6-yl)-3,6,6-trimethyl-6,7-dihydro-1H-indol-4(5H)-one | 335 |
| 122 | 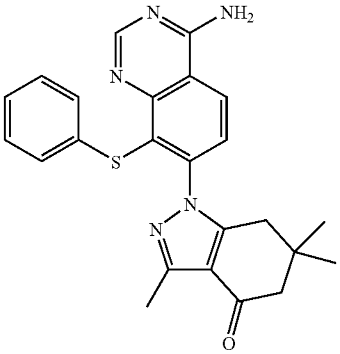 | 1-(4-amino-8-(phenylthio)quinazolin-7-yl)-3,6,6-trimethyl-6,7-dihydro-1H-indol-4(5H)-one | 429 |
| 123 | 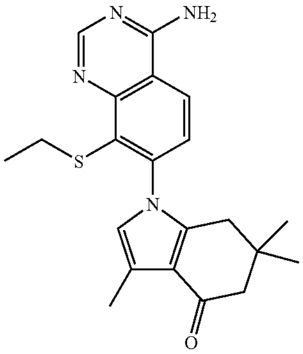 | 1-(4-amino-8-(ethylthio)quinazolin-7-yl)-3,6,6-trimethyl-6,7-dihydro-1H-indol-4(5H)-one | 381 |
| 124 | 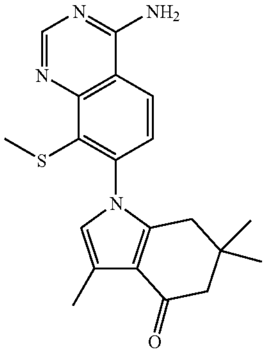 | 1-(4-amino-8-(methylthio)quinazolin-7-yl)-3,6,6-trimethyl-6,7-dihydro-1H-indol-4(5H)-one | 367 |

-continued
| Compound No. | Structure | Name | [M + H]$^+$ |
|---|---|---|---|
| 125 | 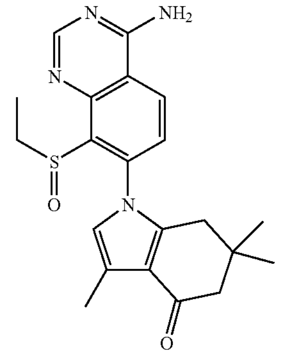 | 1-(4-amino-8-(ethylsulfinyl)quinazolin-7-yl)-3,6,6-trimethyl-6,7-dihydro-1H-indol-4(5H)-one | 397 |
| 126 | 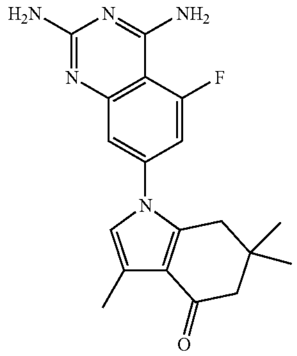 | 1-(2,4-diamino-5-fluoroquinazolin-7-yl)-3,6,6-trimethyl-6,7-dihydro-1H-indol-4(5H)-one | 354 |
| 127 | 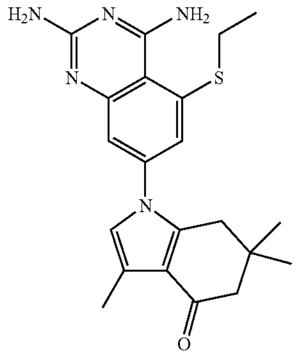 | 1-(2,4-diamino-5-(ethylthio)quinazolin-7-yl)-3,6,6-trimethyl-6,7-dihydro-1H-indol-4(5H)-one | 396 |
| 128 | 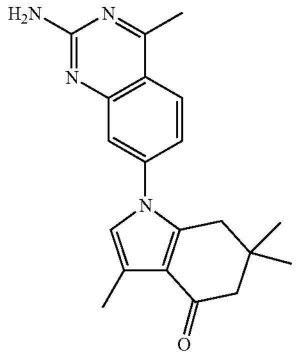 | 1-(2-amino-4-methylquinazolin-7-yl)-3,6,6-trimethyl-6,7-dihydro-1H-indol-4(5H)-one | 335 |

-continued
| Compound No. | Structure | Name | [M + H]$^+$ |
| --- | --- | --- | --- |
| 129 | 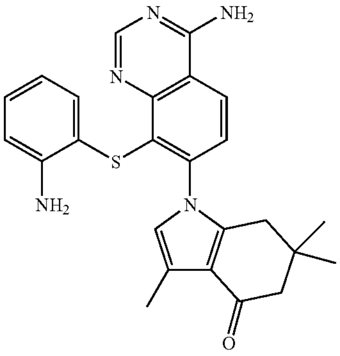 | 1-(4-amino-8-(2-aminophenylthio)quinazolin-7-yl)-3,6,6-trimethyl-6,7-dihydro-1H-indol-4(5H)-one | 444 |
| 130 | 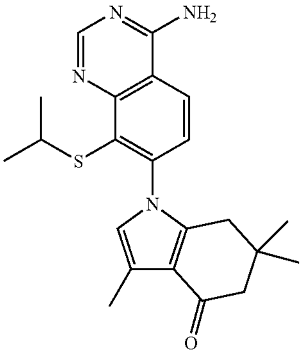 | 1-(4-amino-8-(isopropylthio)quinazolin-7-yl)-3,6,6-trimethyl-6,7-dihydro-1H-indol-4(5H)-one | 395 |
| 131 | 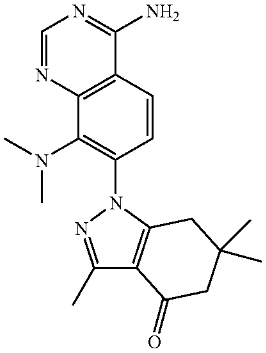 | 1-(4-amino-8-(dimethylamino)quinazolin-7-yl)-3,6,6-trimethyl-6,7-dihydro-1H-indol-4(5H)-one | 364 |
| 132 | 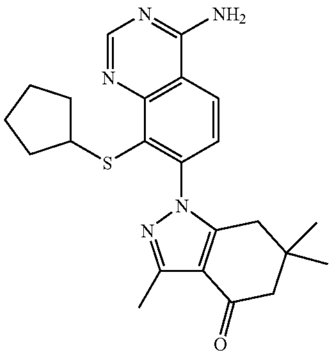 | 1-(4-amino-8-(cyclopentylthio)quinazolin-7-yl)-3,6,6-trimethyl-6,7-dihydro-1H-indol-4(5H)-one | 421 |

-continued
| Compound No. | Structure | Name | [M + H]$^+$ |
|---|---|---|---|
| 133 | 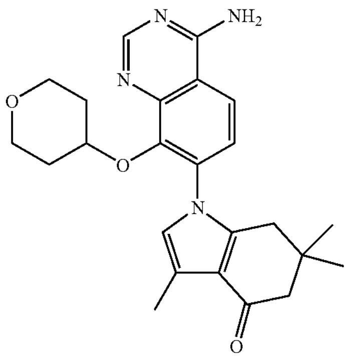 | 1-(4-amino-8-(tetrahydro-2H-pyran-4-yloxy)quinazolin-7-yl)-3,6,6-trimethyl-6,7-dihydro-1H-indol-4(5H)-one | 421 |
| 134 | 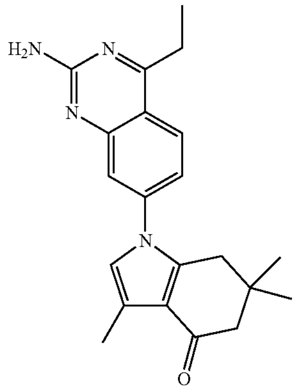 | 1-(2-amino-4-ethylquinazolin-7-yl)-3,6,6-trimethyl-6,7-dihydro-1H-indol-4(5H)-one | 349 |
| 135 | 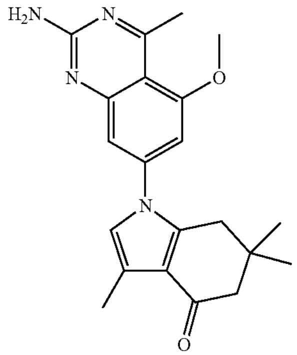 | 1-(2-amino-5-methoxy-4-methylquinazolin-7-yl)-3,6,6-trimethyl-6,7-dihydro-1H-indol-4(5H)-one | 365 |
| 136 | 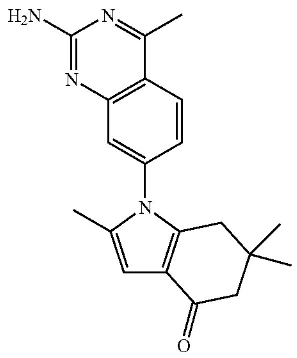 | 1-(2-amino-4-methylquinazolin-7-yl)-2,6,6-trimethyl-6,7-dihydro-1H-indol-4(5H)-one | 335 |

-continued
| Compound No. | Structure | Name | [M + H]+ |
|---|---|---|---|
| 137 | 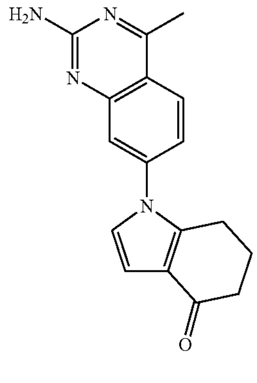 | 1-(2-amino-4-methylquinazolin-7-yl)-6,7-dihydro-1H-indol-4(5H)-one | 293 |
| 138 | 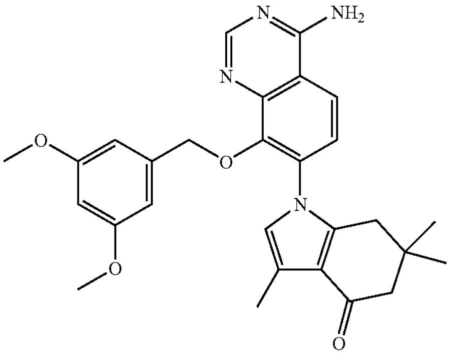 | 1-(4-amino-8-(3,5-dimethoxybenzyloxy)quinazolin-7-yl)-3,6,6-trimethyl-6,7-dihydro-1H-indol-4(5H)-one | 487 |
| 139 | 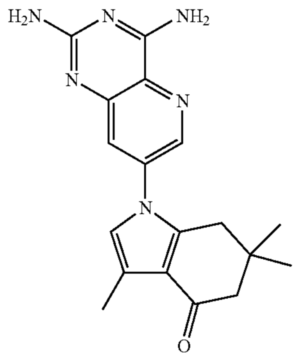 | 1-(2,4-diaminopyrido[3,2-d]pyrimidin-7-yl)-3,6,6-trimethyl-6,7-dihydro-1H-indol-4(5H)-one | 337 |
| 140 | 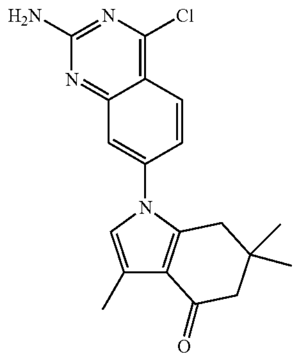 | 1-(2-amino-4-chloroquinazolin-7-yl)-3,6,6-trimethyl-6,7-dihydro-1H-indol-4(5H)-one | 355 |

-continued
| Compound No. | Structure | Name | [M + H]+ |
|---|---|---|---|
| 141 | 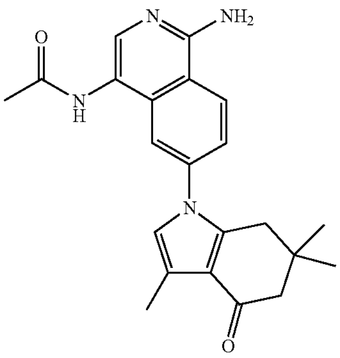 | N-(1-amino-6-(3,6,6-trimethyl-4-oxo-4,5,6,7-tetrahydro-1H-indol-1-yl)isoquinolin-4-yl)acetamide | 377 |
| 142 | 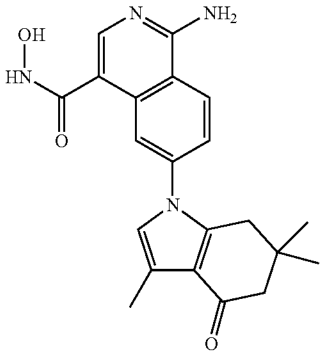 | 1-amino-N-hydroxy-6-(3,6,6-trimethyl-4-oxo-4,5,6,7-tetrahydro-1H-indol-1-yl)isoquinoline-4-carboxamide | 379 |
| 143 | 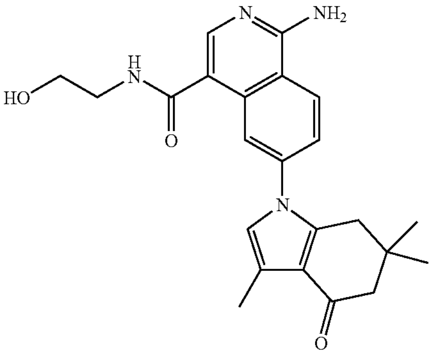 | 1-amino-N-(2-hydroxyethyl)-6-(3,6,6-trimethyl-4-oxo-4,5,6,7-tetrahydro-1H-indol-1-yl)isoquinoline-4-carboxamide | 407 |
| 144 | 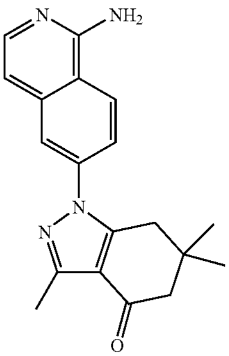 | 1-(1-Amino-isoquinolin-6-yl)-3,6,6-trimethyl-1,5,6,7-tetrahydro-indazol-4-one | 321 |

-continued
| Compound No. | Structure | Name | [M + H]$^+$ |
|---|---|---|---|
| 145 | 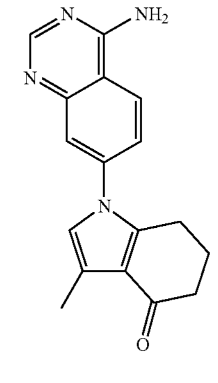 | 1-(4-Amino-quinazolin-7-yl)-3-methyl-1,5,6,7-tetrahydro-indol-4-one | 293 |
| 146 | 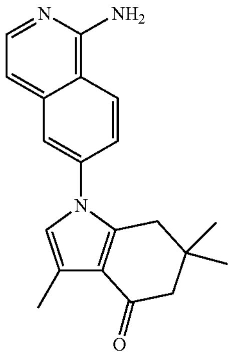 | 1-(1-Amino-isoquinolin-6-yl)-3,6,6-trimethyl-1,5,6,7-tetrahydro-indol-4-one | 320 |
| 147 | 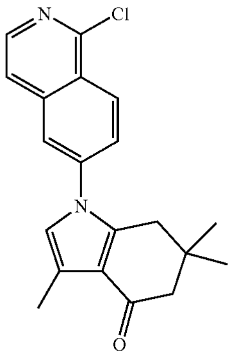 | 2-(2-methoxyethylamino)-4-(3-methyl-4-oxo-4,5,6,7-tetrahydroindol-1-yl)benzamide | 339 |
| 148 | 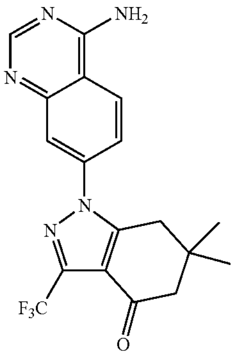 | 1-(4-Amino-quinazolin-7-yl)-6,6-dimethyl-3-trifluoromethyl-1,5,6,7-tetrahydro-indazol-4-one | 376 |

-continued
| Compound No. | Structure | Name | [M + H]+ |
| --- | --- | --- | --- |
| 149 | 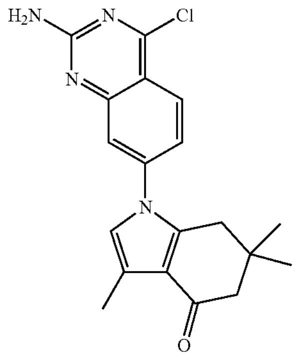 | 1-(2-amino-4-chloroquinazolin-7-yl)-3,6,6-trimethyl-6,7-dihydro-1H-indol-4(5H)-one | 355 |
| 150 | 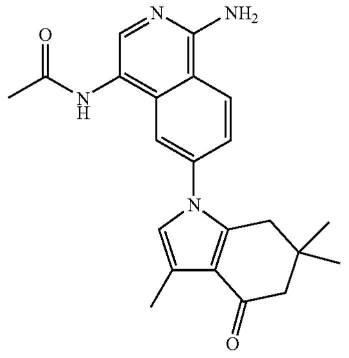 | N-(1-amino-6-(3,6,6-trimethyl-4-oxo-4,5,6,7-tetrahydro-1H-indol-1-yl)isoquinolin-4-yl)acetamide | 377 |
| 151 | 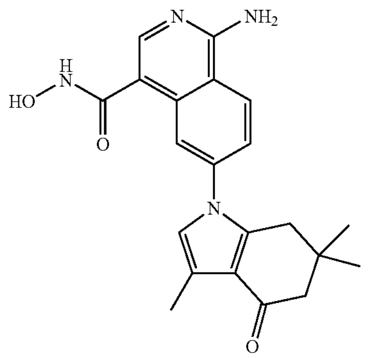 | 1-amino-N-hydroxy-6-(3,6,6-trimethyl-4-oxo-4,5,6,7-tetrahydro-1H-indol-1-yl)isoquinoline-4-carboxamide | 379 |
| 152 | 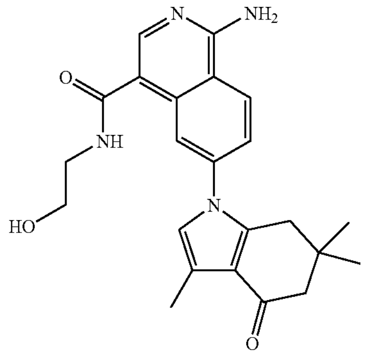 | 1-amino-N-(2-hydroxyethyl)-6-(3,6,6-trimethyl-4-oxo-4,5,6,7-tetrahydro-1H-indol-1-yl)isoquinoline-4-carboxamide | 407 |

Biological Evaluation

Example 39

Cell Proliferation Assays

A panel of cancer cell lines is obtained from the DCTP Tumor Repository, National Cancer Institute (Frederick, Md.) or ATCC (Rockville, Md.). Cell cultures are maintained in Hyclone RPMI 1640 medium (Logan, Utah) supplemented with 10% fetal bovine serum and 20 mM HEPES buffer, final pH 7.2, at 37° C. with a 5% $CO_2$ atmosphere. Cultures are maintained at sub-confluent densities. Human umbilical vein endothelial cells (HUVEC) are purchased from Clonetics, a division of Cambrex (Walkersville, Md.). Cultures are established from cryopreserved stocks using Clonetics EGM-2 medium supplemented with 20 mM HEPES, final pH 7.2, at 37° C. with a 5% $CO_2$ atmosphere.

For proliferation assays, cells are seeded with the appropriate medium into 96 well plates at 1,000-2,500 cells per well, depending on the cell line, and are incubated overnight. The following day, test compound, DMSO solution (negative control), or Actinomycin D (positive control) is added to the appropriate wells as 10× concentrated stocks prepared in phosphate buffered saline. The cell plates are then incubated for an additional 2-5 days, depending on the cell line, to allow proliferation to occur. To measure cell density, 50 μL of WST-1 solution (Roche Applied Science, IN) diluted 1:5 in phosphate buffered saline is added to each well, and the cells incubated for an additional 1-5 hrs., again depending on the cell line. Optical density is determined for each well at 450 nM using a Tecan GeniosPro plate reader (RTP, NC). The percentage of cell growth is determined by comparing the cell growth in the presence of test compounds to the cells treated with DMSO vehicle (control, 100% growth) and cells treated with Actinomycin D (10 μM, 0% growth).

Immediately after the WST-1 determination, the medium is removed from the PC-3, NCI-H460 and HUVEC cell lines, and the plates stored at −80° C. Using these assay plates, relative amounts of DNA in each well are determined using the Cyquant DNA assay kit from R&D Systems (Eugene, Oreg.) following the manufacturer's directions. Results for each compound treatment are compared to DMSO vehicle control (100%) and 10 μM Actinomycin D treated cells (0%).

Several exemplary compounds useful in the methods of the invention are listed below. The range of their inhibitory activity against PC-3 cell proliferation is demonstrated, where +++ stands for an $IC_{50}$ value that is less than 0.5 μM, ++between 0.5 and 5 μM, +between 5 and 50 μM.

| Example No. | $IC_{50}$ value | Example No. | $IC_{50}$ value |
|---|---|---|---|
| 38 | + | 39 | ++ |
| 43 | ++ | 47 | + |
| 51 | + | 52 | + |
| 54 | ++ | 62 | ++ |
| 65 | ++ | 66 | ++ |
| 73 | + | 78 | ++ |
| 81 | +++ | 83 | + |
| 90 | +++ | 92 | +++ |
| 94 | ++ | 102 | + |
| 104 | + | 107 | ++ |
| 110 | ++ | 121 | + |
| 126 | ++ | 128 | +++ |
| 133 | ++ | 139 | +++ |

Example 40

Determination of Affinity for HSP-90

(Heat Shock Protein 90)

Affinity of test compounds for HSP-90 is determined as follows: Protein mixtures obtained from a variety of organ tissues (for example: spleen, liver and lung) are reversibly bound to a purine affinity column to capture purine-binding proteins, especially HSP-90. The purine affinity column is washed several times, and then eluted with 20 μM, 100 μM, and 500 μM of test compound. Compounds of Formula I elute HP-90 in a dose-dependent manner vs. a control elution using dimethylsulfoxide. The elution profile of Formula I compounds is determined by 1-dimensional SDS polyacrylamide gel electrophoresis. Gels are stained with a fluorescent stain such as sypro ruby (a highly sensitive fluorescent protein stain that can readily detect less than 1 fmol of total protein, i.e., less than 0.04 ng for a 40 kDa protein) or silver nitrate. The gels are imaged using a standard flat bed gel imager and the amount of protein estimated by densitometry. The percent of HSP-90 protein eluted from the column at each concentration is determined and $IC_{50}$ values are calculated from these estimates.

Compounds of the invention are inhibitors of HSP-90 (heat shock protein 90) and have $IC_{50}$ values in the range of 0.02 μM to 20 μM. Several exemplary compounds useful in the methods of the invention are listed below. Their relative binding affinity to HSP-90 is listed, where +++ stands for very high, ++ for high and + for moderate.

| Example No. | Affinity | Example No. | Affinity |
|---|---|---|---|
| 40 | +++ | 41 | +++ |
| 44 | + | 45 | ++ |
| 46 | + | 53 | +++ |
| 56 | +++ | 60 | +++ |
| 63 | + | 68 | +++ |
| 71 | + | 76 | ++ |
| 72 | ++ | 80 | ++ |
| 77 | ++ | 88 | + |
| 87 | +++ | 95 | +++ |
| 93 | +++ | 99 | ++ |
| 98 | ++ | 106 | ++ |
| 105 | +++ | | |

The invention and the manner and process of making and using it, are now described in such full, clear, concise and exact terms as to enable any person skilled in the art to which pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A compound according to the formula I,

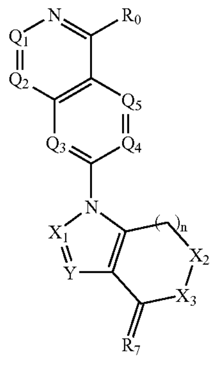

I or pharmaceutically acceptable salts thereof, wherein $R_0$ is hydrogen, halogen, cyano, nitro, or —A—$R_{0'}$, wherein A is a bond, —O—, —S—, —N($R_{0'}$)—, —N($R_{0'}$)CO—, —N[C(O)$R_{0'}$]C(O)—, —N($R_{0'}$)$SO_2$—, —$SO_2$N($R_{0'}$)—, —$SO_2$—, —CO—, —$CO_2$—, or —C(O)N($R_{0'}$)—; and each $R_{0'}$ is independently hydrogen, $C_1$-$C_{10}$ haloalkyl, $C_1$-$C_{10}$ alkyl, $C_3$-$C_{10}$cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, halo($C_1$-$C_6$)alkyl, or carboxamide;

$Q_1$, $Q_4$, and $Q_5$ are each $CR_1$, wherein each $R_1$ is hydrogen, halogen, cyano, nitro, or —B—$R_{1'}$, wherein B is a bond, —O—, —S—, —N($R_{1'}$)—, —N($R_{1'}$)CO—, —N[C(O)$R_{1'}$]—C(O)—, —N($R_{1'}$)$SO_2$, —$SO_2$N($R_{1'}$)—, —$SO_2$—, —CO—, —$CO_2$—, or —C(O)N($R_{1'}$)—; and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$—$C_6$ alkoxy, halogen, hydroxy, carboxy, oxo, amino, mono- or di-($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di—($C_1$-$C_6$) alkylamino, halo($C_1$-$C_6$)alkyl, or carboxamide;

$Q_2$ is N, $Q_3$ is $CR_2$, wherein each $R_2$ is independently (a)H, (b) halogen, or (c) a $C_1$-$C_{15}$ alkyl group where up to five of the carbon atoms in said alkyl group are optionally replaced independently by $R_{22}$, carbonyl, ethenyl, ethynyl or a moiety selected from N, O, S $SO_2$ or SO, with the proviso that two O atoms, two S atoms, or an O and S atom are not immediately adjacent each other, wherein $R_{22}$ is (i) heteroaryl, (ii) aryl, (iii) saturated or unsaturated $C_3$-$C_{10}$ cycloalkyl, or (iv) saturated or unsaturated $C_2$-$C_{10}$ heterocycloalkyl, wherein each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$)alkyl, —$SO_2$—($C_1$-$C_6$)alkyl, —$SO_2$—aryl, —SO—($C_1$-$C_6$)alkyl, —SO—aryl, —$SO_2NH_2$, —$SO_2$NH—($C_1$-$C_6$)alkyl, —$SO_2$NH—aryl, ($C_1$-$C_6$)alkoxy, or mono- or di—($C_1$-$C_{10}$)alkylamino; and each $R_{22}$ is optionally fused to a $C_6$-$C_{10}$ aryl group, $C_5$—$C_8$ saturated cyclic group, or a $C_5$—$C_{10}$ heterocycloalkyl group;

wherein each (c) is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH—aryl, —$SO_2$—aryl, —SO—($C_1$-$C_6$)alkyl, —$SO_2$—aryl, $C_1$-$C_6$ alkoxy, $C_2$-$C_{10}$ alkenyloxy, $C_2$-$C_{10}$ alkynyloxy, mono-or di—($C_1$-$C_{10}$)alkylamino, or $R_{23}$, wherein $R_{23}$ is (1) heteroaryl, (2) aryl, (3) saturated or unsaturated $C_5$-$C_{10}$ cycloalkyl, or (4) saturated or unsaturated $C_5$-$C_{10}$heterocycloalkyl, and the $R_{23}$ groups are optionally substituted at least one group which is independently hydroxy, oxo, halo, amino, cyano, nitro, —SH, —S—($C_1$-$C_6$)alkyl, —$SO_2$—($C_1$-$C_6$)alkyl, —$SO_2$—aryl, —SO—($C_1$-$C_6$)alkyl, —SO—aryl, —$SO_2NH_2$, —$SO_2$NH—($C_1$-$C_6$)alkyl, —$SO_2$NH—aryl, ($C_1$-$C_6$)alkoxy, or mono- or di—($C_1$-$C_{10}$)alkylamino;

$R_7$ is O—;

$X_1$ is N or $CR_c$, Y is $CR_c$, wherein each $R_c$ independently is hydrogen, halogen, cyano, nitro, $C_1$-$C_{10}$ alkyl,$C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl ($C_1$-$C_{10}$)alkyl, heterocycloalkyl, aryl, or heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, amino, mono- or di—($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl, wherein the aryl and heteroaryl groups are optionally substituted with from 1-4 groups that are independently $C_1$-$C_6$ alkyl, $C_1$-$C_6$ alkoxy, halogen, hydroxy, amino, mono- or di—($C_1$-$C_6$) alkylamino, halo($C_1$-$C_6$)alkyl, or carboxamide $X_2$ and $X_3$ are independently $C(R_5)(R_6)$, wherein each $R_5$ and $R_6$ is independently hydrogen, $C_1$-$C_6$ alkyl, or mono- or di—($C_1$-$C_6$)alkylamino($C_1$-$C_6$)alkykl;

n is 1.

2. The compound according to claim 1, wherein $R_0$ is hydrogen, halogen, $C_1$-$C_3$ alkyl, or —A—$R_{0'}$, wherein A is —O—, —N($R_{0'}$)—, —N($R_{0'}$)CO—, —N[C (O)$R_{0'}$] C(O)—, or—N($R_{0'}$)$_{SO2}$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl.

3. The compound according to claim 2, wherein $R_0$ is —N($R_{0'}$)$_2$—, wherein each $R_0$ is independently hydrogen, $C_1$-$C_{10}$ haloalkyl, $C_1$-$C_{10}$ alkyl, or $C_3$—$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl.

4. The compound according to claim 3, wherein $R_0$ is —N($R_{0'}$)$_2$—, wherein each $R_{0'}$ is independently hydrogen, $C_1$-$C_{10}$ haloalkyl, $C_1$-$C_{10}$ alkyl.

5. The compound according to claim 1, wherein $R_1$ is hydrogen, or —B—$R_1$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl.

6. The compound according to claim 1, wherein $X_1$ is N.

7. The compound according to claim 1, wherein $X_1$ is $CR_c$.

8. The compound according to claim 1, wherein $X_1$ is N, Y is $CR_c$, $R_c$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl.

9. The compound according to claim 1, wherein $X_1$ is $CR_c$, Y is $CR_c$, wherein each $R_c$ is independently hydrogen, halogen, $C_1$-$C_{10}$ alkyl, $C_1$-$C_{10}$ haloalkyl, $C_3$-$C_7$ cycloalkyl, or $_3$-$C_7$ cycloalkyl ($C_1$-$C_{10}$)alkyl.

10. The compound according to claim 1, of the formula IA

IA

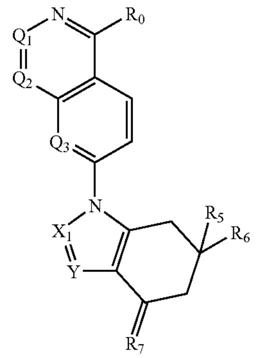

wherein $R_0$ is hydrogen, halogen, $C_1$-$C_3$ alkyl, or —A—$R_{0'}$, wherein

A is —0—, —N($R_{0'}$)—, —N($R_{0'}$)CO—, —N[C(O)$R_{0'}$]C (O)—, or—N($R_{0'}$)$SO_2$—; and each $R_0$ is independently hydrogen, $C_1$-$C_{10}$ haloalkyl, $C_1$-$C_0$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$—$C_6$) alkylamino, cyano, nitro, halo($C_1$-$C_6$)alkyl, halo($C_1$-$C_6$)alkoxy, carboxamide, heterocycloalkyl, aryl, or heteroaryl.

11. The compound according to claim 10, wherein $R_0$ is —N($R_{0'}$)$_2$—, wherein each $R_0$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl.

12. The compound according to claim 10, wherein $Q_1$ is $CR_1$, wherein $R_1$ is hydrogen, or —B—$R_{1'}$, wherein B is a bond, —O—, or —N($R_{1'}$)—, and each $R_1$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1C_6$ alkoxy, halogen, hydroxy, carboxy, oxo, amino, mono- or di—($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl.

13. The compound according to claim 10, wherein $Q_3$ is $CR_2$ wherein each $R_2$ is independently (a)H, (b) halogen, or (c) a $C_1$-$C_{15}$ alkyl group wherein each (c) is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$-($C_1$-$C_6$)alkyl, —$SO_2NH_2$, —$SO_2NH$—($C_1$-$C_6$)alkyl, —$SO_2NH$—aryl, —$SO_2$—aryl, —SO—($C_1C_6$)alkyl, —$SO_2$—aryl, $C_1$-$C_{10}$ alkoxy, $C_2C_{10}$ alkenyloxy, $C_2C_{10}$ alkynyloxy, mono($C_1$-$C_{10}$)alkylamino, or di($C_1$-$C_{10}$) alkylamino.

14. The compound according to claim 10, wherein $X_1$ is N.

15. The compound according to claim 10, wherein $X_1$ is $CR_c$.

16. The compound according to claim 14, wherein Y is $CR_c$, wherein $R_c$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl ($C_1C_{10}$)alkyl.

17. The compound according to claim 15, wherein Y is $CR_c$, wherein each $R_c$ is independently hydrogen, halogen, $C_1C_{10}$ alkyl, $C_1C_{10}$haloalkyl, $C_3$-$C_7$ cycloalkyl, or $C_3$-$C_7$ cycloalkyl($C_1C_{10}$)alkyl.

18. The compound according to claim 1, of the formula IB

IB

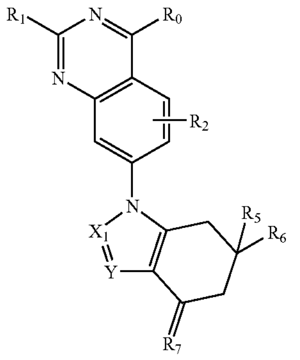

wherein $R_0$ is hydrogen, halogen, $C_1$-$C_3$ alkyl, or A—$R_{0'}$, wherein

A is —O—, —N($R_{0'}$)—, —N($R_{0'}$)CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl.

19. The compound according to claim 18, wherein $R_0$ is —N($R_{0'}$)$_2$—, and each $R_{0'}$ is independently hydrogen, $C_1$-$C_{10}$ haloalkyl, $C_1$-$C_{10}$ alkyl, or $C_3$—$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl.

20. The compound according to claim 18, wherein $R_1$ is hydrogen, or —B—$R_{1'}$, wherein B is a bond, —O—, or —N($R_{1'}$)—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di-($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl.

21. The compound according to claim 18, wherein $X_1$ is N.

22. The compound according to claim 18, wherein $X_1$ is $CR_c$.

23. The compound according to claim 18, wherein Y is $CR_c$, wherein each $R_c$ is independently hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl.

24. The compound according to claim 1, of the formula IC

IC

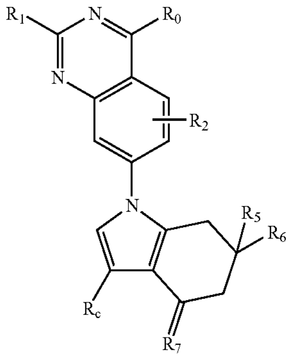

wherein $R_0$ is hydrogen, halogen, $C_1$-$C_3$ alkyl, or —A—$R_{0'}$, wherein

A is —O—, —N($R_{0'}$)—, —N($R_{0'}$)CO—, —N[C(O)$R_{0'}$]C(O)—, or—N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$cycloalkyl, $C_2$-$C_{10}$heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl.

25. The compound according to claim 24, wherein $R_0$ is —$N(R_{0'})_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$alkoxy, halogen, hydroxy, carboxy, oxo, amino, mono- or di—($C_1$-$C_8$) alkylamino, cyano, nitro, halo($C_1$-$C_6$)alkyl, halo($C_1$-$C_6$ )alkoxy, carboxamide, heterocycloalkyl, aryl, or heteroaryl.

26. The compound according to claim 24, wherein $R_1$ is hydrogen, or —B—$R_{1'}$, wherein B is a bond, —O—, or —$N(R_{1'})$—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_1$-$C_6$ alkoxy, halogen, hydroxy, carboxy, oxo, amino, mono- or di—($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl.

27. The compound according to claim 24, wherein $R_c$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl.

28. The compound according to claim 1, of the formula ID

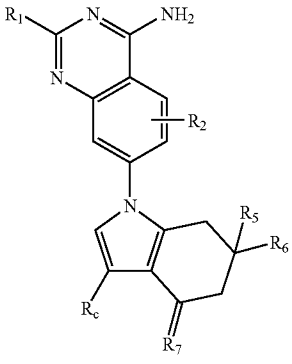

ID wherein $R_1$ is hydrogen, or —B—$R_{1'}$, wherein

B is a bond, —O—, or —$N(R_{1'})$—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_1$-$C_6$alkoxy, halogen, hydroxy, carboxy, oxo, amino, mono- or di—($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl.

29. The compound according to claim 28, wherein $R_c$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl.

30. The compound according to claim 1, of the formula IE

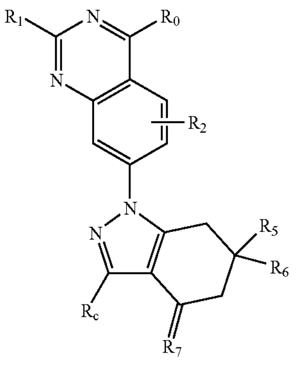

IE wherein $R_0$ is hydrogen, halogen, $C_1$-$C_3$ alkyl, or —A—$R_{0'}$, wherein A is —O—, —$N(R_{0'})$—, —$N(R_{0'})CO$—, —$N[0(O)R_{0'}]$ $C(O)$—, or —$N(R_{0'})SO_2$-; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_0$-$C_6$ alkoxy, halogen, hydroxy, carboxy, oxo, amino, mono- or di—($C_1C_6$) alkylamino, cyano, nitro, halo($C_1$-$C_6$)alkyl, halo($C_1$-$C_6$) alkoxy, carboxamide, heterocycloalkyl, aryl, or heteroaryl.

31. The compound according to claim 30, wherein $R_0$ is —$N(R_{0'})_2$—, and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl.

32. The compound according to claim 30, wherein $R_{1'}$ is hydrogen, or —B—$R_{1'}$, wherein B is a bond, —O—, or —$N(R_{1'})$—, and each $R_{1'}$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo($C_1$-$C_6$)alkyl, halo($C_1$-$C_6$) alkoxy, carboxamide, heterocycloalkyl, aryl, or heteroaryl.

33. The compound according to claim 30, wherein $R_c$ is hydrogen, halogen, $C_1$-$C_{10}$ alkyl, $C_1$-$C_{10}$ haloalkyl, $C_3$-$C_7$ cycloalkyl, or $C_3$-$C_7$cycloalkyl($C_1$-$C_{10}$)alkyl.

34. The compound according to claim 1, of the formula IF

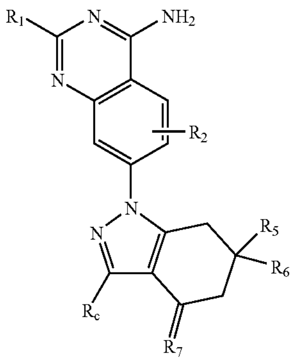

IF wherein $R_1$ is hydrogen, or —B—$R_{1'}$, wherein

B is a bond, —O—, or —N($R_{1'}$)—, and each $R_1$ is independently hydrogen, $C_1$-$C_{10}$ haloalkyl, $C_1$-$C_{10}$ alkyl, $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl.

35. The compound according to claim 34, wherein $R_c$ is hydrogen, halogen, $C_1$-$C_{10}$ alkyl, $C_1$-$C_{10}$ haloalkyl, $C_3$-$C_7$ cycloalkyl, or $C_3$-$C_7$ cycloalkyl($C_1$-$C_{10}$)alkyl.

36. The compound according to claim 1, of the formula IG

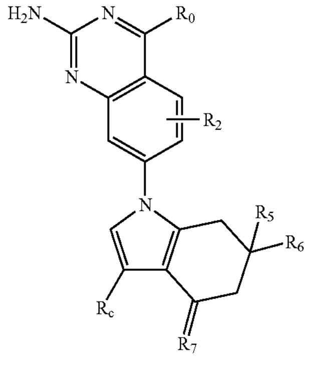

IG wherein $R_0$ is hydrogen, halogen, $C_1$-$C_3$ alkyl, or —A—$R_{0'}$, wherein A is —N($R_{0'}$)—, —N($R_{0'}$)CO—, —N[C(O)$R_{0'}$]C(O)—, or —N($R_{0'}$)$SO_2$-; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, carboxy, oxo, amino, mono- or di—($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl.

37. The compound according to claim 36, wherein $R_0$ is hydroxyl.

38. The compound according to claim 36, wherein $R_0$ is —N($R_{0'}$)$_2$—, and each $R_{0'}$ is independently hydrogen, $C_1$-$C_{10}$ haloalkyl, or $C_1$-$C_{10}$ alkyl.

39. The compound according to claim 38, wherein $R_0$ is —$NH_2$.

40. The compound according to claim 1, of the formula IH

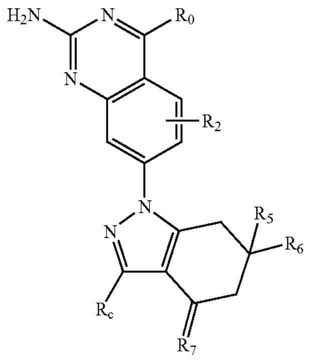

IH wherein $R_0$ is hydrogen, halogen, hydroxyl, $C_1$-$C_3$ alkyl or —A—$R_{0'}$, wherein A is —N($R_{0'}$)—, —N($R_{0'}$CO—, —N[C(O)$R_{0'}$]C(O)—, or —N($R_{0'}$)$SO_2$—; and each $R_{0'}$ is independently hydrogen, $C_1$-$C_{10}$ haloalkyl, $C_1$-$C_{10}$ alkyl, or $C_3$-$C_{10}$ cycloalkyl, $C_2$-$C_{10}$ heterocycloalkyl, aryl, heteroaryl, wherein each alkyl, aryl, cycloalkyl, heterocycloalkyl, and heteroaryl group is optionally substituted with from 1-4 groups that are independently $C_1$-$C_{10}$ alkyl, $C_3$-$C_{10}$ alkoxy, halogen, hydroxy, carboxy, oxo, amino, mono- or di—($C_1$-$C_6$) alkylamino, cyano, nitro, halo ($C_1$-$C_6$)alkyl, halo($C_1$-$C_6$)alkoxy, carboxamide, heterocycloalkyl, aryl, or heteroaryl.

41. The compound according to claim 40, wherein $R_0$ is hydroxyl.

42. The compound according to claim 40, wherein $R_0$ is —N($R_{0'}$)$_2$—, and each $R_{0'}$ is independently hydrogen, $C_1$-$C_{10}$ haloalkyl, or $C_1$-$C_{10}$ alkyl.

43. The compound according to claim 42, wherein $R_0$ is —$NH_2$.

44. The compound according to claim 1, selected from the group consisting of 1-(4-Amino-quinazolin-7-yl)-3,6,6-trimethyl-1,5,6,7-tetrahydro-indol-4-one;

1-(4-Amino-2-methyl-quinazolin-7-yl)-3,6,6-trimethyl-1 ,5,6,7-tetrahydro-indol-4-one;

1-(2,4-Diamino-q uinazolin-7-yl)-3,6,6-trimethyl-1,5,6,7-tetrahydro-indol-4-one;

1-(4-Amino-8-fluoro-quinazolin-7-yI)-3,6,6-trimethyl-1, 5,6,7-tetrahydro-indol-4-one;

1-[4-Amino-8-(2-methoxy-ethoxy)-quinazol in-7-yI]-3,6, 6-trim ethyl-1,5,6,7-tetrahyd ro-indol-4-one;

1-[4-Amino-8-(2-dimethylamino-ethoxy)-quinazolin-7-yI]-3,6,6-trimethyl-1,5,6,7-tetrahydro-indol-4-one;

1-(4-Amino-quinazolin-7-yl)-3-methyl-1,5,6,7-tetrahydro-indol-4-one;

1-(4-Amino-quinazolin-7-yl)-6,6-dimethyl-3-trifluoromethyl-1,5,6,7-tetrahydro-indazol-4-one;

1-[4-Amino-8-(2-methoxy-ethylamino)-quinazolin-7-yl]-3,6,6-trimethyl-1,5,6,7-tetrahydro-indol-4- one;

1-(4-Amino-5-fluoro-quinazolin-7-yl)-3,6,6-trimethyl-1,5,6,7-tetrahydro-indol-4-one;

1-(4-Amino-5-butylsulfanyl-quinazolin-7-yl)-3,6,6-trimethyl-1,5,6,7-tetrahydro-indol-4-one 1-(4-Amino-quinazolin-7-yl)-3-cyclopropylmethyl-3,6,6-dimethyl- 1,5,6,7-tetrahydro-indazol-4-one;

1-(4-Cyclopropylamino-quinazolin-7-yl)-3,6,6-trimethyl-1,5,6,7-tetrahydro-indol-4-one;

1-(2-Amino-quinazolin-7-yl)-3,6,6-trimethyl-1,5,6,7-tetrahydro-indol-4-one; and 1-(2-Amino-4-methyl-quinazolin-7-yl)-3,6,6-trimethyl-1,5,6,7-tetrahydro-indol-4-one;

or pharmaceutically acceptable salts thereof.

45. The compound according to claim 1, selected from the group consisting of 1-(4-aminoquinazolin-7-yl)-3,6,6-trimethyl-6,7-dihydro-1H-indol-4(5H)-one;

1-(4-amino-2-methylquinazolin-7-yl)-3,6,6-trimethyl-6,7-dihydro-1H-indol-4(5H)-one;

1-(2,4-diaminoq uinazolin-7-yl)-3,6,6-trimethyl-6,7-dihydro-1H-indol-4(5H)-one;

1-(4-amino-8-fluoroquinazolin-7-yl)-3,6,6-trimethyl-6,7-dihydro-1H-indol-4(5H)-one;

1-(4-aminoquinazolin-7-yl)-3-methyl-6,7-dihydro-1H-indol-4(5H)-one;

1-(4-amino-8-(2-methoxyethoxy)q u inazol in-7-yl)-3,6,6-trimethyl-6, 7-dihydro-1H-indol-4(5H)-one;

1-(4-aminoquinazolin-7-yl)-6,6-dimethyl-3-(trifluoromethyl)-6,7-dihydro-1H-indazol-4(5H)-one;

1-(4-amino-8-(2-(dimethylamino)ethoxy)quinazolin-7-yl)-3,6,6-trimethyl-6,7-dihydro-1H-indol-4(5H)-one;

1-(4-amino-8-butoxyquinazolin-7-yl)-3,6,6-trimethyl-6,7-dihydro-1H-indol-4(5H)-one;

1-(4-amino-8-(butylthio)quinazolin-7-yl)-3,6,6-trimethyl-6,7-dihydro-1H-indol-4(5H)-one;

1-(4-amino-8-(butylamino)quinazolin-7-yl)-3,6,6-trimethyl-6,7-dihydro-1H-indol-4(5H)-one;

1-(4-amino-8-(2-methoxyethylamino)quinazolin-7-yl)-3,6,6-trimethyl-6,7-dihydro-1H-indol-4(5H)-one;

1-(4-amino-8-(2-hydroxyethoxy)quinazolin-7-yl)-3,6,6-trimethyl-6,7-dihydro-1H-indol-4(5H)-one;

1-(4-amino-8-(3-hydroxypropoxy)quinazolin-7-yl)-3,6,6-trimethyl-6,7-dihydro-1H-indol-4(5H)-one;

1-(4-amino-8-(2-(dimethylamino)ethylamino)quinazolin-7-yl)-3,6,6-trimethyl-6,7-dihydro-1H-indol-4(5H)-one;

1-(4-amino-8-(3-methoxypropoxy)quinazolin-7-yl)-3,6,6-trimethyl-6,7-dihydro-1H-indol-4(5H)-one;

1-(4-amino-8-methoxyquinazolin-7-yl)-3,6,6-trimethyl-6,7-dihydro-1H-indol-4(5H)-one;

1-(4-amino-8-ethoxyquinazolin-7-yl)-3,6,6-trimethyl-6,7-dihydro-1H-indol-4(5H)-one;

1-(4-amino-5-fluoroquinazolin-7-yl)-3,6,6-trimethyl-6,7-dihydro-1H-indol-4(5H)-one; 1-(4-amino-8-mercaptoquinazolin-7-yl)-3,6,6-trimethyl-6,7-dihydro-1H-indol-4(5H)-one;

1-(4-amino-8-fluoroquinazolin-7-yl)-3,6-dimethyl-6,7-dihydro-1H-indol-4(5H)-one;

1-(8-(allylthio)-4-aminoquinazolin-7-yl)-3,6,6-trimethyl-6,7-dihydro-1H-indol-4(5H)-one; 1-(4-amino-8-hydroxyquinazolin-7-yl)-3,6,6-trimethyl-6,7-dihydro-1H-indol-4(5H)-one;

1-(4-amino-8-(prop-2-ynyloxy)quinazolin-7-yl)-3,6,6-trimethyl-6,7-dihydro-1H-indol-4(5H)-one;

1-(4-amino-8-(but-3-ynyloxy)quinazolin-7-yl)-3,6,6-trimethyl-6,7-dihydro-1H-indol-4(5H)-one;

1-(4-amino-5-(prop-2-ynyloxy)quinazolin-7-yl)-3,6,6-trimethyl-6,7-dihydro-1H-indol-4(5H)-one;

1-(4-amino-8-(butylthio)quinazolin-7-yl)-3,6-dimethyl-6,7-dihydro-1H-indol-4(5H)-one;

1-(4-amino-5-(butylthio)quinazolin-7-yl)-3,6,6-trimethyl-6,7-dihydro-1H-indol-4(5H)-one;

1-(4-amino-8-(2-aminoethylthio)quinazolin-7-yl)-3,6,6-trimethyl-6,7-dihydro-1H-indol-4(5H)-one;

1-(4-amino-8-(2-(dimethylamino)ethylthio)quinazolin-7-yl)-3,6,6-trimethyl-6,7-dihydro-1H-indol-4(5H)-one;

1-(4-amino-5-methoxyquinazolin-7-yl)-3,6,6-trimethyl-6,7-dihydro-1H-indol-4(5H)-one;

tert-butyl 2-(4-amino-7-(3,6,6-trimethyl-4-oxo-4,5,6,7-tetrahydro-1H-indol-1-yl)quinazolin-8-ylthio)ethylcarbamate;

1-(4-amino-5-(3,5-dimethoxybenzyloxy)quinazolin-7-yl)-3,6,6-trimethyl-6,7-dihydro-1H-indol-4(5H)-one;

1-(4-amino-5-hydroxyquinazolin-7-yl)-3,6,6-trimethyl-6,7-dihydro-1H-indol-4(5H)-one;

1-(4-amino-8-chloroquinazolin-7-yl)-3,6,6-trimethyl-6,7-dihydro-1H-indol-4(5H)-one;

1-(4-amino-8-(2-(neopentylamino)ethylthio)quinazolin-7-yl)-3,6,6-trimethyl-6,7-dihydro-1H-indol-4(5H)-one;

1-(4-aminoquinazolin-7-yl)-3-ethyl-6,6-dimethyl-6,7-dihydro-1H-indazol-4(5H)-one;

1-(4-aminoquinazolin-7-yl)-3-(cyclopropylmethyl)-6,6-dimethyl-6,7-dihydro-1H-indazol-4(5H)-one;

1-(4-amino-5-fluoroquinazolin-7-yl)-3-ethyl-6,6-dimethyl-6,7-dihydro-1H-indazol-4(5H)-one;

1-(4-aminoquinazolin-7-yl)-3,6,6-trimethyl-6,7-dihydro-1H-indazol-4(5H)-one;

1-(4-aminoquinazolin-7-yl)-3-isobutyl-6,6-dimethyl-6,7-dihydro-1H-indazol-4(5H)-one;

1-(4-aminoquinazolin-7-yl)-3-methyl-6,7-dihydro-1H-indazol-4(5H)-one;

1-(4-(cyclopropylamino)quinazolin-7-yl)-3,6,6-trimethyl-6,7-dihydro-1H-indol-4(5H)-one;

1-(4-hydroxyquinazolin-7-yl)-3,6,6-trimethyl-6,7-dihydro-1H-indol-4(5H)-one;

1-(4-aminoquinazolin-7-yl)-2,6,6-trimethyl-6,7-dihydro-1H-indol-4(5H)-one;

1-(4-aminoquinazolin-7-yl)-2,3,6,6-tetramethyl-6,7-dihydro-1H-indol-4(5H)-one;

1-(4-amino-8-(2-hydroxyethylthio)quinazolin-7-yl)-3,6,6-trimethyl-6,7-dihydro-1H-indol-4(5H)-one;

1-(4-amino-8-fluoroquinazolin-7-yl)-3,6,6-trimethyl-6,7-dihydro-1H-indazol-4(5H)-one;

2-(4-amino-7-(3,6,6-trimethyl-4-oxo-4,5,6,7-tetrahydro-1H-indol-1-yl)quinazolin-8- ylthio)acetaldehyde;

1-(4-amino-8-(butylthio)quinazolin-7-yl)-3,6,6-trimethyl-6,7-dihydro-1H-indazol-4(5H)-one;

1-(2-aminoquinazolin-7-yl)-3,6,6-trimethyl-6,7-dihydro-1H-indol-4(5H)-one;

1-(4-amino-8-(2-(isobutylamino)ethylthio)quinazolin-7-yl)-3,6,6-trimethyl-6,7-dihydro-1H-indol-4(5H)-one;

1-(4-amino-8-(2-(tert-butylamino)ethylthio)quinazolin-7-yl)-3,6,6-trimethyl-6,7-dihydro-1H-indol-4(5H)-one;

1-(4-amino-8-(2-(isopropylamino)ethylthio)quinazolin-7-yI)-3,6,6-trimethyl-6,7-dihydro-1H-indol-4(5H)-one; 1-(4-amino-8-(2-(cyclopropylamino)ethylthio)quinazolin-7-yI)-3,6,6-trimethyl-6,7-dihydro-1H-indol-4(5H)-one;

1-(4-amino-8-(2-(cyclopropylmethylamino)ethylthio)quinazolin-7-yI)-3,6,6-trimethyl-6,7-dihydro-1H-indol-4(5H)-one;

1-(4-amino-8-(2-(methylamino)ethylthio)quinazolin-7-yI)-3,6,6-trimethyl-6,7-dihydro-1 H-indol-4(5H)-one;

1-(4-amino-8-(2-(ethylamino)ethylthio)quinazolin-7-yI)-3,6,6-trimethyl-6,7-dihydro-1 H-indol-4(5H)-one;

1-(4-amino-8-(pyridin-2-ylmethylthio)quinazolin-7-yI)-3,6,6-trimethyl-6,7-dihydro-1H-indazol-4(5H)-one;

1-(4-amino-8-(phenylthio)quinazolin-7-yl)-3,6,6-trimethyl-6,7-dihydro-1H-indol-4(5H)-one;

1-(4-amino-8-(ethylthio)quinazolin-7-yI)-3,6,6-trimethyl-6,7-dihydro-1H-indol-4(5H)-one;

1-(4-amino-8-(methylthio)quinazolin-7-yI)-3,6,6-trimethyl-6,7-dihydro-1H-indol-4(5H)-one;

1-(4-amino-8-(ethylsulfinyl)quinazolin-7-yI)-3,6,6-trimethyl-6,7-dihydro-1H-indol-4(5H)-one;

1-(2,4-diamino-5-fluoroquinazolin-7-yI)-3,6,6-trimethyl-6,7-dihydro-1H-indol-4(5H)-one;

1-(2,4-diamino-5-(ethylthio)quinazolin-7-yI)-3,6,6-trimethyl-6,7-dihydro-1H-indol-4(5H)-one;

1-(2-amino-4-methylquinazolin-7-yl)-3,6,6-trimethyl-6,7-dihydro-1H-indol-4(5H)-one;

1-(2-amino-4-methylquinazolin-7-yI)-3,6,6-trimethyl-6,7-dihydro-1H-indol-4(5H)-one; 1-(4-amino-8-(2-aminophenylthio)quinazolin-7-yI)-3,6,6-trimethyl-6,7-dihydro-1H-indol-4(5H)-one;

1-(4-amino-8-(isopropylthio)quinazolin-7-yI)-3,6,6-trimethyl-6,7-dihydro-1H-indol-4(5H)-one;

1-(4-amino-8-(dimethylamino)quinazolin-7-yI)-3,6,6-trimethyl-6,7-dihydro-1H-indol-4(5H)-one;

1-(4-amino-8-(cyclopentylthio)quinazolin-7-yI)-3,6,6-trimethyl-6,7-dihydro-1H-indol-4(5H)-one;

1-(4-amino-8-(tetrahydro-2H-pyran-4-yloxy)quinazolin-7-yl)-3,6,6-trimethyl-6,7-dihydro-1H-indol-4(5H)-one;

1-(2-amino-4-ethylquinazolin-7-yI)-3,6,6-trimethyl-6,7-dihydro-1H-indol-4(5H)-one;

1-(2-amino-5-methoxy-4-methylquinazolin-7-yI)-3,6,6-trimethyl-6,7-dihydro-1H-indol-4(5H)-one;

1-(2-amino-4-methylquinazolin-7-yI)-2,6,6-trimethyl-6,7-dihydro-1H-indol-4(5H)-one;

1-(2-am ino-4-methylquinazolin-7-yI)-6,7-dihydro-1H-indol-4(5H)-one; 1-(4-amino-8-(3,5-dimethoxybenzyloxy)quinazolin-7-yl)-3,6,6-trimethyl-6,7-dihydro-1H-indol-4(5H)-one;

1-(2-amino-4-chloroquinazolin-7-yl)-3,6,6-trimethyl-6,7-dihydro-1H-indol-4(5H)-one;

1-(4-Amino-quinazolin-7-yl)-3-methyl-1,5,6,7-tetrahydro-indol-4-one;

1-(4-Amino-quinazolin-7-yl)-6,6-dimethyl-3-trifluoromethyl-1,5,6,7-tetrahydro-indazol-4-one; and 1-(2-amino-4-chloroquinazolin-7-yl)-3,6,6-trimethyl-6,7-dihydro-1H-indol-4(5H)-one;

or pharmaceutically acceptable salts thereof.

46. A pharmaceutical composition comprising the compound or salt according to claim 1, and a pharmaceutically acceptable excipient.

* * * * *